US007244761B2

(12) United States Patent
Kimura et al.

(10) Patent No.: US 7,244,761 B2
(45) Date of Patent: Jul. 17, 2007

(54) NERVE REGENERATION PROMOTERS CONTAINING SEMAPHORIN INHIBITOR AS THE ACTIVE INGREDIENT

(75) Inventors: Toru Kimura, Kusatsu (JP); Kaoru Kikuchi, Takarazuka (JP); Kazuo Kumagai, Sanda (JP); Nobuo Hosotani, Nishinomiya (JP); Akiyoshi Kishino, Suita (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 257 days.

(21) Appl. No.: 10/343,125

(22) PCT Filed: Jul. 27, 2001

(86) PCT No.: PCT/JP01/06501

§ 371 (c)(1),
(2), (4) Date: Jan. 28, 2003

(87) PCT Pub. No.: WO02/09756

PCT Pub. Date: Feb. 7, 2002

(65) Prior Publication Data

US 2003/0166711 A1    Sep. 4, 2003

(30) Foreign Application Priority Data

Jul. 28, 2000   (JP)   .............................. 2000-228555
Dec. 22, 2000   (JP)   .............................. 2000-390985

(51) Int. Cl.
*A61K 31/405* (2006.01)
*C07D 311/80* (2006.01)
*C07D 311/00* (2006.01)
*C12Q 1/50* (2006.01)

(52) U.S. Cl. .................... 514/455; 435/17; 549/391; 549/413

(58) Field of Classification Search .............. 549/391, 549/393, 413; 514/455; 435/171, 933, 17
See application file for complete search history.

(56) References Cited

U.S. PATENT DOCUMENTS

| 5,229,123 A | * | 7/1993 | Masubuchi et al. .......... 424/408 |
| 5,292,648 A | * | 3/1994 | Masubuchi et al. .......... 435/119 |
| 5,416,197 A | | 5/1995 | Raper et al. |
| 5,639,856 A | | 6/1997 | Goodman et al. |
| 5,807,826 A | | 9/1998 | Goodman et al. |
| 5,935,865 A | | 8/1999 | Goodman et al. |
| 6,013,781 A | | 1/2000 | Goodman et al. |
| 6,344,544 B1 | | 2/2002 | Goodman et al. |

FOREIGN PATENT DOCUMENTS

| EP | 537622 A1 | 4/1993 |
| JP | 6-506202 A | 7/1994 |
| WO | WO 92/16517 | 10/1992 |
| WO | WO 98/11216 A1 | 3/1998 |
| WO | WO 98/15628 A1 | 4/1998 |
| WO | WO 98/20928 A1 | 5/1998 |
| WO | WO 00/31252 A1 | 6/2000 |

OTHER PUBLICATIONS

Pasterkamp et al, Jol. of Neuroscience, "Evid. role of chemorepellant semaphorin III and recptor neuropilin-1 in regeneration of primary olfactory axons", Dec. 1, 1998.*
Wrigley et al., Pure & Appl. Chem. vol. 66, No. 10/11, pp. 2383-2386 (1994).*
Yoshio Goshima et al., "Functions of Semaphorins in Axon Guidance and Neuronal Regeneration", Jpn. J. Pharmacol. 82, pp. 273-279 (2000).
John G. Flanagan et al., "The kit Ligand: A Cell Surface Molecule Altered in Steel Mutant Fibroblasts", Cell, vol. 63, pp. 185-194, Oct. 5, 1990, Boston, Massachusetts.
Stephen K. Wrigley et al., "Structure elucidation of xanthone derivatives with CD4-binding activity from Penicillium glabrum (Wehmer) Westling", Pure & Appl.Chem., vol. 66, Nos. 10/11, pp. 2383-2386, 1994, Great Britain.
Yoshio Goshima et al. "Functions of semaphorins in axon guidance and neuronal regeneration", Jpn. J. Pharmacol., 2000, pp. 273-279, vol. 82.
Stephen K. Wrigley, "Structure elucidation of xanthone derivatives with CD4-binding activity from Penicillium glabrum (Wehmer) Westling", Pure Appl. Chemistry, 1994, pp. 2383-2386, vol. 66 (10/11).
Maio S. Chen et al., "Nogo-A is a myelin-associated neurite outgrowth inhibitor and an antigen for monoclonal antibody IN-1", Nature, Jan. 27, 2000, pp. 434-439, vol. 103, Macmillan Magazine Ltd.
Nature, Jan. 27, 2000, p. 440-444, vol. 403, Macmillan Magazines Ltd.
J.A. Bamberg, et al."Unified Nomenclature for the semaphorins/Collapsins", Cell, May 28, 1999, pp. 551-552, vol. 97, Cell Press.

(Continued)

*Primary Examiner*—Kamal A. Saeed
*Assistant Examiner*—Susannah L. Chung
(74) *Attorney, Agent, or Firm*—Ann S. Hobbs; Robert Kinberg; Venable LLP

(57) ABSTRACT

To provide a semaphorin inhibitor; a peripheral or central nerve regeneration promoter which contains said semaphorin inhibitor as an active ingredient; and a preventive or remedy for a neuropathic disease and a neurodegenerative disease containing said nerve regeneration promoter, or the like.

A low-molecular weight compound, which acts at a concentration of 10 μg/ml or below to inhibit the growth cone collapse activity of semaphorin such as semaphorin 3A, semaphorin 6C or the like and/or the nerve outgrowth inhibitory activity of semaphorin in a collagen gel and which does not substantially affect cell proliferation, is obtained from the culture of strain SPF-3059 belonging to the genus *Penicillium*. The low-molecular weight compound with the semaphorin inhibitory activity thus obtained exhibits the in vivo nerve-regeneration promoting action.

42 Claims, 12 Drawing Sheets

OTHER PUBLICATIONS

Yuling Luo et al., "Collapsin: A Protein in Brain That Induces the Collapse and Paralysis of Neuronal Growth Cones", Cell, Oct. 22, 1993, pp. 217-227, vol. 75, Cell Press.

Alex L. Kolodkin et al., "The semaphorin Genes Encode a Family of Transmembrane and Secreted Growth Cone Guidance Molecules", Cell, Dec. 31, 1993, p. 1389-1399, vol. 75, Cell Press.

Takashi Kitsukawa et al. "Neuropilin-Semaphorin III/D-Mediated Chemorepulsive Signals Play a Crucial Role in Peripheral Nerve Projection in Mice", Neuron, Nov. 1997, pp. 995-1005, vol. 19, Cell Press.

Andreas W. Püschel, et al. "Murine Semaphorin D/Collapsin Is a Member of a Diverse Gene Family and Creates Domains Inhibitory for Axonal Extension", Neuron, May 1995, p. 941-948, vol. 14, Cell Press.

Kaoru Kikuchi et al., "Cloning and Characterization of a Novel Class VI Semaphorin, Semaphorin Y", Molecular and Cellular Neuroscience, 1999, pp. 9-23, vol. 13, Academic Press.

Masahiro Aoki et al, Structure of a Novel Phospholipase C Inhibitor, Vinaxanthone (RO 09-1450), Produced by *Penicillium vinaceum*, *Tetrahedron Letters*, vol. 32, No. 36, 1991, pp. 4737-4740.

\* cited by examiner ature. Although similar motor abnormality in nervous systems is observed in Sema3A knockout mice, some individual mice are reported to grow up to adults without serious problem. Therefore, the in vivo functions of Sema3A remain largely unknown.

NERVE REGENERATION PROMOTERS CONTAINING SEMAPHORIN INHIBITOR AS THE ACTIVE INGREDIENT

TECHNICAL FIELD

The present invention relates to central or peripheral nerve regeneration promoters containing semaphorin inhibitor as an active ingredient, to preventives and remedies for neurodegenerative diseases or the like which contain the nerve regeneration promoters, to non-peptide and non-nucleotide semaphorin inhibitors, to compounds with the semaphorin inhibitory activity, and to a microbiological process for producing the said compounds or the like.

BACKGROUND ART

Nerve cells are particular tissues, which has no mitotic potential in an adult. Therefore, once they are injured, the damage will last over a long period of time. It is said that there is no regeneration potential especially in the central nervous system (CNS) such as brain and spinal cord. Lack of the regeneration potential in the central nerves can be regarded as one of the reasons that there have been no established therapies for traumatic injuries such as spinal cord injury, nor for neurodegenerative diseases such as Alzheimer's disease and Parkinson disease. On the other hand, peripheral nerves possess regeneration potential. Their axons can regenerate and their functions can be recovered even after having been severed. In this case, however, the recovery requires a long span of time ranging from several months to even more than a year, and thus patients have to undergo considerable sufferings. Moreover, the recovery period is so long that some nerve cells may die during this period, which often leads to the failure of recovery of the functions. And yet, even the peripheral nerves having regeneration potential are entirely unable to outgrow in the CNS such as in brain and spinal cord. This brings the basis for the hypothesis that there exist some substances in the central nervous system that inhibit nerve outgrowth. If the inhibitory substances for nerve regeneration in the central nervous system are suppressed by using antibodies or the like, nerve regeneration in the CNS as well as the recovery of their functions will be observed, even though partially. As one of such inhibitory substances for the central nerve regeneration, Nogo has been recently discovered (Nature 403, 434, 2000, Nature 403, 439, 2000). However, only a small portion of axons are regenerated by inhibiting Nogo and it is thus presumed that there exist some other regeneration-inhibitory substances. The followings are exemplified as candidate substances that inhibit the nerve regeneration: MAG (myelin-associated glycoprotein); tenascin; gangliosides; ephrin; netrin; slit; semaphorins and the like. The only reason for these substances to be exemplified as the candidate substances is that they inhibit neurite outgrowth in vitro. Whether they actually act to inhibit nerve regeneration in vivo has not yet been elucidated so far.

Referring to semaphorin, its gene was first isolated as a factor involved in nervous system formation in developing locusts. Since then, it has been reported that semaphorins constitute a large gene family distributing in nematodes, fish, mammals or even certain kinds of virus, and currently semaphorin genes are classified into eight gene subfamilies or classes based on their structures (Cell 97, 551, 1999). Semaphorin is an endogenous protein identified as a factor which collapses nerve growth cone and suppresses axon outgrowth, and so far, about 20 molecular species have been reported (Cell 97, 551, 1999). However, most functions of many semaphorin families have not yet been discovered in detail. The most studied gene group is that of a subfamily called the class III type, all of whose translation products are secretory proteins. Although proteins encoded by these genes are known to possess intensive neurite outgrowth suppressing activity and growth cone collapse activity in vitro, it was reported that they induce neurite outgrowth under certain conditions. Among them, semaphorin 3A (Sema3A) is the most studied and is known to induce growth cone collapse of the cultured nerve cells at as low as 10 pM concentration in a short period of time (Cell 75, 217, 1993, Cell 75, 1389, 1993). In order to analyze in vivo functions of semaphorins, knockout mice for neuropilin-1, which is one of the components of Sema3A receptor, have been studied (Neuron 19, 995, 1997). The said knockout mice show embryonic lethality as well as motor abnormality in some nervous systems such as trigeminal nerve and angiogenesis abnormality. Although similar motor abnormality in nervous systems is observed in Sema3A knockout mice, some individual mice are reported to grow up to adults without serious problem. Therefore, the in vivo functions of Sema3A remain largely unknown.

Moreover, with regard to semaphorins the followings are also known: antisense nucleototides and antagonists such as antibodies or the like for semaphorin W, semaphorin Y and semaphorin Z are made for central nerve regeneration promoters (WO98/15628, WO98/11216, WO98/20928); and a method of inducing neurite outgrowth by contacting a nerve cell with an antibody that specifically binds to human collapsin is known (U.S. Pat. No. 5,416,197). However, in vivo actions of these antibodies or the like still remain unknown. Besides, any low-molecular weight compounds other than peptide or nucleotide such as an antibody or an antisense nucleotide or the like, which specifically inhibits semaphorin have been completely unknown.

The subject of the present invention is to provide semaphorin inhibitors, peripheral or central nerve regeneration promoters that contain the said semaphorin inhibitors as an active ingredient, preventives and remedies for neuropathic diseases and neurodegenerative diseases that contain the nerve regeneration promoters.

DISCLOSURE OF THE INVENTION

Semaphorins are thought to have various actions, and some researchers postulated that semaphorins were involved not only in the nerve development but also in the nerve regeneration, though there were little evidence. Further, a gene deficient animal does not always serve as a tool for evaluating the function of the gene because the loss of the gene function often induce a compensatory action by other genes, as observed in MAG knockout animal. Although MAG had been thought for years as a result of a number of studies to be one of inhibitory substances for nerve regeneration, MAG knockout mice did not show promotion of nerve regeneration. The present inventors, therefore, commenced the study on semaphorin to examine whether inhibition of semaphorin brings about the in vivo nerve regeneration without using semaphorin knockout animals.

First, a substance that entirely inhibits the semaphorin activity in vitro was screened, and thus screened semaphorin inhibitor was administered to a nerve regeneration animal model to clarify the in vivo nerve-regeneration promoting activity of said semaphorin inhibitor. As a result of this study, the present inventors have found that a substance, which not only inhibits the growth cone collapse activity of semaphorin entirely but also persistently inhibits the semaphorin activity in a collagen gel and promotes neurite outgrowth in the presence of semaphorin, and exhibits the in vivo nerve-regeneration promoting activity. The present inventors have further found that nerve regeneration was promoted not only in the peripheral nervous system but in the CNS by using the semaphorin inhibitor. The study not only elucidated the in vivo action of semaphorin but also made it possible to provide nerve regeneration promoter containing a semaphorin inhibitor, which has been completely undiscovered, as an active ingredient, and a pharmaceutical containing the nerve regeneration promoter. The study have also elucidated that a compound with a specific structure in the molecule discovered in the culture of *Penicillium* sp. SPF-3059, which was screened by the present inventors, exhibits semaphorin inhibitory activity. The present invention was accomplished based on these findings.

The present invention relates to: a nerve regeneration promoter containing an inhibitor for a nerve outgrowth repelling factor as an active ingredient; the nerve regeneration promoter, wherein the inhibitor for a nerve outgrowth repelling factor is a semaphorin inhibitor; the nerve regeneration promoter, wherein the semaphorin inhibitor is a class 3 semaphorin inhibitor; the nerve regeneration promoter, wherein the class 3 semaphorin inhibitor is a semaphorin 3A inhibitor; the nerve regeneration promoter, wherein the semaphorin inhibitor is a class 6 semaphorin inhibitor; the nerve regeneration promoter, wherein the class 6 semaphorin inhibitor is a semaphorin 6C inhibitor; the nerve regeneration promoter according to any of the above, wherein the semaphorin inhibitor is a compound having promoting action on the central and/or the peripheral nerve regeneration; the nerve regeneration promoter according to any of the above, wherein the semaphorin inhibitor is a compound having suppressing action on the growth cone collapse activity of semaphorin and/or on the nerve outgrowth inhibitory activity of semaphorin in a collagen gel; the nerve regeneration promoter having said suppressing action, wherein the compound having suppressing activity for the growth cone collapse activity and/or suppressing action on the nerve outgrowth inhibitory activity in a collagen gel exhibits said suppressing action at a concentration of 100 μg/ml or below; the nerve regeneration promoter exhibiting suppressing action in this concentration range, wherein the compound having suppressing activity for the growth cone collapse activity and/or suppressing action on the nerve outgrowth inhibitory activity in a collagen gel exhibits said suppressing action at a concentration of 10 μg/ml or below; the nerve regeneration promoter exhibiting suppressing action at a concentration of 10 μg/ml or below, wherein the compound having suppressing activity on the growth cone collapse activity and/or suppressing action on the nerve outgrowth inhibitory activity in a collagen gel exhibits said suppressing action at a concentration of 3 μg/ml or below; the nerve regeneration promoter according to any of the above descriptions, wherein the semaphorin inhibitor is a compound which inhibits the function of semaphorin by contacting said semaphorin; the nerve regeneration promoter according to any of the above descriptions, wherein the semaphorin inhibitor is a compound which does not substantially affect cell proliferation; the nerve regeneration promoter according to any of the above descriptions, wherein the semaphorin inhibitor is a compound with a molecular weight of 1000 or less; the nerve regeneration promoter according to any of the above descriptions, wherein the semaphorin inhibitor is a non-peptide and a non-nucleotide compound; the nerve regeneration promoter that is a non-peptide, non-nucleotide semaphoring inhibitor, wherein the non-peptide and the non-nucleotide compound is obtained from cultivating *Penicillium* sp. SPF-3059; and the nerve regeneration promoter obtained from cultivating *Penicillium* sp. SPF-3059, wherein the non-peptide and the non-nucleotide compound obtained from cultivating *Penicillium* sp. SPF-3059 contains a group represented by formulae [1], [2], [4] or [5] and/or a group represented by formulae [6] or [7] in the molecule,

[Chemical formula 1]

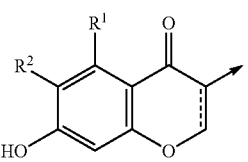

[1]

wherein,

[Chemical formula 2]

----- represents a single bond or a double bond, $R^1$ represents a hydrogen atom, a carboxyl group or an alkoxycarbonyl group and $R^2$ represents a hydrogen atom, a hydroxyl group or an acyloxy group,

[Chemical formula 3]

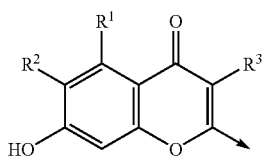

[2]

wherein $R^1$ and $R^2$ have the same meanings as in formula [1] and $R^3$ represents a hydrogen atom, a methoxymethyl group or formula [3],

[Chemical formula 4]

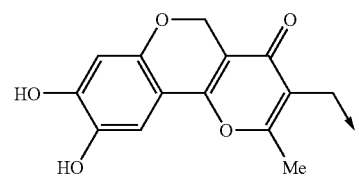

[3]

[Chemical formula 5]

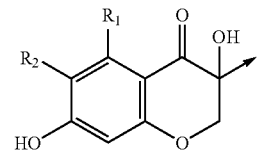

[4]

wherein $R^1$ and $R^2$ have the same meanings as in formula [1],

[Chemical formula 6]

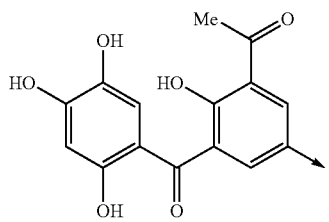

[Chemical formula 7]

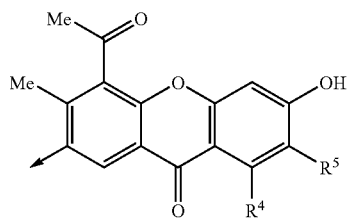

wherein $R^4$ represents a hydrogen atom, a carboxyl group or an alkoxycarbonyl group and $R^5$ represents a hydrogen atom, a hydroxyl group or an acyloxy group,

[Chemical formula 8]

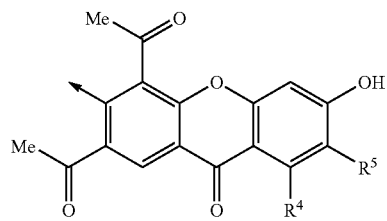

wherein $R^4$ and $R^5$ have the same meanings as in formula [6] (claim 17).

The present invention further relates to: a semaphorin inhibitor containing a compound which has a group represented by formulae [1], [2], [4] or [5] and a group represented by formulae [6] or [7] in the molecule, a pharmaceutically acceptable salt thereof or a derivative thereof, as an active ingredient,

[Chemical formula 9]

[1]

wherein,

[Chemical formula 10]

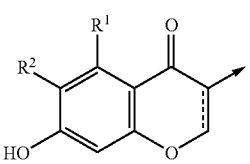

represents a single bond or a double bond, $R^1$ represents a hydrogen atom, a carboxyl group or an alkoxycarbonyl group and $R^2$ represents a hydrogen atom, a hydroxyl group or an acyloxy group,

[Chemical formula 11]

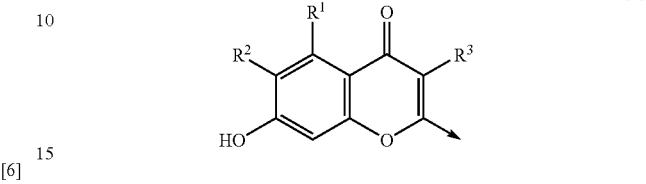

[2]

wherein $R^1$ and $R^2$ have the same meanings as in formula [1] and $R^3$ represents a hydrogen atom, a methoxymethyl group or formula [3],

[Chemical formula 12]

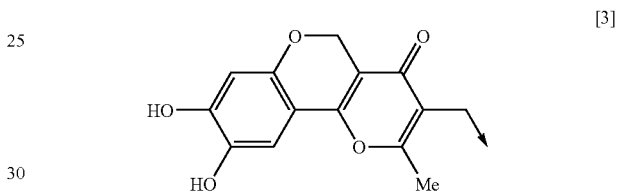

[3]

[Chemical formula 13]

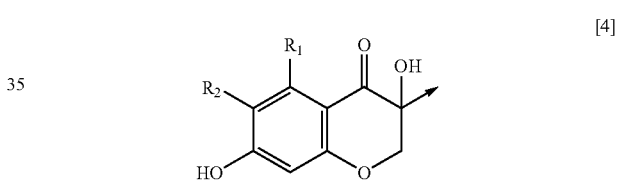

[4]

wherein $R^1$ and $R^2$ have the same meanings as in formula [1],

[Chemical formula 14]

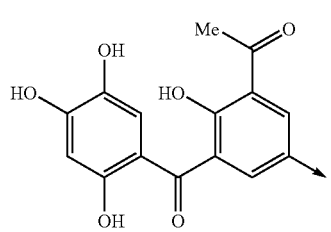

[5]

[Chemical formula 15]

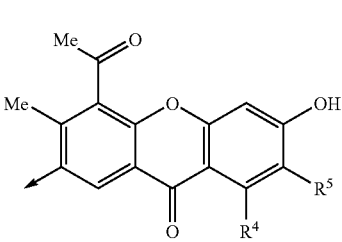

[6]

wherein $R^4$ represents a hydrogen atom, a carboxyl group or an alkoxycarbonyl group and $R^5$ represents a hydrogen atom, a hydroxyl group or an acyloxy group,

[Chemical formula 16]

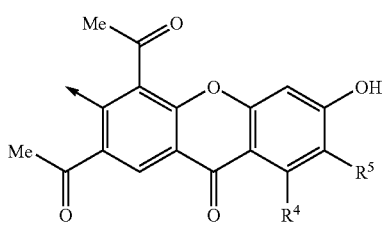

[7]

wherein $R^4$ and $R^5$ have the same meanings as in formula [6]; a semaphorin inhibitor containing a compound represented by formula [8], a pharmaceutically acceptable salt thereof or a derivative thereof, as an active ingredient,

[Chemical formula 17]

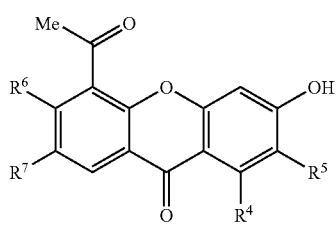

[8]

wherein $R^4$ and $R^5$ have the same meanings as in formula [6] and $R^6$ and $R^7$ are represented by either (1) or (2) below: (1) $R^6$ represents a methyl group and $R^7$ represents a group shown by formulae [2], [9] or [10],

[Chemical formula 18]

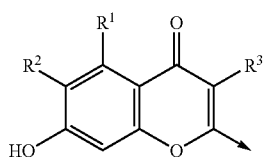

[2]

wherein $R^1$ and $R^2$ have the same meanings as in formula [1] and $R^3$ represents a hydrogen atom, a methoxymethyl group or formula [3],

[Chemical formula 19]

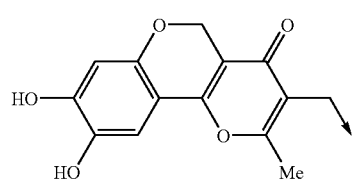

[3]

[Chemical formula 20]

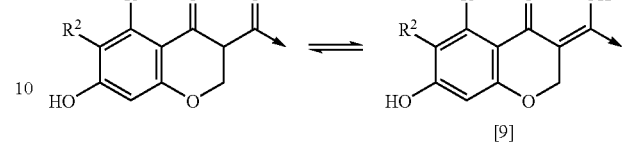

[9]

wherein $R^1$ and $R^2$ have the same meanings as in formula [1],

[Chemical formula 21]

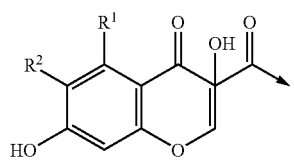

[10]

wherein $R^1$ and $R^2$ have the same meanings as in formula [1], (2) $R^6$ represents a group shown by formulae [5] or [11] and $R^7$ represents an acetyl group,

[Chemical formula 22]

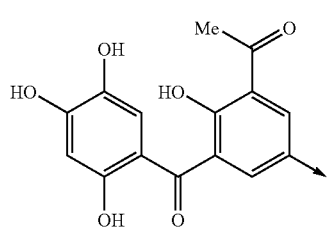

[5]

[Chemical formula 23]

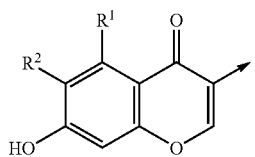

[11]

a semaphorin inhibitor containing a compound represented by formula [12], a pharmaceutically acceptable salt thereof or a derivative thereof, as an active ingredient,

[Chemical formula 24]

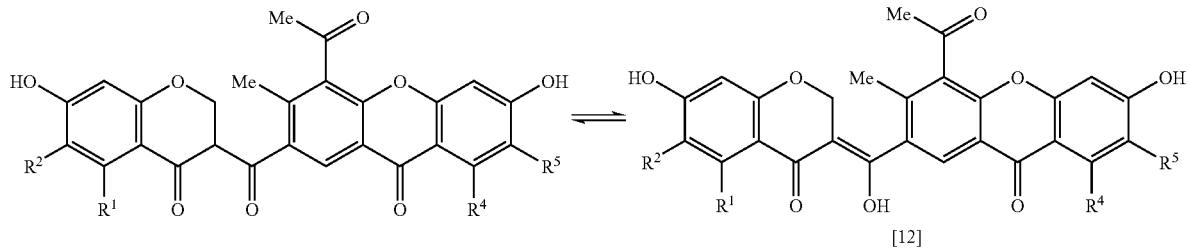

wherein $R^1$, $R^2$, $R^4$ and $R^5$ have the same meanings as in formulae [1] and [6]; the semaphorin inhibitor according to this formula which contains a compound wherein at least one of $R^2$ and $R^5$ represents a hydroxyl group in formula [12], a pharmaceutically acceptable salt thereof or a derivative thereof, as an active ingredient; the semaphorin inhibitor according to the above which contains a compound wherein $R^2$ represents a hydroxyl group in formula [12], a pharmaceutically acceptable salt thereof or a derivative thereof, as an active ingredient; the semaphorin inhibitor according to the above which contains a compound wherein $R^2$ and $R^5$ represent a hydroxyl group in formula [12], a pharmaceutically acceptable salt thereof or a derivative thereof, as an active ingredient; the semaphorin inhibitor according to any of the above which contains a compound wherein $R^4$ represents a carboxyl group in formula [12], a pharmaceutically acceptable salt thereof or a derivative thereof, as an active ingredient; the semaphorin inhibitor according to the above which contains a compound wherein $R^1$ and $R^4$ represent a carboxyl group and $R^2$ represents a hydroxyl group in formula [12], a pharmaceutically acceptable salt thereof or a derivative thereof, as an active ingredient; and a nerve regeneration promoter containing the semaphorin inhibitor according to any of the above as an active ingredient.

The present invention still further relates to: a compound represented by formula [12], wherein at least one of $R^1$, $R^2$, $R^4$ and $R^5$ is represented by a hydrogen atom, a pharmaceutically acceptable salt thereof or a derivative thereof, according to the above wherein $R^2$ and $R^5$ represent a hydroxyl group, a pharmaceutically acceptable salt thereof or a derivative thereof; the compound according to any of the above wherein $R^4$ represents a carboxyl group, a pharmaceutically acceptable salt thereof or a derivative thereof; and the compound according to the above wherein $R^1$ and $R^4$ represent a carboxyl group and $R^2$ represents a hydroxyl group, a pharmaceutically acceptable salt thereof or a derivative thereof.

The present invention further relates to: a semaphorin inhibitor containing a compound represented by formula [13], a pharmaceutically acceptable salt thereof or a derivative thereof, as an active ingredient,

[Chemical formula 26]

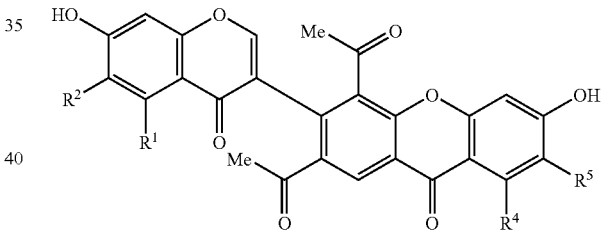

[Chemical formula 25]

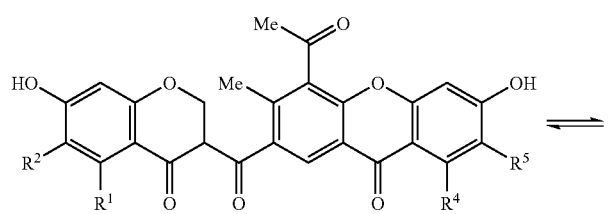
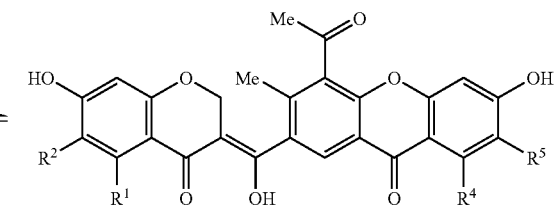

wherein $R^1$, $R^2$, $R^4$ and $R^5$ have the same meanings as in formulae [1] and [6]; the compound according to the above wherein at least one of $R^2$ and $R^5$ represents a hydroxyl group, a pharmaceutically acceptable salt thereof or a derivative thereof; the compound according to the above wherein $R^2$ represents a hydroxyl group, a pharmaceutically acceptable salt thereof or a derivative thereof; the compound wherein $R^1$, $R^2$, $R^4$ and $R^5$ have the same meanings as in formulae [1] and [6]; the semaphorin inhibitor according to the above which contains a compound wherein at least one of $R^2$ and $R^5$ represents a hydroxyl group in formula [13], a pharmaceutically acceptable salt thereof or a derivative thereof, as an active ingredient; the semaphorin inhibitor according to the above which contains a compound wherein $R^2$ represents a hydroxyl group in formula [13], a pharmaceutically acceptable salt thereof or a derivative thereof, as an active ingredient; the semaphorin inhibitor according to the above which contains a compound wherein $R^2$ and $R^5$ represent a hydroxyl group in formula [13], a pharmaceutically acceptable salt thereof or a derivative thereof, as an active ingredient; the semaphorin inhibitor according to any of the above which contains a compound wherein $R^4$ represents a carboxyl group in formula [13], a pharmaceutically acceptable salt thereof or a derivative thereof, as an active ingredient; the semaphorin inhibitor according to the above which contains a compound wherein $R^2$ and $R^5$ represent a hydroxyl group, $R^1$ represents a carboxyl group and $R^4$ represents a hydrogen atom in formula [13], a pharmaceutically acceptable salt thereof or a derivative thereof, as an active ingredient; the semaphorin inhibitor according to the above which contains a compound wherein $R^1$ and $R^4$ represent a carboxyl group and $R^5$ represents a hydroxyl group in formula [13], a pharmaceutically acceptable salt thereof or a derivative thereof, as an active ingredient; and a nerve regeneration promoter containing the semaphorin inhibitor according to any of the above as an active ingredient.

The present invention still further relates to: a compound represented by formula [13], wherein at least one of $R^1$, $R^2$ and $R^5$ represents a hydrogen, a pharmaceutically acceptable salt thereof or a derivative thereof,

[Chemical formula 27]

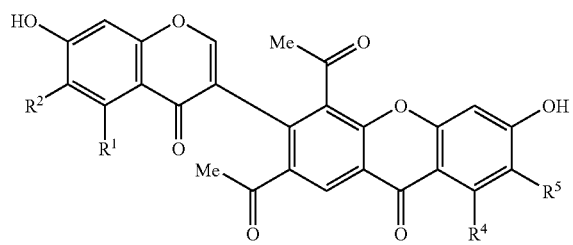

[13]

wherein $R^1$, $R^2$, $R^4$ and $R^5$ have the same meanings as in formulae [1] and [6]; the compound according to the above wherein at least one of $R^2$ and $R^5$ represents a hydroxyl group, a pharmaceutically acceptable salt thereof or a derivative thereof; the compound according to the above wherein $R^2$ represents a hydroxyl group, a pharmaceutically acceptable salt thereof or a derivative thereof; the compound according to the above wherein $R^2$ and $R^5$ represent a hydroxyl group, a pharmaceutically acceptable salt thereof or a derivative thereof; the compound according to any of the above wherein $R^4$ represents a carboxyl group, a pharmaceutically acceptable salt thereof or a derivative thereof; the compound according to the above wherein $R^2$ represents a hydroxyl group and $R^4$ represents a carboxyl group, a pharmaceutically acceptable salt thereof or a derivative thereof; the compound according to the above wherein $R^1$ and $R^4$ represent a carboxyl group and $R^5$ represents a hydroxyl group, a pharmaceutically acceptable salt thereof or a derivative thereof; a compound represented by formula [14], a pharmaceutically acceptable salt thereof or a derivative thereof,

[Chemical formula 28]

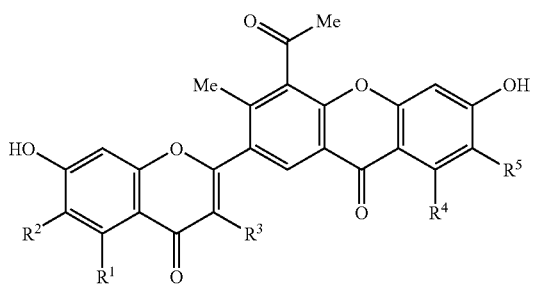

[14]

wherein $R^1$, $R^2$, $R^3$, $R^4$ and $R^5$ have the same meanings as in formulae [2] and [6]; the compound according to the above wherein at least one of $R^2$ and $R^5$ represents a hydroxyl group, a pharmaceutically acceptable salt thereof or a derivative thereof; the compound according to the above wherein $R^2$ represents a hydroxyl group, a pharmaceutically acceptable salt thereof or a derivative thereof; the compound according to the above wherein $R^2$ and $R^5$ represent a hydroxyl group, a pharmaceutically acceptable salt thereof or a derivative thereof; the compound according to any of the above wherein $R^4$ represents a carboxyl group, a pharmaceutically acceptable salt thereof or a derivative thereof; the compound according to the above wherein $R^1$ and $R^4$ represent a carboxyl group and $R^2$ and $R^5$ represent a hydroxyl group, a pharmaceutically acceptable salt thereof or a derivative thereof; the compound according to the above wherein $R^1$ represents a carboxyl group, $R^2$ and $R^5$ represent a hydroxyl group and $R^3$ represents a methoxymethyl group, a pharmaceutically acceptable salt thereof or a derivative thereof; the compound according to the above wherein $R^1$ represents a carboxyl group or a methoxycarbonyl group, $R^4$ represents a carboxyl group, $R^3$ represents a hydrogen atom and $R^5$ represents a hydroxyl group, a pharmaceutically acceptable salt thereof or a derivative thereof; the compound according to the above wherein $R^1$ represents a carboxyl group or a methoxycarbonyl group, $R^4$ represents a carboxyl group, $R^2$ and $R^3$ represent a hydrogen atom and $R^5$ represents a hydroxyl group, a pharmaceutically acceptable salt thereof or a derivative thereof; the compound according to any of the above, wherein $R^3$ represents a group shown by formula [3], a pharmaceutically acceptable salt thereof or a derivative thereof;

[Chemical formula 29]

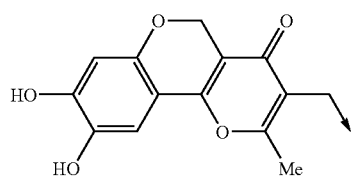

[3]

a semaphorin inhibitor containing a compound of any of the above, a pharmaceutically acceptable salt thereof or a derivative thereof, as an active ingredient; and a nerve regeneration promoter containing the semaphorin inhibitor according to the above as an active ingredient.

The present invention still further relates to: a compound represented by formula [15], a pharmaceutically acceptable salt thereof or a derivative thereof,

[Chemical formula 30]

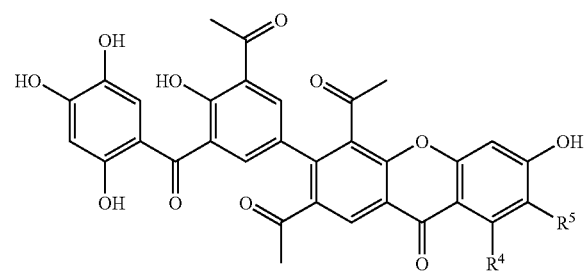

[15]

wherein $R^4$ and $R^5$ have the same meanings as in formula [6]; the compound of this description wherein $R^5$ represents a hydroxyl group, a pharmaceutically acceptable salt thereof or a derivative thereof; the compound according to either of these descriptions wherein $R^4$ represents a carboxyl group, a pharmaceutically acceptable salt thereof or a derivative thereof; a semaphorin inhibitor containing a compound of any the above, a pharmaceutically acceptable salt thereof or a derivative thereof, as an active ingredient; and a nerve regeneration promoter containing the semaphorin inhibitor as an active ingredient.

The present invention still further relates to: a compound represented by formula [16], a pharmaceutically acceptable salt thereof or a derivative thereof,

[Chemical formula 31]

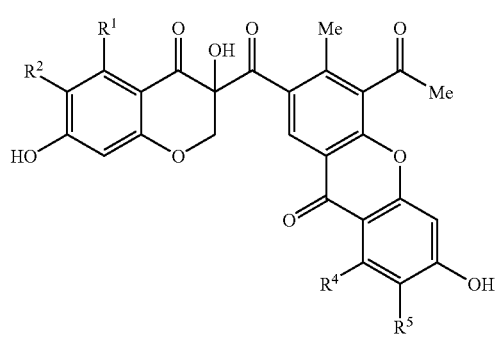

[16]

wherein $R^1$, $R^2$, $R^4$ and $R^5$ have the same meanings as in formulae [1] and [6]; the compound of this description wherein at least one of $R^2$ and $R^5$ represents a hydrogen atom, a pharmaceutically acceptable salt thereof or a derivative thereof; the compound according to this description wherein $R^2$ and $R^5$ represent a hydroxyl group, a pharmaceutically acceptable salt thereof or a derivative thereof; the compound according to any of the above wherein $R^4$ represents a carboxyl group, a pharmaceutically acceptable salt thereof or a derivative thereof; a semaphorin inhibitor containing a compound of any of these descriptions, a pharmaceutically acceptable salt thereof or a derivative thereof, as an active ingredient; and a nerve regeneration promoter containing the semaphorin inhibitor as an active ingredient.

The present invention still further relates to: a preventive or a remedy for neuropathic diseases and/or neurodegenerative diseases containing the nerve regeneration promoter of any of the above; the preventive or the remedy for neuropathic diseases and/or neurodegenerative diseases, wherein said neuropathic diseases and/or neurodegenerative diseases are accompanied with a spinal nerve injury and/or a peripheral nerve injury; the preventive or the remedy for neuropathic diseases and/or neurodegenerative diseases, wherein said neuropathic diseases and/or neurodegenerative diseases are olfactory abnormality, traumatic neuropathy, cerebral infarctional neuropathy, facial nerve paralysis, diabetic neuropathy, glaucoma, retinitis pigmentosa, Alzheimer's disease, Parkinson's disease, neurodegenerative diseases, muscular hypoplastic lateral sclerosis, Lou Gehrig's disease, Huntington's chorea, cerebral infarction or traumatic neurodegenerative diseases; a process for producing any of the compounds as described above, wherein the process comprises cultivating a compound-producing fungus which belongs to the genus *Penicillium* and collecting said compound from the culture; the production process according to the above, wherein the producing fungus which belongs to the genus *Penicillium* is *Penicillium* sp. SPF-3059; and *Penicillium* sp. SPF-3059 (FERM BP-7663) or a fungus strain induced from said SPF-3059.

BEST MODE OF CARRYING OUT THE INVENTION

Figure 1:
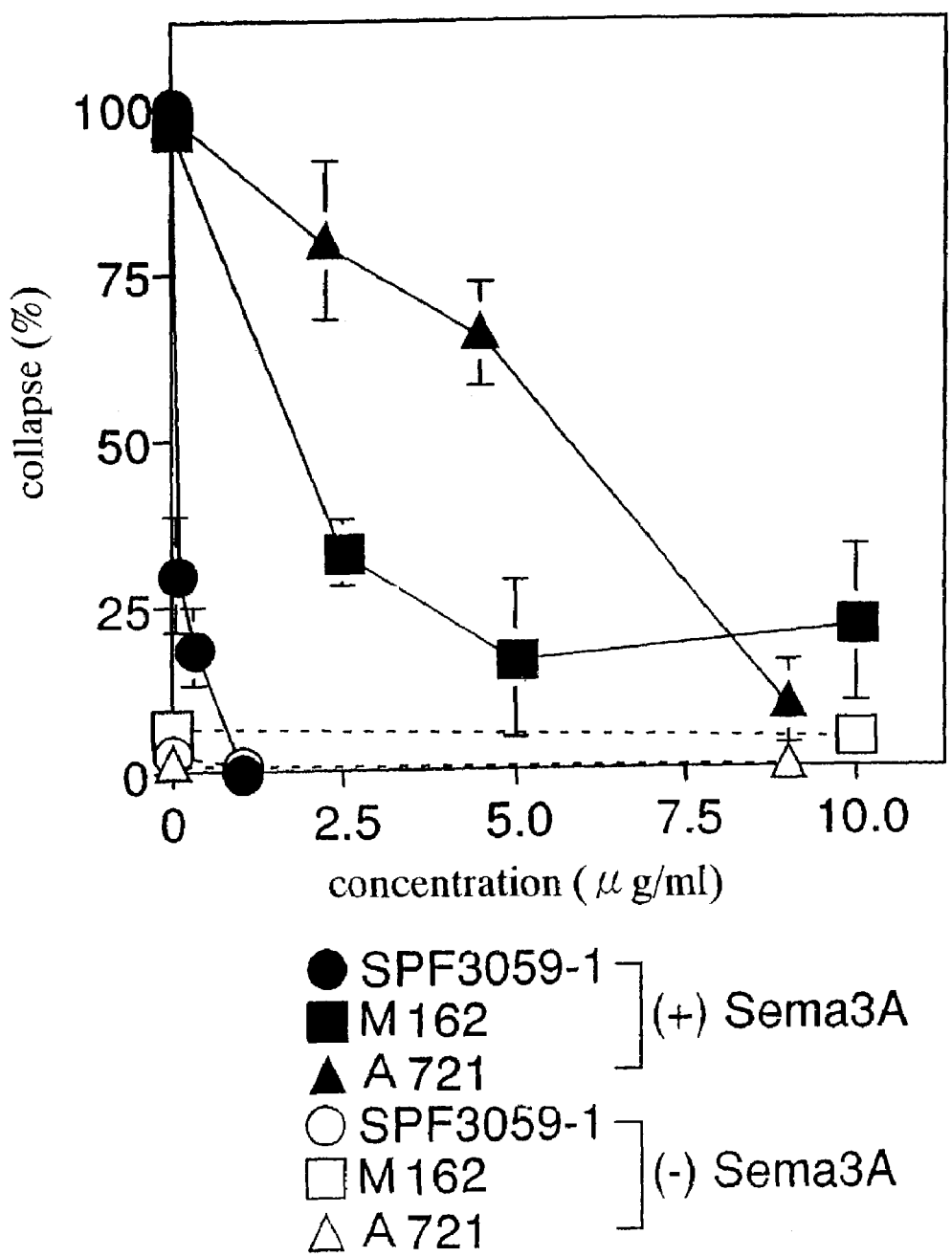
FIG. 1 shows the concentration-dependent inhibitory action of the semaphorin inhibitors of the present invention, SPF-3059-1, M162 and A721, on the growth cone collapse activity of Sema3A.

There is no particular limitation to a nerve regeneration promoter of the present invention as long as the promoter contains an inhibitor for a nerve outgrowth-repelling factor such as semaphorin or the like as an active ingredient. Here, semaphorin is a generic name for proteins that have semaphorin domains with similar structures consisting of about 500 amino acid residues (Neuron 14, 941–948, 1995), and approximately 20 variants or more have been reported to date. In the present invention, however, semaphorins will not be limited to these publicly known. The following can be exemplified as such semaphorins: semaphorins of mammals such as human, etc.; preferably class 3, 4, 5 or 6 semaphorins as defined in the literature (Cell 97, 551, 1999); more preferably class 3 or 6 semaphorins; and most preferably semaphorin 3A (Cell 75, 217, 1993, Cell 75,1389, 1993) in class 3 semaphorins and semaphorin 6C (WO98/11216, Moll. Cell. Neurosci. 13, 9–23 (1999)) in class 6 semaphorins. As sequence information regarding genes encoding these semaphorins is disclosed in GenBank data base, the aforementioned literatures or the like, cDNA encoding semaphorin can be cloned according to the said sequence information and by using, for example, a brain-derived cDNA library or the like with an appropriate portion of DNA as a probe for hybridization or as a primer for PCR. Those skilled in the art can easily perform these cloning according to basic protocols such as Molecular Cloning 2nd Ed., Cold Spring Harbor Laboratory Press (1989), etc. Besides, proteins can be produced according to various textbooks and literatures such as the aforementioned Molecular Cloning or the like by expressing a gene encoding the semaphorin thus obtained. Further, semaphorin of the present invention will not be limited only to a natural or a recombinant protein but also includes: a protein in which the extracellular domain of a membrane-bound semaphorin is expressed and solubilized; a fusion protein with other protein such as an antibody, alkaline phosphatase or the like; a protein to which a tag such as His-tag, Flag or the like is added; or a mutant in which part of amino acids are deleted, substituted or added.

For example, semaphorin 6C (Sema6C) is a membrane-bound protein and the extracellular domain of Sema6C is usually used such as for measuring the activity of a subject substance by utilizing promoting or suppressing actions of Sema6C activities. Two isoforms are known in the extracellular domain of Sema6C (WO98/11216 and Moll. Cell. Neurosci. 13, 9–23 (1999)), each of which has the growth cone collapse activity. A fusion protein in which the extracellular domain of said Sema6C and a marker protein and/or a peptide tag are bound can be advantageously used for such cases of measuring the activity of a subject substance as long as the activity of Sema6C is not impaired. Examples of marker proteins are conventionally well known marker proteins such as alkaline phosphatase (Cell 63, 185–194 (1990)), Fc region of an antibody (Genbank accession number M87789), HRP and the like, and peptide tags are exemplified by conventionally well known Mic-tag, His-tag, Flag-tag and the like.

In the present invention, a semaphorin inhibitor means a substance which inhibits an activity of any one of the aforementioned semaphorins such as, for instance, migration activity of a cell, cell death-inducing activity, morphological changes of a cell such as cell rounding or growth cone collapsing, suppressing or promoting activity for neurite outgrowth, suppressing or promoting activity for dendrite outgrowth of nerve cells, nerve axon guidance activity or the like. Any substance inhibiting the foregoing semaphorin activities can be adopted as said semaphorin inhibitor without particular limitation. Preferably, a compound having promoting action on central and/or peripheral nerve regeneration, more preferably a compound having suppressing action on the growth cone collapse activity and/or the nerve outgrowth inhibitory activity in a collagen gel, and even more preferably a compound having suppressing action on both growth cone collapse activity of semaphorin and nerve outgrowth inhibitory activity in a collagen gel are exemplified.

The above described promoting action on the central and/or peripheral nerve regeneration refers to an action which promotes nerve regeneration in the central nervous system (tissue) comprising such as brain, spinal cord and the like, and/or in the peripheral nervous system (tissue) which are in organs on body surface or in the body that consist the marginal and peripheral portions and not the said central nervous system (tissue). Here, promoting action on the central nerve regeneration includes promoting action not only on the nerve regeneration wherein an axon emerges from a nerve cell body in the central region, such as a retinal nerve or a cerebral cortex nerve, and is projected on other nerve cell which is also in the central, but also on the nerve regeneration wherein a nerve axon is regenerated in the central nervous system (tissue) circumstance even when a nerve, such as an afferent fiber of an olfactory nerve or a dorsal root ganglion sensory nerve, emerges from a nerve cell body in the peripheral. Further, promoting action on the peripheral nerve regeneration includes promoting action not only on the nerve regeneration of a nerve which emerges from a peripheral nerve cell body and extends in a peripheral tissue, but also on the nerve regeneration wherein the circumstance for regeneration is the peripheral nervous system (tissue) even when a nerve is emerged from a central nerve cell body (brain, spinal cord or the like). The latter can be exemplified by the nerve-regeneration promoting action for such as a spinal cord motor nerve, a preganglionic nerve in the autonomic nervous systems like sympathetic and parasympathetic nerves, and the like. Promoting action on regeneration of a nerve such as a sciatic nerve, which has both nerves mentioned above, is also included in the exemplification. A compound with promoting action on the central and peripheral nerve regeneration is particularly preferable for a semaphorin inhibitor of the present invention. The central nervous system (tissue) described earlier refers to a tissue comprising brain, medulla oblongata, spinal cord, eye and the like, and more particularly refers to a region where the transport of polymer substances is restricted by structures such as the blood-brain barrier and the blood-retina barrier. The peripheral nervous system (tissue) refers to the region of the other parts of the body. Nerve fibers are in general capable of regenerating in the peripheral nervous tissues, but they are unable to regenerate in the central nervous tissues.

The growth cone collapse activity of semaphorin described above means an activity to make growth cones disappear. This activity is observed after performing the following steps: cultivating nerve cells (generally tissue explants of ganglions) for a given period of time in vitro until the extended neurites as well as the growth cones at the edge of said neurites can be observed; and then adding thereto a given concentration (e.g. about 3 unit/ml; 1 unit/ml is defined as a semaphorin concentration in which 50% of the growth cones are collapsed) of semaphorin and cultivating for another given period of time (e.g. one hour). In order to get the extended neurites and the growth cones at the edge of said neurites ready for the observation, the nerve cells are generally cultivated for 10 to 20 hours in vitro, which duration can be altered according to a nerve variant and culture conditions. When the growth cone collapse caused by semaphorin is suppressed by, for example, the addition of a compound to this experimental system at an appropriate concentration about one hour prior to the addition of semaphorin, then such compound is regarded as a semaphorin inhibitor, especially as a compound with suppressing action on the growth cone collapse activity of semaphorin. Although there is no particular limitation to a compound with such suppressing action on the growth cone collapse activity, compounds can be exemplified which exhibit the said suppressing action at a concentration of 100 μg/ml or below, preferably 30 μg/ml or below, more preferably 10 μg/ml or below, and most preferably 3 μg/ml or below. Further, a compound which does not substantially affect proliferation of the cells such as nerve cells, semaphorin-expressing cells or the like is preferable as a semaphorin inhibitor in order to confirm the effect of semaphorin inhibitors of the present invention and in view of safety when used as a pharmaceutical.

The nerve outgrowth inhibitory activity of semaphorin in a collagen gel as described above means, for instance, the neurite outgrowth inhibitory activity observed in a collagen gel which contains, for example, both semaphorin-producing cells and nerve cells (usually ganglions). And suppressing action of said neurite outgrowth inhibitory activity is an activity to persistently inhibit the semaphorin activity in a collagen gel, and, for instance, is an activity by which neurites can outgrow to the side of semaphorin-producing cells as much as ½ or more of the outgrowth observed at the opposite side in the presence of the object substance under the experimental condition where neurites can only outgrow up to ⅓ or less to semaphorin producing cells compared with the growth observed at the opposite side of the semaphorin-producing cells when observed after cultivating semaphorin-producing cells and nerve cells adjacently in a collagen gel, usually for overnight or even longer. Further, there is no particular limitation to a compound with suppressing action on the neurite outgrowth inhibitory activity of semaphorin in said collagen gel. However, those exhibiting the foregoing suppressing action at a concentration of 100 μg/ml or less, preferably 30 μg/ml or less, more preferably 10 μg/ml or less and most preferably 3 μg/ml or less are exemplified.

Semaphorin used for measuring the two types of semaphorin activities mentioned above is not limited to a natural semaphorin and the following semaphorins described earlier can be used as well: semaphorin in which only the extracellular domain of a membrane-binding semaphorin is expressed and solubilized; a fusion protein with other protein such as an antibody, alkaline phosphatase or the like; semaphorin to which a tag such as a His-tag or a Flag is added; or semaphorin in which some amino acids are altered. Further, dorsal root ganglions from chick embryos of 7 or 8 embryonic days are conveniently used as nerve cells for the culture. However, dorsal root ganglions of animals other than chicks, or any other nerve cells such as sympathetic ganglions, retinal ganglions, superior cervical ganglions or the like other than dorsal root ganglions may also be used as long as the nerve cells are capable of extending their neurites in the in vitro culture. There is no particular limitation to the culture condition as long as neurite outgrowth can be observed and semaphorin activities can be measured.

The action mechanism of the semaphorin inhibitors of the present invention can be considered as follows. The neurite outgrowth inhibition or the growth cone collapse caused by semaphorin is triggered by binding of semaphorin to its receptor on the nerve cell surface (growth cone). The signal is transmitted from the receptor to which semaphorin is bound to the intracellular signaling pathway and depolymerization of actin fibers is finally raised, which as a result gives rise to the neurite outgrowth suppression and the growth cone collapse. Inhibition of semaphorin activity is achieved by inhibiting or blocking any of the steps in the course of these reactions. As the above-mentioned receptor for semaphorin, a receptor for any of the foregoing semaphorins may be adopted, and a mutant or a component of a part of such receptor may also be adopted provided that semaphorin can bind to it. The examples are Neuropilin-1, plexin and the like. The semaphorin inhibitors of the present invention will not be restricted by their action mechanisms and an inhibitor which inhibits any one of the steps in the above-described action mechanism is included in the category of the present invention. That is to say, a compound is also included in the category of the present invention, when the compound inhibits semaphorin activity by inhibiting the reactions concerning the intracellular signaling pathway which takes place from the aforementioned receptor-binding of semaphorin to the depolymerization of actin fibers. Besides, a method of measuring the receptor-binding inhibitory activity of semaphorin can be any method if appropriately selected by those skilled in the art, which is exemplified by a method of measuring the receptor-binding inhibitory activity of semaphorin wherein semaphorin fused with other protein such as an antibody, alkaline phosphatase or the like or semaphorin to which His-tag, Flag or the like is added, as described earlier, is bound to a receptor of said semaphorin or to a cell which expresses a receptor component in the presence of a subject substance.

For example, the inhibitory activity of SPF-3059-1 for the binding of Sema3A to Neuropilin-1 was actually examined by using the alkaline phosphatase-fused Sema3A (=Sema3A-AP) and Neuropilin-1-expressing COS7 cells. SPF-3059-1 is a compound discovered by the present inventors, which inhibits both collapse and neurite outgrowth inhibition induced by semaphorin 3A (Sema3A). The present study revealed that SPF-3059-1 inhibits the binding of Sema3A-AP to Neuropilin-1 in a concentration-dependent manner. Further, in order to elucidate the mechanism of the said inhibition, that is, in order to elucidate whether SPF-3059-1 interacts with Sema3A or with its receptor, the comparison was made by measuring collapse activity between (1) the collapse activity which was observed when a sample, to which SPF-3059-1 and Sema3A were mixed in advance at the concentration raising sufficient inhibitory activity (0.25 μg/ml of SPF-3059-1), was added to the culture solution of dorsal root ganglions and (2) the collapse activity which was observed when Sema3A was added to the above-mentioned culture solution after the addition of SPF-3059-1. The final concentration of SPF-3059-1 (0.05 μg/ml) in the culture solution was the same both for (1) and (2). Inhibition of collapse activity was not observed in (2) at this concentration of SPF-3059-1. However in (1), inhibition of collapse activity was observed. This result indicates that Sema3A has lost its collapse activity because SPF-3059-1 interacted with it. From the above considerations, SPF- 3059-1 is thought to act by a mechanism in which the binding of Sema3A to the receptor is inhibited by the direct action of SPF-3059-1 on Sema3A. When this finding is considered, a compound which inhibits the binding of semaphorin to its receptor by interacting directly with the semaphorin and which inhibits the function and the activity of the semaphorin is preferable for a semaphorin inhibitor of the present invention. A semaphorin inhibitor, particularly a compound which inhibits the function of semaphorin by interacting with it, can be screened by the above mentioned methods of measuring the collapse activity or the receptor-binding inhibitory activity, or the like.

A preferable compound for the semaphorin inhibitor of the present invention is a compound where the semaphorin inhibitor will not substantially affect cell proliferation, i.e. a compound not showing the suppressing action on cell proliferation, for example, a compound which does not show the suppressing action on cell proliferation at a concentration which is 50–3000 folds or higher than the concentration at which the semaphorin inhibitory activity can be observed. Further, although there is no particular limitation to molecular weight of semaphorin inhibitors of the present invention, a compound with a low molecular weight is desirable in view of diffusibility, membrane permeability, tissue distribution, especially blood-brain barrier permeability or the like, and suitable examples include a low molecular weight compound with a molecular weight of 10000 or less, preferably a molecular weight of 5000 or less, more preferably a molecular weight of 1000 or less and particularly a compound with a molecular weight of 600 or less. Still further, as for semaphorin inhibitors of the present invention, non-peptide and non-nucleotide compounds can be exemplified. Said non-peptide and non-nucleotide compounds are exemplified by an aliphatic synthesized compound M162, an actinomycete-derived compound A721, and most preferably, compounds obtained from the culture of *Penicillium* sp. SPF-3059 which is described later.

An example of the above-mentioned compounds obtained from the culture of *Penicillium* sp. SPF-3059 is a compound with semaphorin inhibitory activity which contains in its chemical structure a group represented by the above-mentioned general formulae [1], [2], [4] or [5] and/or a group represented by the above-mentioned general formula [6] or [7], preferably a compound represented by the above-mentioned general formula [8] and more preferably a compound represented by the above-mentioned general formula either [12] to [16]. In the general formulae [1], [2], [4], [9], [10], [11], [12], [13], [14] and [16] in these compounds, $R^1$ represents a hydrogen atom, a carboxyl group or an alkoxycarbonyl group, preferably a hydrogen atom or a carboxyl group, and a methoxycarbonyl group, an ethoxycarbonyl group, a propoxycarbonyl group and the like are exemplified as the above-mentioned alkoxycarbonyl group, among which a methoxycarbonyl group is preferable. Particularly, $R^1$ in the general formulae [1], [4], [9], [10], [11], [12], [13] and [16] preferably represent a hydrogen atom or a carboxyl group and $R^1$ in the general formulae [2] and [14] preferably represent a hydrogen atom, a carboxyl group or a methoxycarbonyl group where a hydrogen atom or a carboxyl group is more preferable. Similarly, $R^2$ in the general formulae [1], [2], [4], [9], [10], [11], [12], [13], [14] and [16] represent a hydrogen atom, a hydroxyl group or an acyloxy group, preferably a hydrogen atom or a hydroxyl group. As the above-mentioned acyloxy group, an acetoxy group, a propionyloxy group, a pivaloyloxy group and the like is exemplified as the above-mentioned acyloxy group. $R^3$ in the general formulae [2] and [14] represent a hydrogen atom, a methoxymethyl group or a group shown by the formula [3]. $R^4$ in the general formulae [6], [7], [8], [12], [13], [14], [15] and [16] represent a hydrogen atom, a carboxyl group or an alkoxycarbonyl group, preferably a hydrogen atom or a carboxyl group. The examples of the above-mentioned alkoxycarbonyl group are a methoxycarbonyl group, an ethoxycarbonyl group, a propoxycarbonyl group and the like, among which a methoxycarbonyl group is preferable. Similarly, $R^5$ in the general formulae [6], [7], [8], [12], [13], [14], [15] and [16] represent a hydrogen atom, a hydroxyl group or an acyloxy group, preferably a hydrogen atom or a hydroxyl group. And an acetoxy group, a propionyloxy group, a pivaloyloxy group and the like is exemplified as the above-mentioned acyloxy group. As to $R^6$ and $R^7$ in the general formula [8], (1) when $R^6$ represents a methyl group, $R^7$ represents a group shown by the formulae [2], [9] or [10] and (2) when $R^6$ represents a group shown by the formula [5] or [11], $R^7$ represents an acetyl group.

A compound having a group represented by the above-mentioned general formulae [1], [2], [4] or [5] and/or a group represented by the general formula [6] or [7] in the molecule as described above, preferably a compound represented by the above-mentioned general formula [8] and particularly a compound represented by the above-mentioned general formulae [12] to [16] can be obtained from the culture of *Penicillium* sp. SPF-3059 with the semaphorin inhibitory activity as an index. Moreover, such compound can also be obtained from the compound with semaphorin inhibitory activity thus obtained or the like by known converting and synthetic methods with the semaphorin inhibitory activity as an index. Compounds which constitute semaphorin inhibitors of the present invention are exemplified by those shown by the formulae [17]–[37] which are described later in the Examples in this description, and are more specifically exemplified by: the compounds represented by the general formula [12] which is shown by the formulae [17], [20], [23], [24] and [32]; the compounds represented by the general formula [13] shown by the formulae [18], [19], [21], [25], [26], [27] and [28]; the compounds represented by the general formula [14] shown by the formulae [22], [30], [31], [34], [36] and [37]; the compounds represented by the general formula [15] shown by the formulae [29] and [35]; and the compounds represented by the general formula [16] shown by the formula [33]. These compounds specifically exemplified in the above are novel compounds except for the following: the compound SPF-3059-1 shown by the formula [17] (Japanese Laid-Open Patent Application No. 1993-239050); the compound SPF-3059-2 shown by the formula [18] (Pure & Appl. Chem. 66, 2383–2386, 1994); and the compound SPF-3059-5 shown by the formula [19] (Pure & Appl. Chem. 66, 2383–2386, 1994, and Published Japanese translation of PCT international publication No. 1994-506202).

Further, in the compounds which constitute semaphorin inhibitors of the present invention, salts or derivatives of the compounds, preferably pharmaceutically or veterinary pharmaceutically acceptable salts or derivatives will also be included in the category of the present invention. The examples of salts are: inorganic basic salts such as sodium salt, potassium salt, calcium salt, magnesium salt, aluminum salt, ammonium salt or the like; organic basic salts such as triethylammonium salt, triethanolammonium salt, pyridinium salt, diisopropylammonium salt or the like; basic amino acid salts such as arginine salt, lysine salt or the like. The derivatives are exemplified those in which the carboxyl group or the hydroxyl group of a compound is converted to an ester group where the examples include a derivative in which the hydroxyl group is acylated by an acyl group with 2 to 5 carbons such as an acetyl group, a propionyl group or the like, and a derivative in which the carboxyl group is converted to esters with 2 to 5 carbons such as methylester, ethylester, or the like.

Examples of a compound of the present invention, preferably a compound having semaphorin inhibitory activity and particularly a compound obtained from the culture of *Penicillium* sp. SPF-3059 and having semaphorin inhibitory activity include a compound wherein at least one of $R^1$, $R^2$, $R^4$ and $R^5$ in the above-mentioned general formula [12] (wherein $R^1$, $R^2$, $R^4$ and $R^5$ are as described earlier) is represented by a hydrogen atom, preferably a compound wherein at least one of $R^2$ and $R^5$ represents a hydroxyl group, for instance, a compound in which $R^2$ represents a hydroxyl group (a compound in which $R^2$ and $R^5$ represent a hydroxyl group and a hydrogen atom, respectively, etc.), a compound in which $R^2$ and $R^5$ represent a hydroxyl group, the above-mentioned compound in which $R^4$ represents a carboxyl group and the above-mentioned compound in which $R^1$ and $R^4$ represent a carboxyl group and $R^2$ represents a hydroxyl group and the like. It is specifically exemplified by the compound SPF-3059-3 shown by the formula [20], the compound SPF-3059-7 shown by [23], the compound SPF-3059-9 shown by [24] and the compound SPF-3059-30 shown by [32]. Compounds of the present invention also include pharmaceutically acceptable salts or derivatives of the compound represented by the above-mentioned general formula [12].

Examples of a compound of the present invention, preferably a compound having semaphorin inhibitory activity, and particularly a compound obtained from the culture of *Penicillium* sp. SPF-3059 and having semaphorin inhibitory activity include a compound wherein at least one of $R^1$, $R^2$ and $R^5$ in the above-mentioned general formula [13] (wherein $R^1$, $R^2$, $R^4$ and $R^5$ are as described earlier) is represented by a hydrogen atom, preferably a compound wherein at least one of $R^2$ and $R^5$ represents a hydroxyl group, for instance, a compound in which $R^2$ represents a hydroxyl group (a compound in which $R^2$ and $R^5$ represent a hydroxyl group and a hydrogen atom, respectively, etc.), a compound in which $R^2$ and $R^5$ represent a hydroxyl group, the above-mentioned compound in which $R^4$ represents a carboxyl group and the above-mentioned compound in which $R^1$ and $R^4$ represent a carboxyl group and $R^5$ represents a hydroxyl group and the like. It is more specifically exemplified by the compound SPF-3059-4 shown by the formula [21], the compound SPF-3059-12 shown by [25], the compound SPF-3059-24 shown by [26], the compound SPF-3059-25 shown by [27] and the compound SPF-3059-26 shown by [28]. Compounds of the present invention also include pharmaceutically acceptable salts or derivatives of the compound represented by the above-mentioned general formula [13].

Examples of a compound of the present invention, preferably a compound having semaphorin inhibitory activity and particularly a compound obtained from the culture of *Penicillium* sp. SPF-3059 and having semaphorin inhibitory activity include a compound represented by the above-mentioned general formula [14] (wherein $R^1$, $R^2$, $R^3$, $R^4$ and $R^5$ are as described earlier), preferably a compound in which at least one of $R^2$ and $R^5$ is represented by a hydroxyl group, for instance, a compound in which $R^2$ represents a hydroxyl group (a compound in which $R^2$ and $R^5$ represent a hydroxyl group and a hydrogen atom, respectively, etc.), a compound in which $R^2$ and $R^5$ represent a hydroxyl group, the above-mentioned compound in which $R^4$ represents a carboxyl group, a compound in which $R^1$ and $R^4$ represent a carboxyl group and $R^2$ and $R^5$ represent a hydroxyl group, a compound in which $R^1$ represents a carboxyl group, $R^2$ and $R^5$ represent a hydroxyl group and $R^3$ represents methoxymethyl group, a compound in which $R^1$ represents either a carboxyl group or a methoxycarbonyl group, $R^4$ represents a carboxyl group, $R^3$ represents a hydrogen atom and $R^5$ represents a hydroxyl group, especially a compound in which $R^1$ represents either a carboxyl group or a methoxycarbonyl group, $R^4$ represents a carboxyl group, $R^2$ and $R^3$ represent a hydrogen atom and $R^5$ represents a hydroxyl group, a compound in which $R^3$ represents a group shown by the above-mentioned formula [3], and so on. It is more specifically exemplified by the compound SPF-3059-6 shown by the formula [22], the compound SPF-3059-28 shown by [30], the compound SPF-3059-29 shown by [31], the compound SPF-3059-35 shown by [34], the compound SPF-3059-37 shown by [36], and the compound SPF-3059-39 shown by [37]. Compounds of the present invention also include pharmaceutically acceptable salts or derivatives of the compound represented by the above-mentioned general formula [14].

Examples of a compound of the present invention, preferably a compound having semaphorin inhibitory activity, and particularly a compound obtained from the culture of *Penicillium* sp. SPF-3059 and having semaphorin inhibitory activity include a compound represented by the above-mentioned general formula [15] (wherein $R^4$ and $R^5$ are the same as described earlier), preferably a compound in which $R^5$ represents a hydroxyl group, the above-mentioned compound in which $R^4$ represents a carboxyl group and the like. It is more specifically exemplified by the compound SPF-3059-27 shown by the formula [29] and the compound SPF-3059-36 shown by [35]. Compounds of the present invention also include pharmaceutically acceptable salts or derivatives of the compound represented by the above-mentioned general formula [15].

Examples of a compound of the present invention, preferably a compound having semaphorin inhibitory activity, and particularly a compound obtained from the culture of *Penicillium* sp. SPF-3059 and having semaphorin inhibitory activity include a compound represented by the above-mentioned general formula [16] (wherein $R^1$, $R^2$, $R^4$ and $R^5$ are the same as described earlier), preferably a compound wherein at least one of $R^2$ and $R^5$ represents a hydroxyl group, especially a compound in which $R^2$ and $R^5$ represent a hydroxyl group, the above-mentioned compound in which $R^4$ represents a carboxyl group and the like. It is more specifically exemplified by the compound SPF-3059-34 shown by the formula [33]. Compounds of the present invention also include pharmaceutically acceptable salts or derivatives of the compound represented by the above-mentioned general formula [16].

A compound having a group represented by the above-mentioned general formulae [1], [2], [4] or [5] and/or a group represented by the above-mentioned general formula [6] or [7] in the molecule and having semaphorin inhibitory activity, preferably a compound represented by the above-mentioned general formula [8], more preferably a compound represented by the above-mentioned general formula [12] to [16], more specifically compounds constituting the semaphorin inhibitors of the present invention shown by the above-mentioned formulae [17] to [37], etc., all these compounds can be effectively obtained by cultivating the fungal strain SPF-3059 which belongs to the genus *Penicillium*. The strain was isolated by the present inventors from a soil sample collected in Osaka Prefecture, Japan. The strain SPF-3059 possesses the following taxonomical characteristics.

(a) Cultural and Morphological Characteristics

On malt extract agar, colonies grew slowly attaining a diameter of 2.8 to 2.9 cm in 21 days at 25.degree. C. The colonies were white to yellow and floccose in appearance. The reverse side color was dark yellow. Neither soluble pigment production nor spore formation was observed. On potato dextrose agar, colonies grew slowly attaining a diameter of 3.2 to 3.3 cm in 21 days at 25.degree. C. The colonies were white to cream yellow and floccose in appearance. The reverse side color was dark yellow to brown. Neither soluble pigment production nor spore formation was observed. On Czapek agar, colonies grew slowly attaining a diameter of 3.1 to 3.2 cm in 21 days at 25° C. The colonies were white to gray and floccose in appearance. The reverse side color was cream yellow. Neither soluble pigment production nor spore formation was observed. On oatmeal agar (Actino Medium No. 3 "DAIGO", Nihon Pharmaceutical Co., Ltd.), colonies grew slowly attaining a diameter of 2.0 to 2.1 cm in 21 days at 25.degree. C. The colonies were white to yellow or grayish green and floccose in appearance. The reverse side color was cream yellow to gray. Soluble pigment was not produced but spore formation was observed. The conidiophores were smooth-walled with a length of 5 to 20 μm, and generated 3 to 6 phialides in a monoverticillate manner at the end of the stipes. On the top of the phialides, which had a length of 3 to 4 μm, conidia were formed in a chain form, with 2 to 10 conidia per chain. The conidia are globose with a diameter of 2.2 to 2.4 μm with striated surface (in general, 10 longitudinal lines on the surface). Teleomorph was not observed.

(b) Physiological Characteristics (1) pH Range for Growth

Growth was examined in shaking culture using Sabouraud broth. Observation was made after cultivation for 3 days at 27.degree. C. The result was as follows:

| pH | Growth |
|---|---|
| 3.1 | − |
| 4.5 | + |
| 5.5 | ++ |
| 7.1 | +++ |
| 8.0 | ++ |
| 9.0 | + |
| 10.0 | − |

(2) Temperature Range for Growth

Growth was examined using oatmeal agar. Observation was made after incubation for 5 days at 38.degree. C. The result was that the strain grew at the temperature.

Based on the above taxonomical characteristics, the strain was identified as a strain of the genus *Penicillium* and was named *Penicillium* sp. SPF-3059. The said strain was deposited on Jul. 13, 2001 to the International Patent Organism Depositary, the National Institute of Advanced Industrial Science and Technology, Japan (1-1 Higashi 1-chome, Tsukuba, Ibaraki 305–8566, Japan) under the accession number FERM BP-7663 as the International Deposition Number under the Budapest Treaty on the international recognition of the deposit of microorganisms for the purpose of patent procedure.

According to the present invention, the cultivation for the production of the said semaphorin inhibitors by the strain SPF-3059 can be carried out in a nutrient medium. The nutrient medium may either be liquid or solid. Shaking culture or submerged culture with aeration is preferable. The composition of the medium may be varied over a wide range. No particular limitation is assigned to medium composition for use. Essentially, what is required is a carbon source, and a nitrogen source. Trace inorganic elements can also be added. Examples of suitable carbon sources are glucose, sucrose, glycerin, starch, dextrin, molasses or the like. Examples of suitable nitrogen sources are peptone, casein or its hydrolyzate, meat extract, yeast extract, soy bean flour, cotton seed flour, corn steep liquor, amino acids such as histidine, ammonium salts, nitrate salts or the like. Examples of sources of suitable inorganic elements are phosphate salts such as sodium phosphate and potassium phosphate, magnesium sulfate, sodium chloride, potassium chloride, calcium carbonate or the like. Inorganic elements can also be added to a medium to adjust osmotic pressure, adjust pH, supplement trace elements or the like. Moreover, various additives such as vitamins, nucleic acids or the like may be added to the medium for promoting the growth of the producing strain. It is also possible to add an antifoam agent such as silicon oil, polypropylene glycol derivative, soy bean oil or the like during the culture period. A preferred temperature range for the culture is preferably 20 to 35.degree. C., more preferably 25 to 30.degree. C., and preferable pH of the medium is, for instance, those ranging around neutral, and the culture period is, for instance, a span of 5 to 10 days.

For recovery of the semaphorin inhibitors of the present invention, shown by the above-mentioned formula [17] to [37], from the fermentation broth after the cultivation, there may be adopted any conventional methods as adopted for isolation and purification of secondary metabolites produced by microorganisms. These methods include solvent extraction, ion-exchange chromatography, adsorption chromatography, partition chromatography, gel filtration chromatography, high-performance liquid chromatography (HPLC), thin layer chromatography and the like. These isolation and purification methods may be adopted either alone or in combination. To obtain the object compounds from the culture supernatant, these isolation and purification method scan be adopted. In addition, when the object compounds are within the cultured fungal mycelium, the mycelium can be collected by the means of such as filtration or centrifugation and can be extracted directly by using a water-soluble organic solvent such as acetone, methanol or the like. Then a compound of interest can be obtained from the extract by the similar methods described above. Said compound of interest also can be converted to a salt by adding an appropriate amount of base in solvents such as water, methanol, ethanol, acetone, ethyl acetate, chloroform, ether or the like. Moreover, a hydroxyl group can be acylated, a carboxyl group can be esterificated in said compound of interest by the conventional methods. For instance, a hydroxyl group can be acylated by the addition of an acylation agent such as acetic anhydride, acetyl chloride or the like in an appropriate organic solvent and in the presence of bases. Alternatively, a carboxyl group can be esterificated by using alkyl halide such as methyl iodide, ethyl bromide or the like in an appropriate organic solvent and in the presence of bases. As for said organic solvents, acetone, ethyl acetate, chloroform, ether, DMF, pyridine or the like can be exemplified. As for bases, triethylamine, pyridine, potassium carbonate or the like can be exemplified.

Further, M162 or A721, which are described in the Examples, are also exemplified as other semaphorin inhibitors of the present invention. M162 is an aliphatic compound with a weak ultra violet adsorption, whereas A721 is a natural product isolated from the cultured broth of an actinomycete strain having a molecular weight of 437 and the maximum UV-visible absorption spectrum λ max (in methanol) at 397 nm. Considering these, M162 and A721 are low-molecular weight compounds whose chemical structures are totally different from those of the compounds shown by the above-mentioned formulae [17]–[37] and the like.

There is no specific limitation as to preventives or remedies of the present invention for neuropathic diseases and/or neurodegenerative diseases including spinal nerve injury and/or the peripheral nerve injury, as long as they contain the nerve regeneration promoters described earlier which have an inhibitor for a nerve outgrowth repelling factor, particularly the above-mentioned semaphorin inhibitors, as an active ingredient. To said preventives and remedies, various dispensing compositions may be added such as pharmaceutically acceptable ordinary carriers, binders, stabilizers, excipients, diluents, pH buffers, disintegrating agents, solubilizers, dissolving coadjuvants, isotonic agents or the like. Besides, these preventives and remedies can be administered either orally or parenterally. In other words, they can be administered in usual administration means, for example, they can be orally administered in agent forms such as powder, granule, capsule, syrup, suspension liquid or the like, or they can be parenterally administered by injecting in agent forms such as solution, emulsion, suspension or the like. Alternatively, they can be nasally administered in the form of spray agents.

Although dosage and frequency of administration differ depending on the method of administration and the age, weight, medical conditions or the like of a patient, it is preferable to locally administer to the site of disease. Since it takes several days to more than several months for nerves to regenerate, the preventives or the remedies are preferably administered once or more than twice during that period to suppress semaphorin activities. When administering twice or more, it is preferable to administer the preventives or the remedies repeatedly for consecutive days or at appropriate intervals. Dosage may be defined as several hundred µg to 2 g per administration in the form of a semaphorin inhibitor, preferably several dozen mg or less. In order to reduce the administration frequency, sustained release agents, an osmotic pump or the like may be used. In any of these administration methods, it is preferable to adopt an administration route and method wherein the concentration should reach the sufficient level to inhibit semaphorin activity at the site of action.

The above-mentioned neuropathic diseases and/or neurodegenerative diseases including spinal nerve injury and/or peripheral nerve injury means injury or degenerative diseases of peripheral or central nerves enumerated by: olfactory abnormality due to aging or the like; nerve injury other than the olfactory caused by trauma such as spinal cord injury or the like; nerve damage due to cerebral infarction or the like; facial nerve paralysis; diabetic neuropathy; glaucoma; retinitis pigmentosa;, neurodegenerative diseases such as Alzheimer's disease, Parkinson's disease and ALS; muscular hypoplastic lateral sclerosis; Lou Gehrig's disease; Huntington's chorea; cerebral infarction; traumatic neurodegenerative diseases; and so on. Diseases accompanied with angiogenesis in which VEGF165 is involved are also the targets, since VEGF165 also uses neuropilin as its receptor.

In addition, application of the nerve regeneration promoters of the present invention will not be limited to pharmaceuticals such as preventives or remedies for neuropathic diseases and/or neurodegenerative diseases, but are also capably applied to veterinary drugs, or further to industrially important experimental reagents as semaphorin signaling inhibitors. Because they contain semaphorin inhibitors as an active ingredient, nerve regeneration promoters of the present invention promote regeneration of olfactory nerve which is a peripheral nerve, and promote regeneration of nerves in the central region, which are olfactory bulb, cerebral cortex, hippocampus, corpus striatum, thalamus, diencephalon, mesencephalon, cerebellum, pons, medulla oblongata, spinal cord, retina and the like.

The present invention is now explained in detailed with the examples. The technical scope of the invention, however, will not be limited to these examples.

EXAMPLE 1

(Production of the Compounds, SPF-3059-1, SPF-3059-2, SPF-3059-5)

A 75 ml medium containing 2% glucose, 5% sucrose, 2% cotton seed powder, 0.1% sodium nitrate, 0.1% L-histidine, 0.05% dipotassium phosphate, 0.07% potassium chloride and 0.0014% magnesium sulfate heptahydrate, with its pH adjusted to 7.0, was pipetted to a Sakaguchi flask of 500 ml-volume and sterilized in an autoclave. A loopful of *Penicillium* sp. SPF-3059 (FERM BP-7663) on slant culture was inoculated into this medium and cultured with shaking at 130 rpm for 5 days at 27.degree. C. as the pre-culture. A medium with the same composition as the above-mentioned medium was pipetted 300 ml each to 10 Sakaguchi flasks of 2 liter-volume and sterilized in an autoclave. Subsequently, the above mentioned pre-culture solution was added to these flasks by 6 ml each, which were then cultured with shaking at 110 rmp for 7 days at 27.degree. C.

After the cultivation, the fermentation broth was centrifuged at 10,000 rpm for 10 minutes at 4.degree. C. to separate the supernatant and the mycelium. The supernatant fractions were extracted with a 3 L of ethyl acetate-formic acid (99:1). The mycelium fraction was extracted with 3 liters of acetone, then filtered and concentrated. After concentrated into aqueous solution, it was extracted with 1 liter of ethyl acetate-formic acid (99:1). Both extracts were then mixed and concentrated under reduced pressure to obtain a 10.4 g of crude extract. This extract was then dissolved into 100 ml of methanol and applied to a column chromatography with Sephadex (trade mark) LH-20 (Amersham Biosciences K.K.), and eluted with methanol. Active fractions were collected and the solvent was evaporated under reduced pressure to obtain 2.6 g of crude material. This crude material was then dissolved in 100 ml of methanol for a column chromatography using TSKgel TOYOPEARL HW-40F (Tosoh Corporation) and eluted with methanol. The active fractions were collected and the solvent was evaporated under reduced pressure to obtain 1.6 g of crude substance. This crude substance was then dissolved in 50 mg aliquots in 1 ml of dimethyl sulfoxide (DMSO) for a reversed-phase HPLC. The conditions of the reversed-phase HPLC were, column: Wakopak® Wakosil-II5C18RS (connecting 20×50 mm and 20×250 mm, Wako Pure Chemical Industries, Ltd.), solution A: 1% aqueous formic acid solution, solution B: methanol, gradient: a linear gradient for 90 min from 35% to 65% for the proportion of the solution B, flow rate: 5 ml/min, detection: absorbance at 260 nm. The eluted fractions at 59, 74 and 81 minutes were collected and the solvent was evaporated under reduced pressure, and thus the compounds, SPF-3059-5 (34.2 mg), SPF-3059-1 (64.1 mg) and SPF-3059-2 (12.0 mg) were obtained respectively. The physicochemical properties of these compounds thus obtained are as follows.

(Compound SPF-3059-1)

Appearance: yellow powder

High Resolution Fast Atom Bombardment Mass Spectrum (HRFAB-MS)m/z(M+H)$^+$: Measured value: 579.0772 Calculated value: 579.0776

Molecular formula: $C_{28}H_{18}O_{14}$

UV-VISIBLE Absorption Spectrum $\lambda_{max}$ (in methanol) nm(å): 241 (31,600), 315 (23,400), 365 (16,500)

Infrared Absorption Spectrum $\nu_{max}$ (KBr) cm$^{-1}$: 3400, 1701, 1615, 1570, 1457, 1273

$^1$H-NMR (500 MHz, DMSO-d$_6$) ä ppm: 2.28, 2.67, 2.69, 4.6–4.7, 5.02, 6.40, 6.91, 7.91, 8.52, 9.33, 11.1–11.6, 12.8

$^{13}$C-NMR (125 MHz, DMSO-d$_6$) δ ppm: 16.5, 17.0, 32.4, 56.2, 65.7, 68.0, 102.3, 104.2, 108.8, 110.1, 118.2, 118.5, 120.6, 122.2, 125.8, 127.7, 132.4, 134.9, 137.6, 139.1, 140.7, 140.8, 150.1, 150.2, 152.2, 153.8, 154.5, 156.3, 167.5, 167.6, 172.7, 172.8, 186.3, 199.1, 202.7, 202.9

Taken together, the structure of SPF-3059-1 was determined as the following formula [17] (tautomer):

[Chemical formula 32]

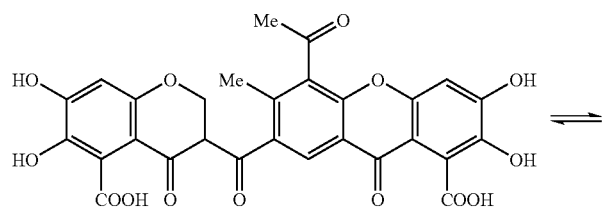

[17]

(Compound SPF-3059-2)

Appearance: cream-colored powder

High Resolution Fast Atom Bombardment Mass Spectrum (HRFAB-MS) m/z(M+H)$^+$: Measured value: 533.0710 Calculated value: 533.0721

Molecular formula: $C_{27}H_{16}O_{12}$

UV-VISIBLE Absorption Spectrum $\lambda_{max}$ (in methanol) nm(∈): 209 (40,600), 236 (42,600), 283 (28,500), 323 (25,400)

Infrared Absorption Spectrum $\nu_{max}$ (KBr) cm$^{-1}$: 3266, 1678, 1654, 1623, 1562, 1471, 1296

$^1$H-NMR (DMSO-d$_6$) δ ppm: 2.53 (6H, s), 6.93 (1H, s), 6.95 (1H, s), 7.47 (1H, s), 8.15 (1H, s), 8.54 (1H, s), 9.38 (1H, brs), 9.89 (1H, brs), 10.78 (1H, brs), 11.37 (1H, brs), 12.68 (1H, brs)

$^{13}$C-NMR (DMSO-d$_6$) δ ppm: 29.1, 32.1, 102.3, 103.1, 108.7, 112.5, 113.5, 119.6, 119.8, 120.9, 126.2, 132.4, 133.6, 136.1, 141.7, 144.5, 150.71, 150.74, 152.49, 152.54, 152.7, 154.4, 167.4, 172.9, 173.4, 199.2, 201.2

Taken together, the structure of SPF-3059-2 was determined as the following formula [18]:

[Chemical formula 33]

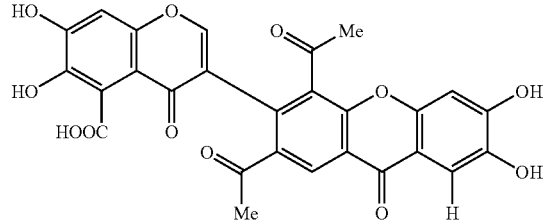

[18]

(Compound SPF-3059-5)

Appearance: cream-colored powder

High Resolution Fast Atom Bombardment Mass Spectrum (HRFAB-MS)m/z(M+H)$^+$: Measured value: 577.0615 Calculated value: 577.0619

Molecular formula: $C_{28}H_{16}O_{14}$

UV-VISIBLE Absorption Spectrum $\lambda_{max}$ (in methanol) nm(∈): 229 (35,800), 284 (22,600), 322 (21,000)

Infrared Absorption Spectrum $\nu_{max}$ (KBr) cm$^{-1}$: 3260, 1684, 1626, 1567, 1467, 1288

$^1$H-NMR (DMSO-d$_6$) δ ppm:
2.53 (3H, s), 2.55 (3H, s), 6.93 (1H, s), 6.96 (1H, s), 8.17 (1H, s), 8.53 (1H, s), 9.5–13.0 (6H)

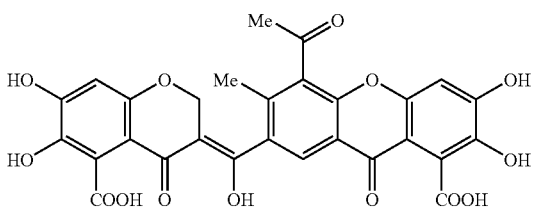

$^{13}$C-NMR (DMSO-d$_6$) δ ppm: 29.1, 32.1, 102.26, 102.32, 109.9, 112.4, 119.6, 119.8, 120.3, 120.9, 126.3, 132.5, 133.4, 136.2, 141.2, 141.7, 150.4, 150.8, 152.1, 152.68, 152.73, 154.5, 167.4, 167.5, 172.5, 172.9, 199.1, 201.1

From these results, the structure of SPF-3059-5 was determined as the following formula [19]:

[Chemical formula 34]

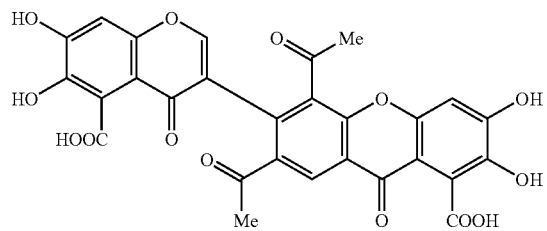

[19]

EXAMPLE 2

(Suppressing Action of the Compounds SPF-3059-1, SPF-3059-2, SPF-3059-5, M162 and A721 of the Present Invention to the Collapse Activity of Sema3A)

A 96-well plate (Sumitomo Bakelite Co., ltd.) pre-coated with polylysine was further coated with laminine (20 μg/ml of laminine, for 1 hour at room temperature). Each well was added with 100 μl of medium (F12 medium containing 10% bovine fetal serum, 20 ng/ml of NGF, 100 units/ml of penicillin and 100 μg/ml of streptomycin) which media were then inoculated with dorsal root nerve ganglions excised from E7 (Embryonic day 7) chick embryo and were cultured for 16 to 20 hours under 5% $CO_2$ and at 37.degree. C. Subsequently, the object compounds were added to media at various concentrations and 2 units/ml of mouse semaphorin 3A (Sema3A) was added after cultivating for 1 hour. The cultures were further incubated for another 1 hour. Glutaraldehyde was quickly added therein after said 1 hour to make the final concentration 1%. The cultures were then left for 15 minutes at room temperature so that the tissue sections were fixed, and collapse rates of the growth cones were microscopically observed. A well with no addition of Sema3A was made the control. The results are shown in FIGS. 1 and 2.

Figure 2:
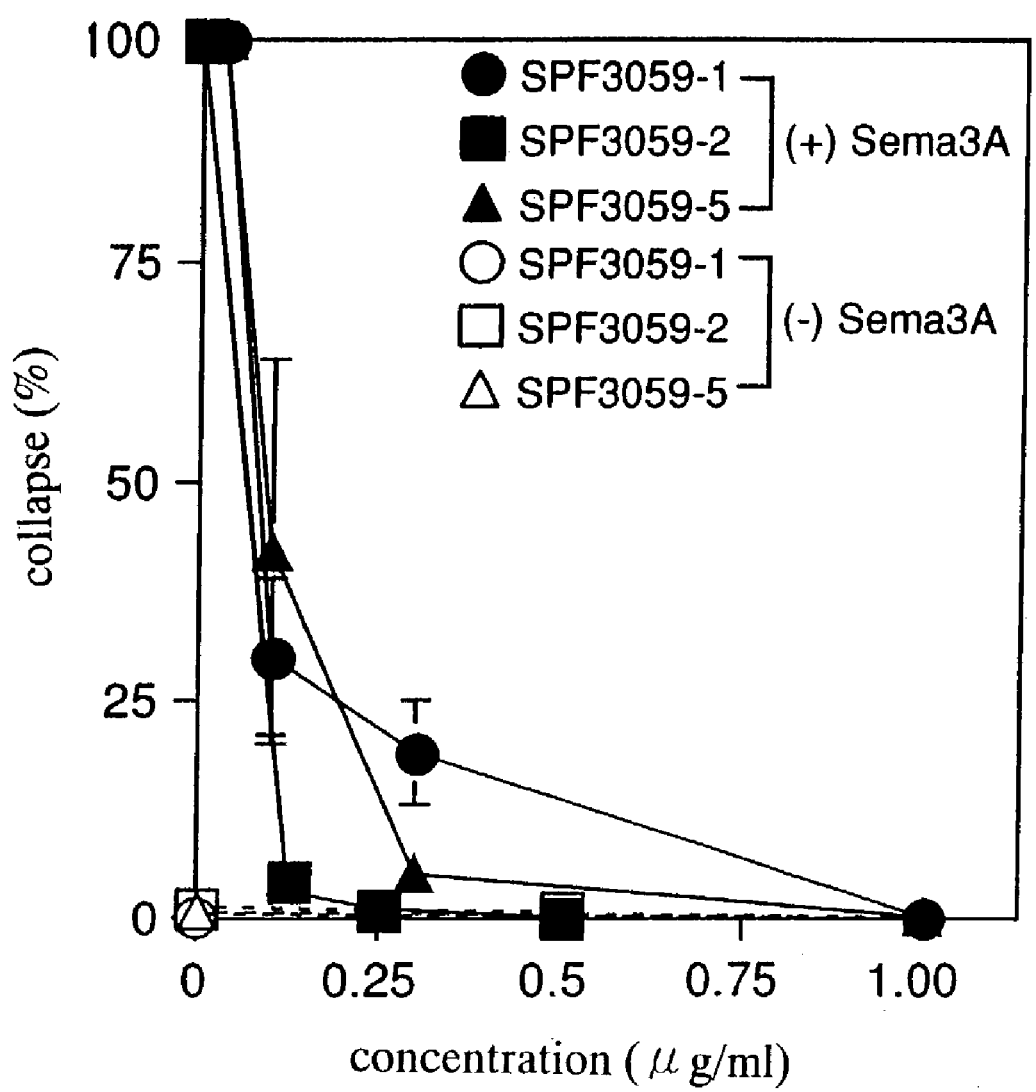
FIG. 2 shows the concentration-dependent inhibitory action of the semaphorin inhibitors of the present invention, SPF-3059-1, SPF-3059-2 and SPF-3059-5, on the growth cone collapse activity of Sema3A.

FIGS. 1 and 2 show that the collapse rate of the growth cones decrease as the compound concentration increase. On the contrary, compounds alone did not affect the rates at all. The results revealed that these compounds (SPF-3059-1, SPF-3059-2, SPF-3059-5, M162 and A721) inhibit the growth cone collapse activities of Sema3A in a concentration-dependent manner. The longitudinal and lateral axes in the figures represent the collapse rate of growth cones and the concentration of compounds, respectively. ●■▲ show the results when Sema3A was added after the addition of the compounds and ○□△ show those when Sema3A was not added. Further, IC50 (μg/ml) of the inhibitors were determined by the method comprising: calculating the collapse rate of growth cone (A)% of the negative controls (neither compounds nor Sema3a was added); subsequently calculate the collapse rate of growth cone (B)% of the positive controls (compounds were not added but Sema3a was added); and the concentration was chosen for each compound from the chart where the collapse rate of growth cone met (A+B)/2 (%), which was made IC50 level. The followings are the results.

| Compound | IC50 (μg/ml) |
|---|---|
| SPF-3059-1 | <0.1 |
| SPF-3059-2 | <0.1 |
| SPF-3059-5 | <0.1 |
| M162 | 2.0 |
| A721 | 5.0 |

These results show that SPF-3059-1, SPF-3059-2 and SPF-3059-5 potently inhibit semaphorin.

EXAMPLE 3

(Suppressing Action of SPF-3059-1 to the Collapse Activity of Sema6C)

Figure 3:
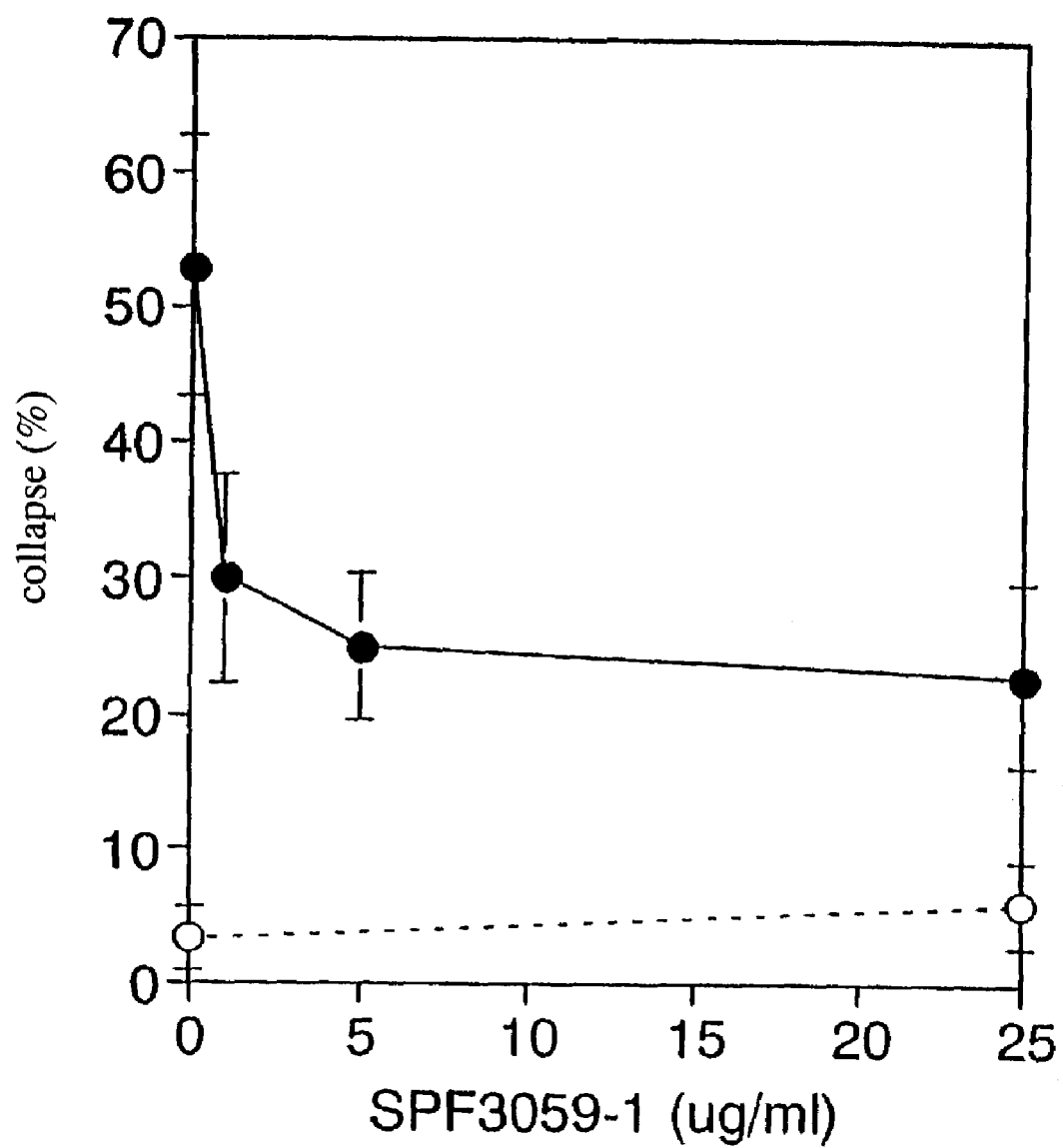
FIG. 3 shows the concentration-dependent inhibitory action of the semaphorin inhibitor SPF-3059-1 of the present invention on the growth cone collapse activity of Sema6C.

The experiment was carried out in a same way as in Example 2 except that rat semaphorin 6C-AP (Sema6C-AP: a fusion protein of extracellular domain of Sema6C and human placenta-derived alkaline phosphatase) was used instead of mouse semaphorin 3A (Sema3A), and dorsal root ganglions excised from 8-day-old chick embryos were used instead of those excised from 7-day-old chick embryos. The collapse rate of growth cone was measured when Sema6C-AP was added one hour after the addition of the compound SPF-3059-1 at various concentrations. The results are shown in FIG. 3. The longitudinal and lateral axes in the figure represent the collapse rate of growth cones and the concentration of SPF-3059-1, respectively. ● shows the result when Sema6C-AP was added after the addition of SPF-3059-1 and shows the result when Sema6C-AP was not added. FIG. 3 shows that the collapse rate of the growth cones decrease as the SPF-3059-1 concentration increased. On the contrary, SPF-3059-1 alone did not affect the rate at all. These results revealed that SPF-3059-1 inhibit the growth cone collapse activities of Sema6C-AP in a concentration-dependent manner.

EXAMPLE 4

(Suppression of Neurite Outgrowth Inhibitory Action of Sema3A by the Inhibitors)

Figure 4:
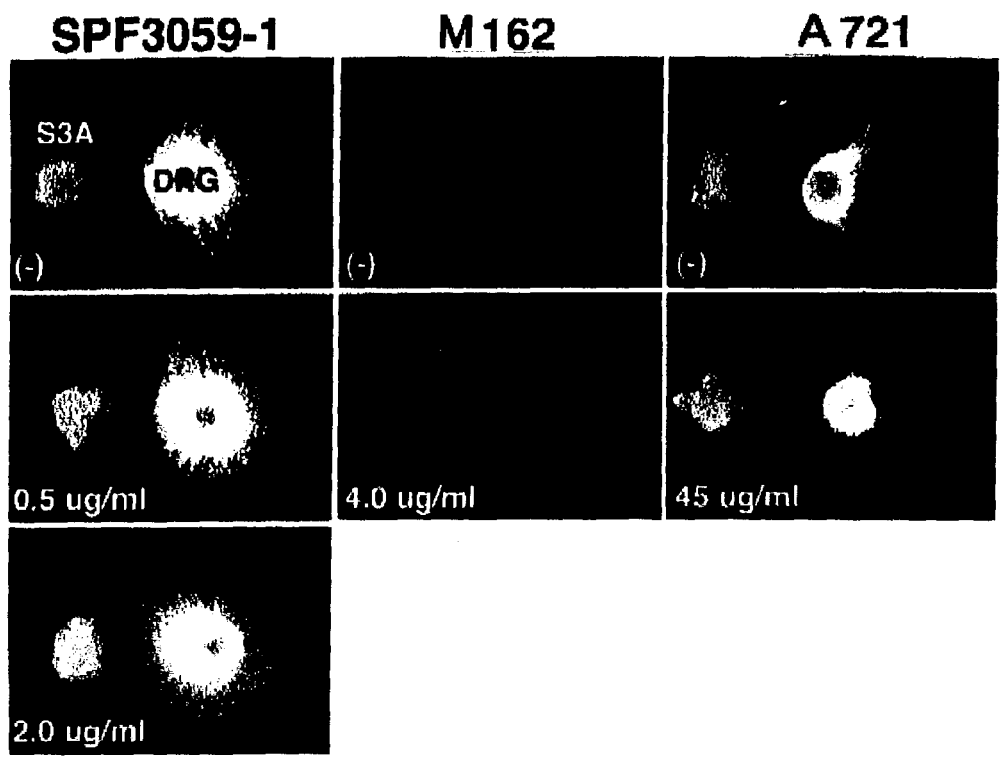
FIG. 4 is photographs showing inhibitory action of the semaphorin inhibitors of the present invention, SPF-3059-1, M162 and A721, on the neurite outgrowth inhibitory activity of Sema3A in the collagen-gel co-culture method.
Figure 4:
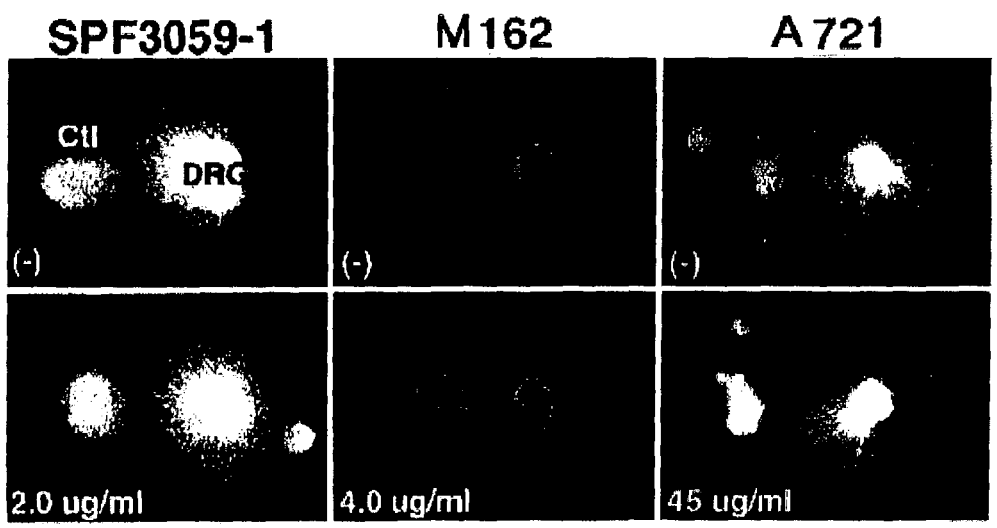

Whether the object compounds (SPF-3059-1, M162, A721) have persistent inhibitory action to Sema3A was analyzed by the collagen gel co-culture method (Neuroprotocols 4, 116, 1994) using Sema3A-expressing COS7 cell clumps and 7- or 8-day-old chick embryo dorsal root ganglions. The Sema3A-expressing COS7 cell clumps were generated as follows. 1 μg of Sema3A-expression plasmid was introduced into COS7 cells (100000 cells/35 mm culture plate), which were cultured overnight, with the FuGENE6 transfection reagent (Roche). 2.5 hours after the starting of the transfection, the COS7 cells were collected by trypsinization and centrifugation, and re-suspended in a medium of 200 μl. 20 μl of the cell suspension was placed on the lid of the culture plate (inside) and the lid was turned over, and then the suspension was cultivated for 20 hours (hanging drop culture) (Cell 78, 425, 1994). When the culture was over, aggregated COS7 cells (clump) were collected and trimmed to a diameter of 0.5 mm. The Sema3A-expressing COS7 cell clump and the above-mentioned dorsal root ganglions were placed in parallel at a distance of 0.5 to 1 mm in a 0.2% collagen gel which was then cultivated in a medium containing the aforementioned compounds at various concentrations for 2 days at 37.degree. C. under 5% $CO_2$. Glutaraldehyde was quickly added therein to make the final concentration 1%. The cultures were then left for 1 hour at room temperature so that the tissues were fixed, and the neurite outgrowth was microscopically observed. The results are found in FIG. 4.

The concentration gradients were formed in the above-mentioned collagen gels because Sema3A was secreted from the COS7 cell clump which was introduced with the Sema3A-expressing plasmids (The one nearer to the COS7 cell clump had a higher concentration). When a medium not containing a subject compound was used, neurites were unable to grow towards the COS7 cell clump with the high concentration of Sema3A and grew only to the opposite direction. However, when the compound SPF-3059-1 or M162 was added to the medium, neurite outgrowth was observed to the direction toward the Sema3A-expressing COS7 cell clump. Such neurite outgrowth toward the Sema3A-expressing COS7 cell clump was more remarkable as the compound concentration was higher, suggesting the concentration-dependency. This result showed the ability of SPF-3059-1 and M162 to persistently inhibit Sema3A activities. However, only when A721 was added, neurite outgrowth toward the Sema3A-expressing COS7 cell clump, which was observed with the addition of SPF-3059-1 and M162, was not observed. This showed that A721 did not have the persisting inhibitory action on Sema3A.

EXAMPLE 5

(Suppression of Neurite Outgrowth Inhibitory Action of Sema3A)

In a similar way as in Example 4, suppression of the neurite outgrowth inhibitory activity was analyzed for the compounds, SPF-3059-1, SPF-3059-2 and SPF-3059-5. When the neurites outgrew in a complete concentric circular shape just like for the control groups where Sema3A-non-expressing COS7 cells were used, it was scored +++ (a strong inhibitory effect for Sema3A). When the outgrowth was found almost in a concentric circular shape accompanied with a little suppression of the outgrowth toward the direction of Sema3A-expressing COS cells, it was scored ++. When the outgrowth toward the direction of Sema3A-expressing COS cells is fairly suppressed to present a crescent shape, it was scored +. When the outgrowth toward the direction of Sema3A-expressing COS cells was not found at all (no inhibitory effect for Sema3A), it was scored –. The determined results are shown below.

| Compound | Concentration of the subject compounds (µg/ml) | | |
|---|---|---|---|
| | 0.5 | 1.0 | 2.0 |
| SPF-3059-1 | + | ++ | +++ |
| SPF-3059-2 | + | ++ | +++ |
| SPF-3059-5 | + | ++ | +++ |
| PBS (control) | – | – | – |

These results revealed that the compounds, SPF-3059-1, SPF-3059-2 and SPF-3059-5 persistently inhibited the action of Sema3A secreted from the Sema3A-expressing COS7 cells during the 48-hour culture.

EXAMPLE 6

(In vivo Nerve-Regeneration Promoting Action of the Semaphorin Inhibitor SPF-3059-1 in the Olfactory Nerve Axotomy)

Male Wister rats (6.5-week-old) were purchased from CHARLES RIVER JAPAN, INC. and bred under free feeding and water uptake in the dedicated breeding room. A sample solution was prepared by diluting SPF-3059-1 to 1 mg/ml with PBS and filled in an osmotic pressure pump (alzet 2004, ALZA co., USA). A pump filled with PBS was used as a control. The sample solution and the like were prepared on the day before the operation and the osmotic pressure pump was bathed in PBS and placed overnight at room temperature. Just before the operation, a L-cannula was connected to the one end of a silicon tube filled with the sample solution and the like, and the other end of the tube was connected to the pump. A rat was anesthetized with pentbarbital (50 mg/kg, intrapenitrially injected), and its head was fixed to the stereotaxic apparatus. The scalp was incised along the median and the cranium above the olfactory bulb was opened to expose the olfactory bulb (anterior part). In order to axotomize olfactory nerve, a knife (a razor was cut into 1.5 mm width) was inserted in between the olfactory bulb and the cribriform plate. The olfactory nerve which is projected on the upper olfactory bulb is axotomized by this handling. The L-cannula was fixed to the cranium-opening above the olfactory with surgical instant adhesive and dental cement so that the edge of cannula is located in the vicinity of the incision. The sample output was set to 6 µl (6 µg)/day. The pump was subcutaneously inserted in the dorsal neck and the incision was sutured. Then the animal was recovered.

Two and three weeks after the operation, the rat anesthetized with pentbarbital was laid on its back and injected with 100 µl of 1% WGA-HRP/PBS (TOYOBO) into the nasal cavity using a microsyringe. 24 hours after the HRP injection, the rat was further anesthetized with pentbarbital (50 mg/kg, intrapenitrially injected) and was thoracically incised. Subsequently, PBS was perfused from the left ventricle and then PBS containing 200 ml of 4% paraformaldehyde was perfused. The olfactory bulb was excised and placed in PBS containing 30% sucrose, was bathed therein overnight at 4. degree. C., and was then frozen up with dry ice. The olfactory bulb was embedded in an OTC compound on dry ice and then 30 µm sections were prepared with a cryostat. The sections were aliquoted in Tris-buffered saline (TBS) (one in every three pieces). The sections were washed in TBS where a 0.1 M TBS containing 0.48% DAB, 0.096% NiCl and 0.036% $H_2O$ was then added and reaction took place for 15 min. After having been washed in TBS, the sections were mounted on a glass slide and sealed after they were dried. The sections were microscopically observed and HRP reaction of the glomerulus at the outer portion of olfactory bulb was observed.

Figure 5:
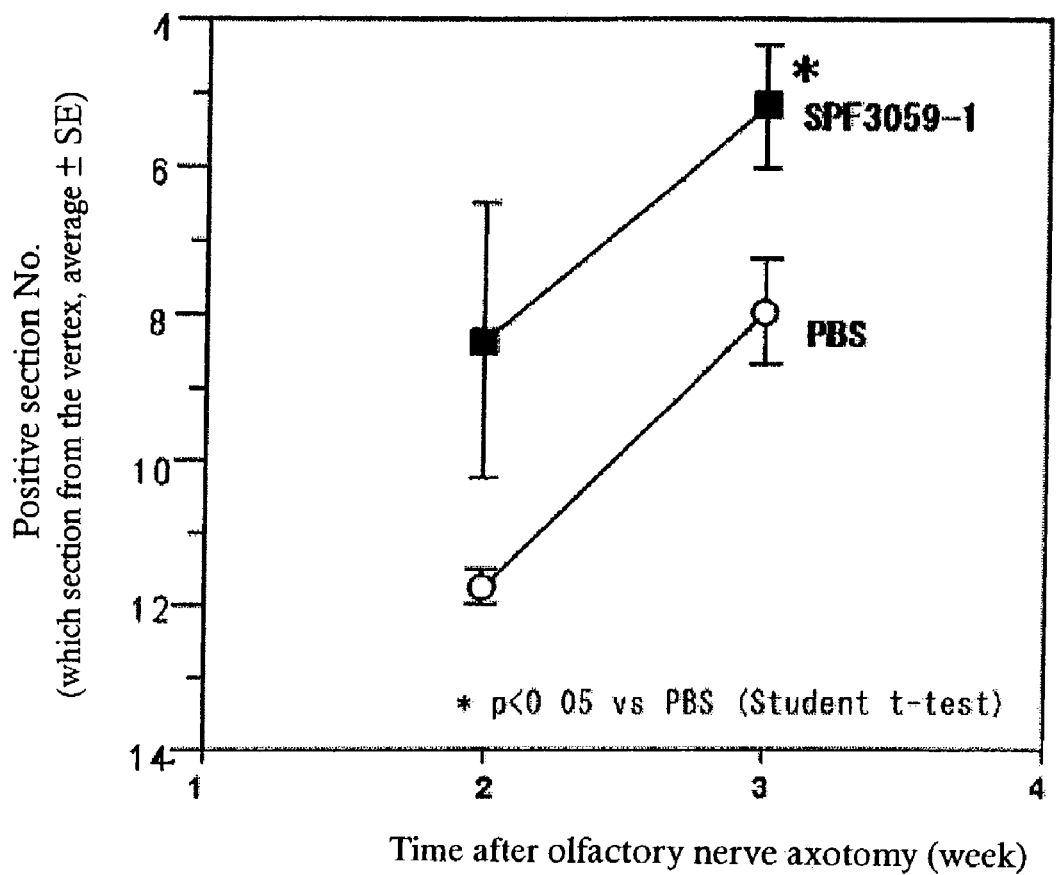
FIG. 5 shows the in vivo nerve-regeneration promoting action of the semaphorin inhibitor SPF-3059-1 of the present invention in the olfactory nerve incision.

Regeneration of olfactory nerves was quantitatively assessed by observing in which horizontal section of the olfactory bulb from the vertex did HRP-positive glomerulus emerge. The results are shown in FIG. 5 and Table 1. All the rats except the one which died from suffocation on Week 2 at the HRP injection were used for the assessment. When SPF-3059-1 was injected, HRP-positive sections were found in shallower pieces than the controls injected with PBS at both Weeks 2 and 3. The significant differences were judged in the SPF-3059-1-injected group against the PBS-injected group, the HRP-positives were found in the shallower sections than the PBS-injected group at Week 3. These results show that SPF-3059-1 has marked nerve-regeneration promoting action in the adult rat models for olfactory nerve axotomy.

TABLE 1

| Agent | Positive section No. (which section from the vertex, average ± SE) | Number of rats |
|---|---|---|
| Week 2 PBS | 11.8 ± 0.3 | 4 |
| Week 2 SPF3059-1 | 8.3 ± 1.9 | 3 |
| Week 3 PBS | 8.0 ± 1.4 | 4 |
| Week 3 SPF3059-1 | 5.2 ± 1.9* | 5 |

*$p < 0.05$ vs PBS Student t-test

EXAMPLE 7

(In vivo Nerve-Regeneration Promoting Action of the Semaphorin Inhibitors, M162 and A721 in the Olfactory Nerve Axotomy)

Figure 6:
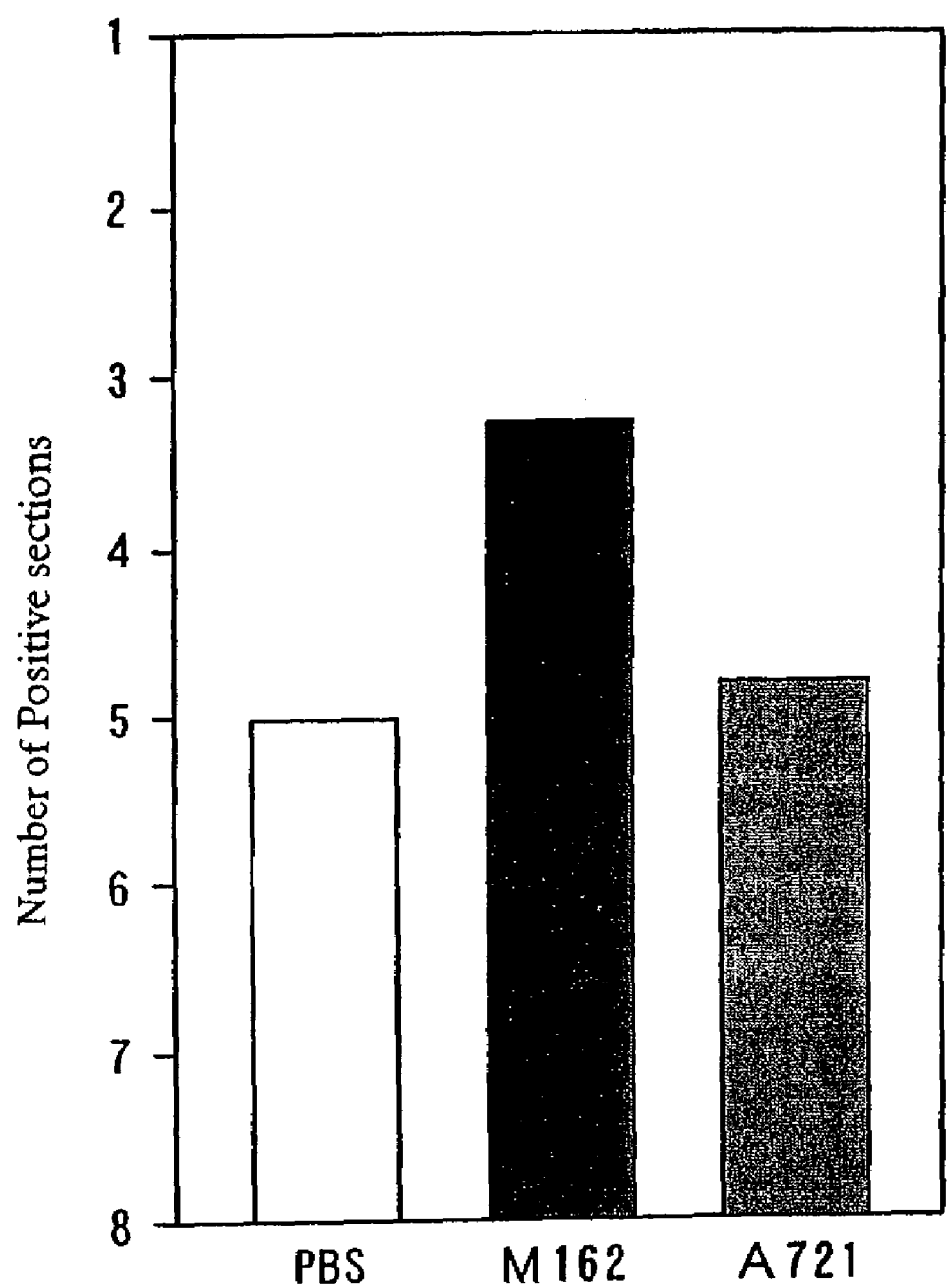
FIG. 6 shows the in vivo nerve-regeneration promoting action of the semaphorin inhibitors M162 and A721 of the present invention in the olfactory nerve incision.

The same experiment as in Example 6 was carried out with M162 and A721. The results are shown in FIG. 6. These results show that M162 has the in vivo nerve-regeneration promoting action but A721 does not.

EXAMPLE 8

(In vivo Nerve-Regeneration Promoting Action of the Semaphorin Inhibitor SPF-3059-1 in the Sciatic Nerve Crush)

Figure 7:
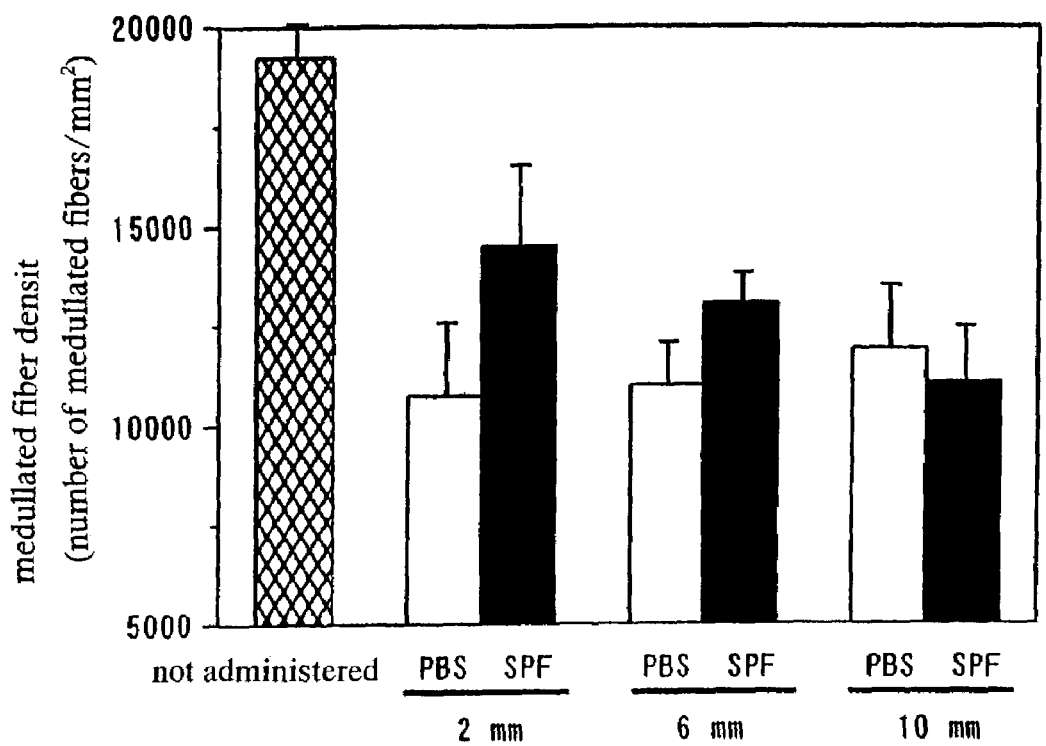
FIG. 7 shows the nerve-regeneration promoting action of the semaphorin inhibitor SPF-3059-1 of the present invention in the sciatic nerve wound.

Male Wister rats were purchased at 7-week-old (CHARLES RIVER JAPAN, INC.) and bred under the light and dark cycles for 12 hours. The rats had free access to solid feedstuff (CLEA Japan, Inc., CE2) and water, and were used in the experiment after about one week of preliminary breeding. Under pentbarbital anesthesia, sciatic nerve of the rat thighs was exposed, clipped for 30 sec with forceps of 5 mm width, and was thus crushed. The crush site was marked with 10-0 nylon thread. SPF-3059-1 was dissolved in PBS at 8.3 ug/ml and was locally administered to the lesion site for 14 consecutive days at a flow rate of 1 ug/day by using an osmotic pressure pump (2ML2, 5 ul/hr, alzet). PBS was administered to the controls. At Day 14 of administration, the sciatic nerves were excised and trimmed at the distal areas from the crush site (the positions of marking) by 2 mm, 6 mm and 10 mm. The incised sciatic nerves were fixed in 2.5% glutaraldehyde/0.1 M phosphate buffer for a day and a night. When they were fixed, nerves were dehydrated by alcohol and were embedded in epoxy resin. The transverse sections of the sciatic nerves were made and dyed with toluidine-blue, and their photographs were taken under an optical microscope to determine the counts of myelinated fibers. After the areas of sciatic nerves were measured, the myelinated fiber density was calculated by dividing each area by the count of myelinated fibers. The results are shown in FIG. 7. The myelinated fiber density was increased more in the SPF-3059-1-injected group compared to that of the PBS-injected group at the distal areas of 2 mm and 6 mm from the crush site. This result shows that SPF-3059-1 has the promoting effect for the regeneration of sciatic nerves that were crushed.

EXAMPLE 9

(Effect of the Semaphorin Inhibitor SPF-3059-1 On Cell Proliferation)

Figure 8:
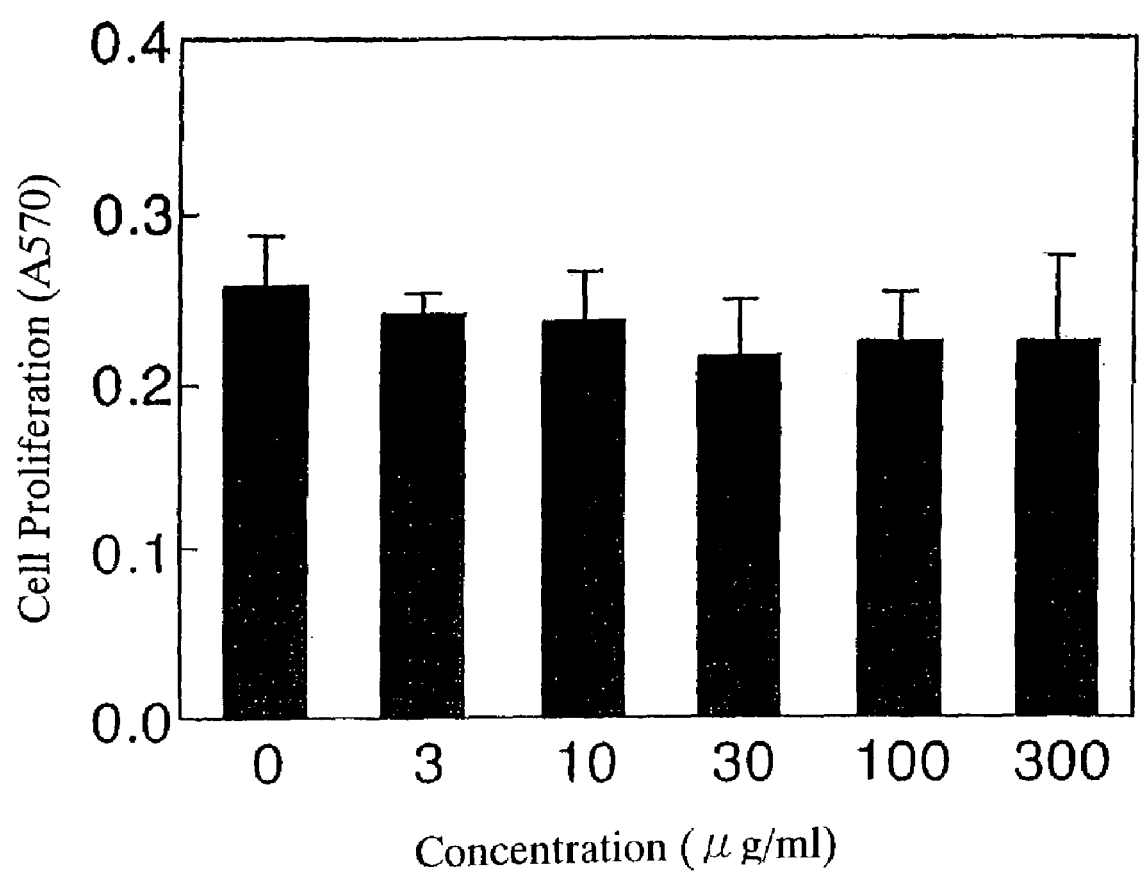
FIG. 8 shows the result of examining influence of the semaphorin inhibitor SPF-3059-1 of the present invention on the proliferation of COS7 cells.

COS7 cells were seeded onto a 96-well plate (medium 100 μl/well) at 10000 cells per well. At the same time, SPF-3059-1 of various concentrations was added and the cells were cultivated for two days in the presence of 5% $CO_2$ at 37.degree. C. Each well was then added with 10 μl of MTT solution at 5 mg/ml and cultured for another one hour. Subsequently, the culture supernatant was removed and formazan (an MTT derivative produced inviable cells) accumulated in the cells was dissolved by the addition of 50 μl DMSO and then the absorbance at 570 nm was measured to determine the proliferation of COS7 cells. The results are shown in FIG. 8. As shown in FIG. 8, the level of cell proliferation in the culture carried out in the presence of SPF-3059-1 was similar to the level observed in the absence of SPF-3059-1. This result shows that SPF-3059-1 has no suppressing activity for cell proliferation. The longitudinal and lateral axes in the figure show cell proliferation and the SPF-3059-1 concentration, respectively. Besides, the standard deviation (n=4) was added to each column.

EXAMPLE 10

(Effects of the Semaphorin Inhibitors SPF-3059-1, SPF-3059-2 and SPF-3059-5 on Cell Proliferation)

The same effect on cell proliferation as in Example 9 was examined for the compounds, SPF-3059-1, SPF-3059-2 and SPF-3059-5. The wells with these compounds were served as samples, the wells with PBS were served as control, and the wells for which the experiment was carried out without adding the cells was served as blank. IC50 (μg/ml), the inhibitory rate for cell proliferation, was determined, which is calculated by the equation shown below.

The inhibitory rate for cell proliferation (%)=(1−(absorbance of a sample well−absorbance of the blank well)/(absorbance of the control well−absorbance of the blank well))×100

The determination results of the inhibitory rate for cell proliferation of the above-mentioned compounds are as follows, showing that no cytotoxicity was observed at 1000 to 3000 folds or even higher concentrations in which semaphorin inhibitory activities can be observed.

| Compound | IC50 (μg/ml) |
| --- | --- |
| SPF-3059-1 | >300 |
| SPF-3059-2 | >100 |
| SPF-3059-5 | >300 |

EXAMPLE 11

(Inhibitory Activity of Sema3A-receptor-binding)

Whether SPF-3059-1 inhibits the binding of Sema3A and Neuropilin-1, which is a component constituting Sema3A receptor complex, was examined in the receptor-binding experiment. Neuropilin-1 and plexin A1 are currently known as constituting components of Sema3A receptors. However, mainly Neuropilin-1 is known to contribute to Sema3A binding. Sema3A fused with alkaline phosphatase (human-derived: heat-resistance) (Sema3A-AP) was used as a ligand in the receptor-binding experiment and the amount bound to the receptor was detected with the alkaline phosphatase activity as an index. Mouse-derived Sema3A was used. A recombinant gene was generated in which alkaline phosphatase was fused from the 758th amino acid to the C terminal side in said Sema3A. This recombinant gene was then introduced into a COS7 cell where it was expressed and secreted and Sema3A-AP was prepared.

The receptor-binding experiment was performed as described below. The Neuropilin-1 expressing plasmid (pUCSRα-Neuropilin-1) was introduced into COS7 cells and cultivated for 24 hours. These cells express Neuropilin-1 on the cell surface. The cells were washed once in HBH buffer solution (Hank's balanced salt solution containing 20 mM HEPES, pH 7.2, and 0.5 mg/ml bovine serum albumin) and then HBH buffer solution containing Sema3A-AP, and SPF-3059-1 of various concentrations (0 to 10 μg/ml) were added at the same time. After having been left for one hour at room temperature while being shaken, Sema3A-AP was bound to Neuropilin-1 expressing cells, after which the supernatant was removed. Subsequently, the cells were washed six times in HBH buffer solution to remove the excess Sema3A-AP. Thereafter Sema3A-AP bound to the cells was solubilized with 10 mM Tris-HCl, pH 8.0, 1%

Figure 9:
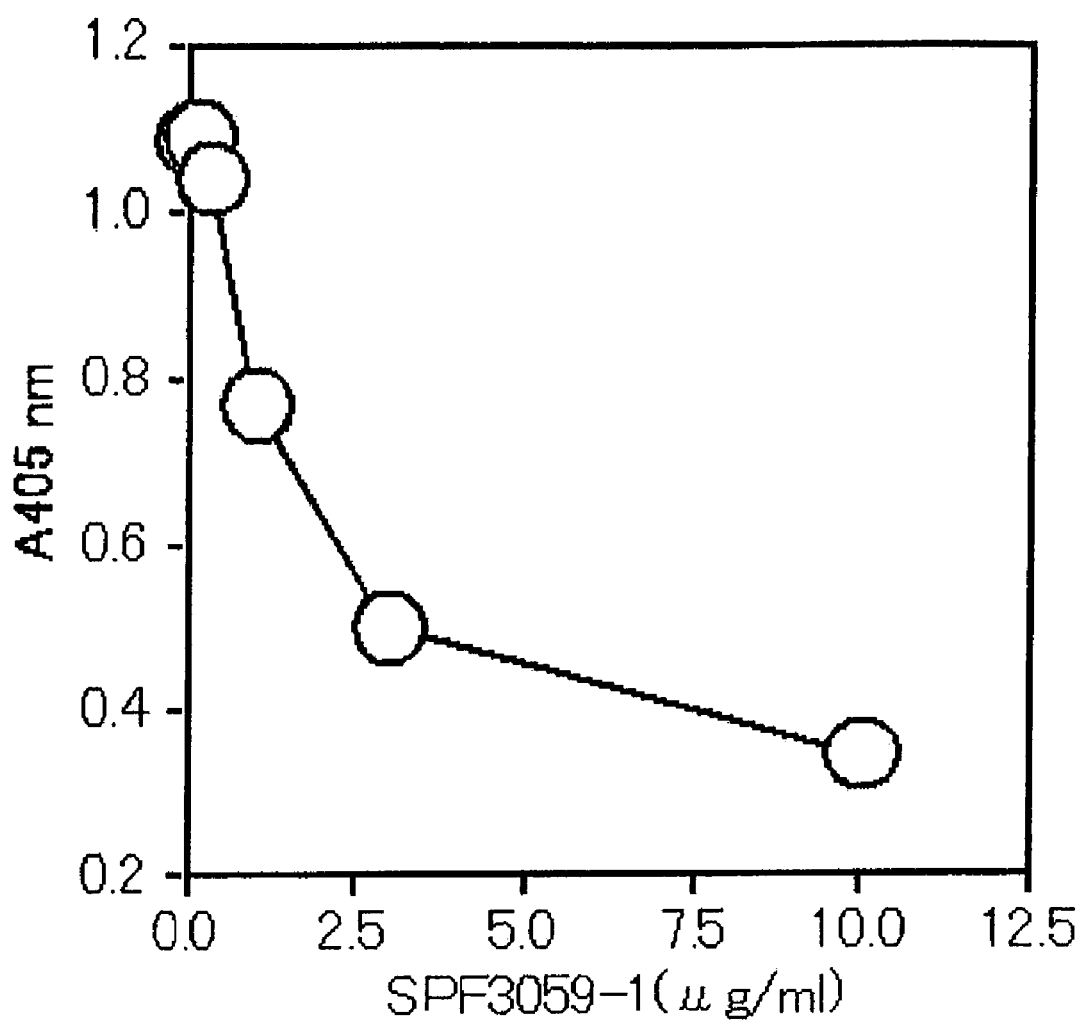
FIG. 9 shows the result of examining influence of the semaphorin inhibitor SPF-3059-1 of the present invention on the semaphorin 3A receptor (Neuropilin-1) binding.

Triton X-100 solution (the cell extract). Insoluble materials in the cell extract was removed by centrifugation and then endogenous alkaline phosphatase of the cell per se was inactivated after the treatment for one hour at 65.degree. C. The alkaline phosphatase activity derived from Sema3A-AP in the cell extract (=binding amount of Sema3A-AP) was determined. An aliquote of the cell extract was admixed with SEAP buffer (1M diethanolamine, 0.5 mM $MgCl_2$ 10 mM L-homoarginine) and a fluorescent substrate (10 mM p-nitirophenyl phosphate), and kept warm at 37.degree. C. The solution was then measured for its absorbance at 405 nm (p-nitrophenol: generated from p-nitirophenyl phosphate with alkaline phosphatase). The results are shown in FIG. 9. The results show that the binding of Sema3A-AP decrease in a concentration-dependent manner with increasing concentration of SPF-3059-1. This clearly shows that SPF-3059-1 inhibits the Sema3A activity because the compound inhibits the binding of Sema3A to its receptor.

EXAMPLE 12

(Inhibition of Collapse Activity by the Contact of Sema3A and the Inhibitor)

Figure 10:
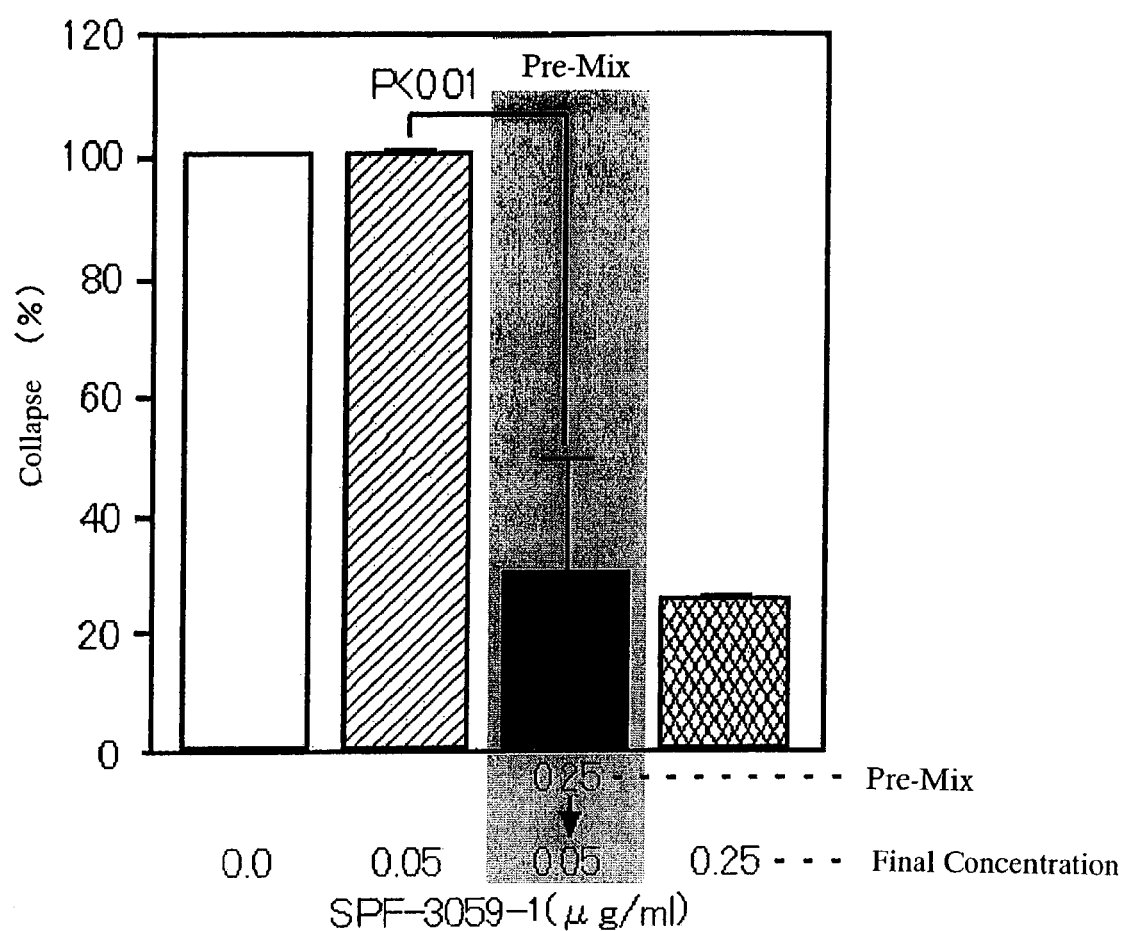
FIG. 10 shows the result of examining that the target molecule of the semaphorin inhibitor SPF-3059-1 of the present invention is semaphorin 3A.

Sema3A was mixed with SPF-3059-1, which concentration was high enough to show the inhibitory activity (0.25 µg/ml) (=Pre-Mix sample). Thereafter the Pre-Mix sample was added to the culture solution of dorsal root ganglions to examine whether the growth cone collapse activity of Sema3A was inhibited. The amount of Pre-Mix sample was a quarter of that of the culture solution. This means that the SPF-3059-1 concentration will be diluted from 0.25 µg/ml to 0.05 µg/ml (⅕fold) when the Pre-Mix sample is added to the culture solution of dorsal root ganglions. This is the concentration where the inhibitory activity will not be observed when SPF-3059-1 and Sema3A are independently added. The results are shown in FIG. 10. FIG. 10 shows that Sema3A activity was inhibited when the Pre-Mix sample was added to the culture solution of dorsal root ganglions in spite of the fact that the final concentration of SPF-3059-1 was 0.05 µg/ml (concentration of no-inhibitory activity). This means that the activity of Sema3A will be lost at the moment when Sema3A and SPF-3059-1 come in contact. From this result, the target molecule of SPF-3059-1 is thought to be Sema3A.

EXAMPLE 13

(In vivo Nerve-Regeneration Promoting Action of the Semaphorin Inhibitor SPF-3059-1 in the Transaction of the Spinal Nerve (Cerebral Cortex-spinal Cord Tract)

Male Wister rats (10-week-old) were purchased from Charles River Japan, Inc. and bred under free feeding and water uptake in a dedicated breeding room. They were used in the experiment after about one week of pre-breeding. SPF-3059-1 was prepared to 0.1 mg/ml with PBS. PBS was used as a control. The agent was filled in an osmotic pressure pump (Alzet, model 2004, dosage for four weeks, flow rate 0.25 µl/hr). A cannula filled with the sample solution etc. was connected to the pump and pre-incubated in saline overnight at room temperature.

A rat was intrapenitrially injected with pentbarbital (50 mg/kg). Skin and muscles in dorsal thoracic spinal cord region of the anesthetized rat were incised and the T8-T12 vertebras were exposed. Laminectomy was carried out for the T11 thoracic vertebra under the microscope. A pair of ophthalmologic scissors attached to the manipulator was punctured and inserted across the median line into the depth of 1.5 mm from the duramater surface, and the cerebral cortex-spinal cord pathway was incised and separated. The vertebra opening was filled with a spongel. Cannulation was performed from the T9 vertebra which was perforated with a surgical drill to expose the duramater. The part of the duramater, to which a cannula was to be inserted, was perforated with an injection needle and the silicon tube connected with the pump was inserted therein. It was made sure that the edge of the cannula reached to the T11 spinal cord injured area. Then a spongel was filled in the vertebra opening where a drop of surgical instant adhesive was infiltrated. The cannula was fixed to the adjacent muscle with suture to prevent slipping off. After suturing the muscle operated, the incised skin was stitched together with suture clamps. The sample was administered for four consecutive weeks with the sample flow rate of 0.6 µg/day.

Figure 11:
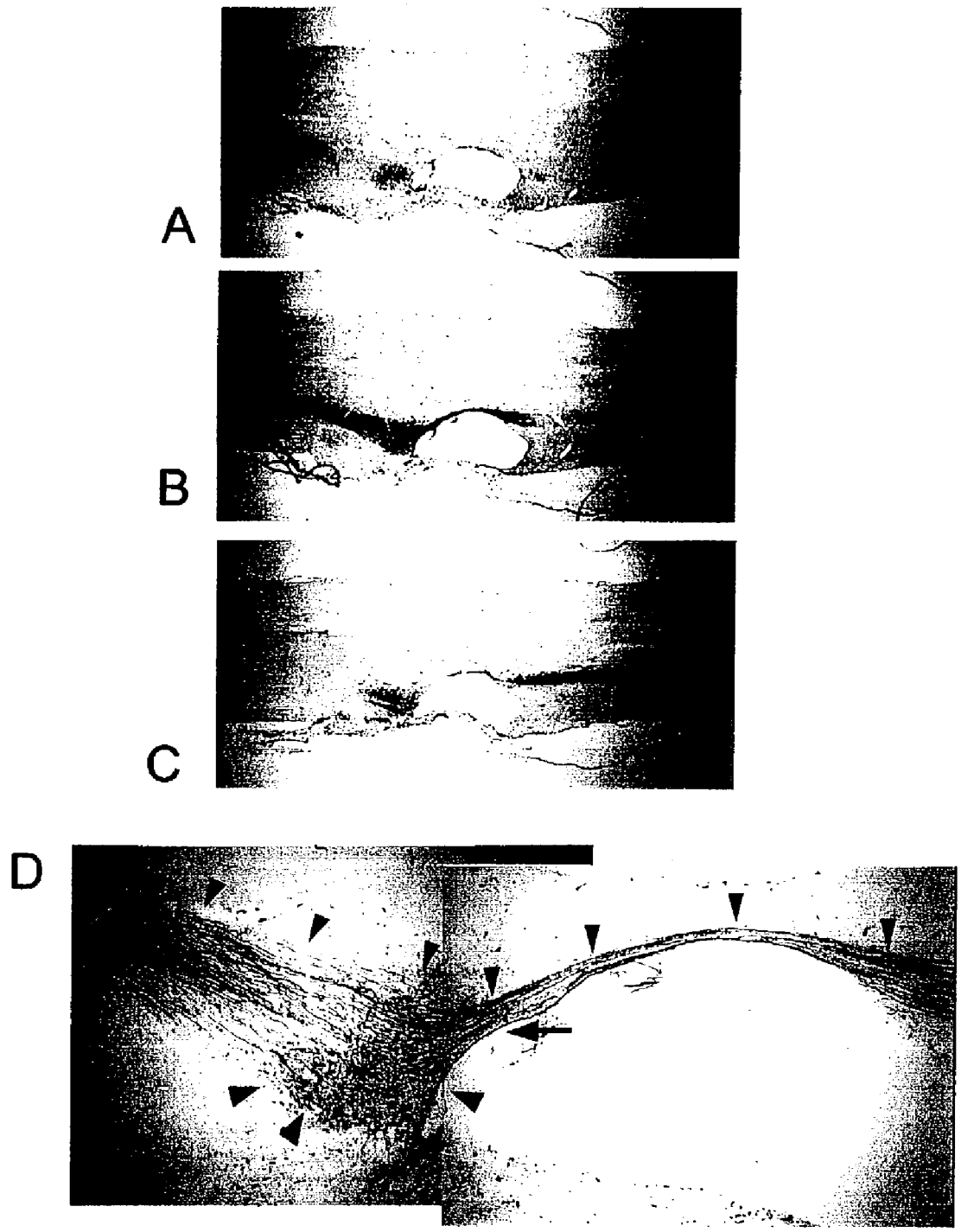
FIG. 11 is photographs showing the results of examining the in vivo nerve-regeneration promoting action of the semaphorin inhibitor SPF-3059-1 of the present invention in the spinal nerve (cerebral cortex-spinal cord pathway) incision.
Figure 12:
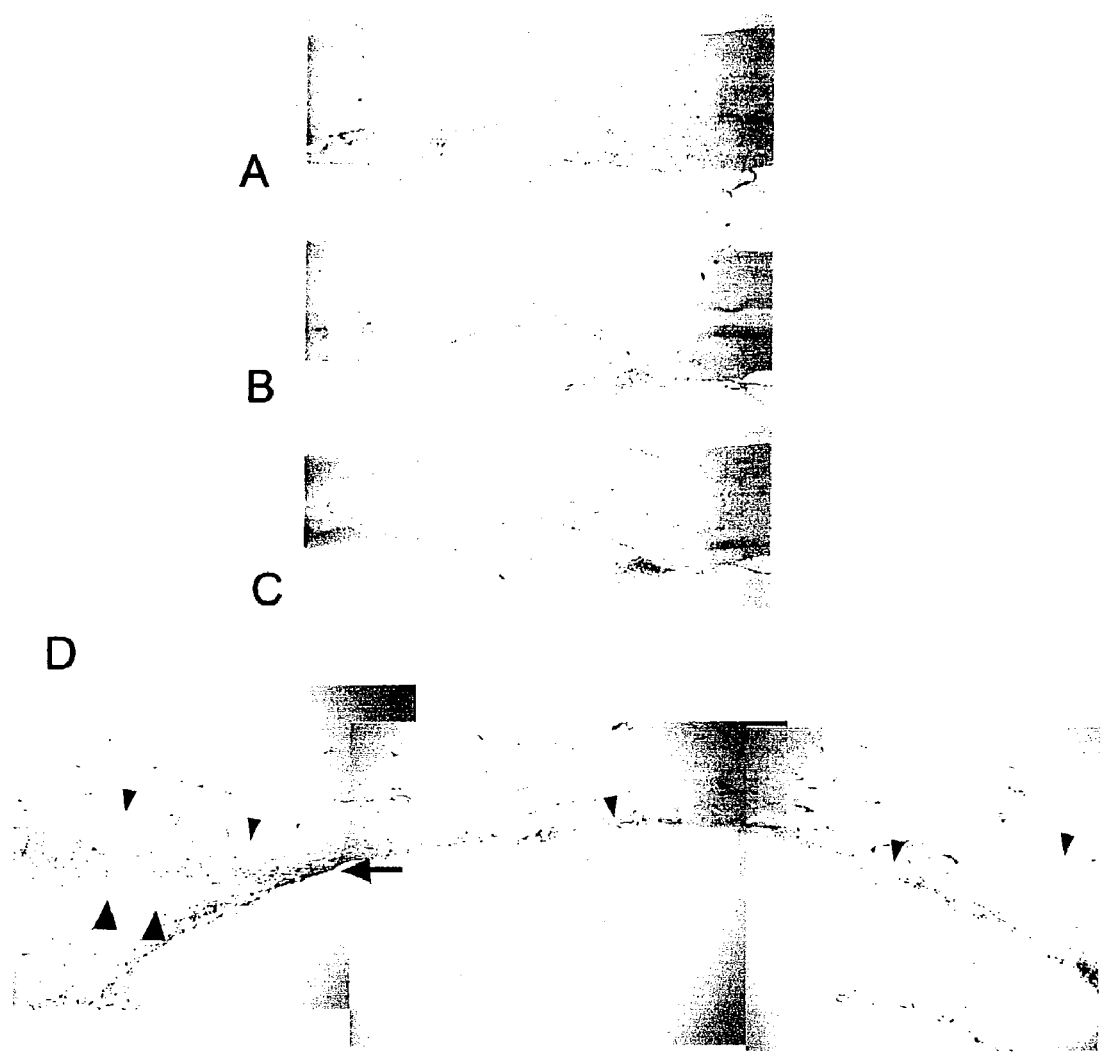
FIG. 12 is photographs showing the results of examining the in vivo nerve-regeneration promoting action of PBS as a control in the spinal nerve (cerebral cortex-spinal cord pathway) incision.

Two weeks after the operation, the rat was anesthetized with pentbarbital (50 mg/kg, intrapenitrially injected) whose head was fixed to the stereotaxic apparatus. The scalp was incised along the median line and the cranium was perforated with a drill to expose the cerebrum. 10% DBA (Dextran Biotinylated Amine) was injected 0.1 µl each to 18 spots in the cerebrum cortex motor area with a microsyringe, after which the incision was sutured and the animal was recovered. DBA will be transported from the nerve nucleus to the spinal cord pathway nerves. After two weeks of breeding, the rat was anesthetized again with pentbarbital and its thoracic part was incised and then PBS was perfused from the left ventricle. Subsequently, PBS containing 200 ml of 4% paraformaldehyde was perfused. The spinal cord (including lesioned part) was taken out and fixed overnight in the solution, which was then placed in PBS containing 30% sucrose and bathed therein at 4.degree. C. The spinal cord was embedded in the OTC compound and frozen on dry ice. 30 µm sections were prepared with a cryostat and aliquoted in Tris buffer solution (TBS). The sections were washed in TBS and bathed in ABC reaction solution for two hours. After the sections were washed, they were visualized with DBA substrate and the preparations were made. Regenerated nerve fibers in the lesioned area were microscopically observed. FIG. 11 shows the result of the injection of SPF-3059-1 of the present invention and FIG. 12 shows the result of PBS injection as a control. FIG. 11A, B and C and FIG. 12A, B and C show serial sections in the proximal of traumatized region, respectively. FIG. 11D and FIG. 12D are large macrographs of FIG. 11B and FIG. 12B, respectively. When SPF-3059-1 was administered, the retention of DBA (dark arrowhead) was observed in the rostral part to the lesion site as shown in FIG. 11D. Many DBA-positive fibers were observed extending from the retention area to the caudal along the lesioned area (light arrowhead) and regenerated nerve fibers that extended evading the incision site were frequently observed. On the contrary, when PBS was administered, DBA retention (dark arrowhead) was observed in the rostral part to the lesion site as shown in FIG. 12D. A few DBA-positive fibers were observed to the caudal side along the lesioned area (light arrowhead) and only a few nerve fibers were observed. These results revealed that SPF-3059-1 has the nerve-regeneration promoting action in the spinal cord injury model adult rats.

EXAMPLE 14

(Production of the Novel Compounds of the Present Invention)

A 10 ml medium containing 2% glucose, 5% sucrose, 2% cotton seed powder, 0.1% sodium nitrate, 0.1% L-histidine, 0.05% dipotassium phosphate, 0.07% potassium chloride and 0.0014% magnesium sulfate heptahydrate, with its pH adjusted to 7.0, was pipetted to a Erlenmeyer flask of 50 ml volume and sterilized in an autoclave. A loopful Penicillium sp. SPF-3059 (FERM BP-7663) on slant culture was inoculated into this medium and cultured with shaking at 180 rpm at 27° C. for 4 as pre-culture. A medium with the same composition as the above-mentioned medium was pipetted 125 ml each to five Erlenmeyer flasks of 500 ml volume and sterilized in an autoclave. Subsequently, the above-mentioned pre-culture solution was added 4 ml each to the five flasks and cultured with shaking at 180 rpm for 4 days at 27.degree. C. A 30 liters of medium containing 1.43% glucose, 3.57% sucrose, 1.43% cotton seed powder, 0.07% sodium nitrate, 0.07% L-histidine, 0.036% dipotassium phosphate, 0.05% potassium chloride, 0.001% magnesium sulfate heptahydrate and 0.01% Adekanol LG-295S (antiforming agent by Asahi Denka Co.,Ltd), with its pH adjusted to 7.0, in a jar fermentor of 50 liters volume was sterilized under high-pressure steam (121.degree. C., 20 min). Then 500 ml of the above-mentioned cultured broth was added to the fermentor and cultured at 27.degree. C. for 9 days with an agitation of 400 rpm and an aeration of 15 liters/min.

When the culture was finished, the cultured broth was centrifuged for 10 minutes at 10,000 rpm to separate the supernatant and the mycelium. The supernatant fraction was extracted twice with a 20 liters of ethyl acetate-formic acid (99:1). The fungus mycelium fraction was extracted with 30 liters of acetone, and then filtered and concentrated. After concentrated into aqueous solution, it was extracted with 10 liters of ethyl acetate-formic acid (99:1). Both extracts were then mixed and concentrated under reduced pressure to obtain 224 g of crude extract. 100 g of this crude extract was dissolved in 500 ml of methanol and applied to a column chromatography using Sephadex (trademark) LH-20 (Amersham Biosciences K. K.), and eluted with methanol. Active fractions were collected and the solvent was evaporated under reduced pressure to obtain 48.8 g of oily substance. The substance was then dissolved in 400 ml of methanol and applied to a column chromatography using TSKgel TOYOPEARL HW-40F (Tosoh Corporation), and eluted with methanol. The active fractions were collected and the solvent was evaporated under reduced pressure to obtain 21.8 g of crude substance. This crude substance was then dissolved in 200 mg aliquots in 2 ml of DMSO and applied to a preparative reversed-phase HPLC. The conditions of the preparative reversed-phase HPLC were, column: Wakopak® Wakosil-II5C18HGprep (connecting 5 i.d.×10 cm and 5 i.d.×25 cm, Wako Pure Chemical Industries, Ltd.), solution A: 1% aqueous formic acid solution, solution B: methanol, gradient: a linear gradient for two hours from 45% to 75% for the proportion of the solution B, flow rate: 25 ml/min, and detection: absorbance at 260 nm. The eluate was fractioned by one minute.

The eluted fractions as described above were analyzed by analytical HPLC. The conditions of the analytical HPLC were, column: Wakopak® Wakosil-II5C18RS (4.6×150 mm, Wako Pure Chemical Industries, Ltd.), solution A: 1% aqueous formic acid solution, solution B: methanol, gradient: a linear gradient for 71.1 min from 20% to 67% for the proportion of the solution B, flow rate: 1.3 ml/min, and detection: absorbance at 260 nm. The fractions containing the object compound were collected with the retention time in this analytical HPLC as the index, and the solvent was evaporated under reduced pressure. The resulting material was again applied to the preparative HPLC and purified in a similar manner as in the above, and were further applied to a column chromatography using TSKgel TOYOPEARL HW-40F (Tosoh Corporation) and purified similarly as in the above. Fractions containing the object compound were collected and the solvent was evaporated under reduced pressure. Thereby, the purified compounds described below were obtained.

| Compound | Amount obtained (mg) | Retention time in the analytical HPLC (min) |
| --- | --- | --- |
| SPF-3059-12 | 6.2 | 34.4 |
| SPF-3059-24 | 28.0 | 34.5 |
| SPF-3059-4 | 10.2 | 36.0 |
| SPF-3059-25 | 4.0 | 39.3 |
| SPF-3059-34 | 2.9 | 40.8 |
| SPF-3059-6 | 34.9 | 45.6 |
| SPF-3059-27 | 17.4 | 46.1 |
| SPF-3059-26 | 6.2 | 46.5 |
| SPF-3059-28 | 11.8 | 46.6 |
| SPF-3059-7 | 13.0 | 47.0 |
| SPF-3059-39 | 2.8 | 49.95 |
| SPF-3059-37 | 4.0 | 50.0 |
| SPF-3059-3 | 118.2 | 50.1 |
| SPF-3059-35 | 11.0 | 51.5 |
| SPF-3059-9 | 100.9 | 52.7 |
| SPF-3059-29 | 45.6 | 54.0 |
| SPF-3059-36 | 3.7 | 57.8 |
| SPF-3059-30 | 23.5 | 63.0 |

Physicochemical properties of the compounds obtained are as follows:

(SPF-3059-3)

Appearance: yellow powder

Molecular weight: 534

Molecular formula: $C_{27}H_{18}O_{12}$

Fast Atom Bombardment Mass Spectrum (FAB-MS) m/z (positive): 535 $(M+H)^+$

Fast Atom Bombardment Mass Spectrum (FAB-MS) m/z (negative): 533 $(M-H)^-$

High Resolution Fast Atom Bombardment Mass Spectrum (HRFAB-MS) m/z $(M+H)^+$: Measured value: 535.0905 Calculated value: 535.0877 ($C_{27}H_{19}O_{12}$)

UV-VISIBLE Absorption Spectrum $\lambda_{max}$ (in methanol) nm (∈): 242 (30,800), 317 (22,700), 367 (14,000)

Infrared Absorption Spectrum $\upsilon_{max}$ (KBr) $cm^{-1}$: 3356, 1700, 1652, 1610, 1515, 1475, 1283

$^1$H-NMR (DMSO-$d_6$) δ ppm: 2.28, 2.29, 2.68, 2.69, 4.62, 4.62, 4.64, 4.72, 5.03, 6.38, 6.40, 6.90, 6.91, 7.44, 7.98, 8.54, 8.90-11.10, 12.70

$^{13}$C-NMR (DMSO-$d_6$) δ ppm: 16.5, 17.0, 32.3, 32.4, 56.2, 65.8, 68.0, 103.0, 104.2, 108.7, 108.8, 109.4, 113.5, 118.2, 118.6, 122.2, 125.7, 127.5, 129.8, 132.0, 132.6, 134.8, 137.6, 137.9, 138.8, 144.3, 150.5, 150.6, 152.0, 152.6, 154.2, 154.5, 155.5, 156.3, 167.6, 167.7, 173.4, 183.5, 186.2, 199.2, 202.8, 203.0

Solubility: Insoluble: water, hexane Soluble: methanol, DMSO

Taken together, the structure of SPF-3059-3 was determined as the following formula [20] (tautomer).

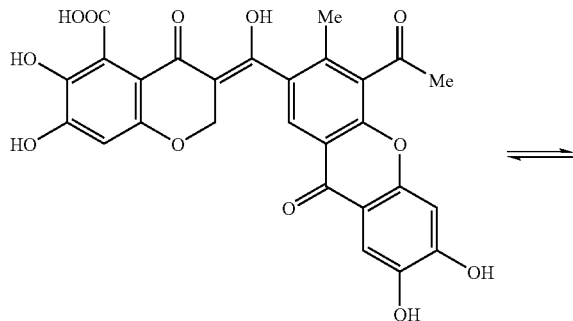
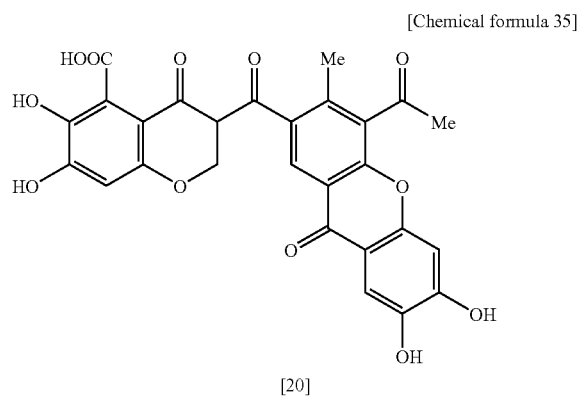

[20]

(SPF-3059-4)
Appearance: Cream-colored powder
Molecular weight: 560
Molecular formula: $C_{28}H_{16}O_{13}$
Fast Atom Bombardment Mass Spectrum (FAB-MS) m/z (positive): 561 (M+H)+
Fast Atom Bombardment Mass Spectrum (FAB-MS) m/z (negative): 559 (M−H)−
High Resolution Fast Atom Bombardment Mass Spectrum (HRFAB-MS) m/z (M+H)+: Measured value: 561.0667 Calculated value: 561.0670 ($C_{28}H_{17}O_{13}$)
UV-VISIBLE Absorption Spectrum $\lambda_{max}$ (in methanol) nm (∈): 221 (35,600), 250 (38,100), 276sh (25,800), 323 (24,300)
Infrared Absorption Spectrum $\upsilon_{max}$ (KBr) cm$^{-1}$: 3412, 1665, 1619, 1563, 1465, 1427, 1263
$^1$H-NMR (DMSO-$d_6$) δ ppm: 2.53 (3H, s), 2.56 (3H, s), 6.84 (1H, d, 2.1), 6.95 (1H, s), 6.96 (1H, d, 2.1), 8.17 (1H, s), 8.52 (1H, s), 10.10–11.40 (3H, brs), 12.71 (1H, brs), 13.26 (1H, brs)
$^{13}$C-NMR (DMSO-$d_6$) δ ppm: 29.2, 32.1, 102.3, 103.2, 110.1, 112.4, 112.8, 119.6, 120.3, 120.8, 126.3, 133.1, 133.4, 136.7, 137.5, 141.7, 150.8, 152.3, 152.7, 152.8, 157.2, 163.9, 167.4, 169.3, 172.2, 172.9, 199.3, 201.0
Solubility: Insoluble: water, hexane Soluble: methanol, DMSO
Taken together, the structure of SPF-3059-4 was determined as the following formula [21].

[Chemical formula 36]

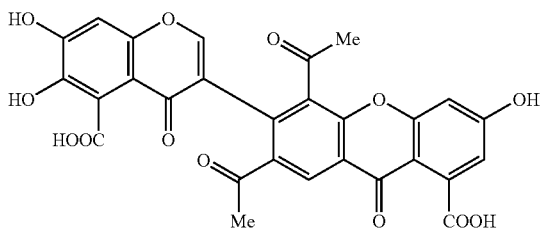

[21]

(SPF-3059-6)
Appearance: Cream-colored powder
Molecular weight: 592
Molecular formula: $C_{29}H_{20}O_{14}$
Fast Atom Bombardment Mass Spectrum (FAB-MS) m/z (positive): 593 (M+H)+
Fast Atom Bombardment Mass Spectrum (FAB-MS) m/z (negative): 591 (M−H)−
High Resolution Fast Atom Bombardment Mass Spectrum (HRFAB-MS) m/z (M+H)+: Measured value: 593.0949 Calculated value: 593.0932 ($C_{29}H_{21}O_{14}$)
UV-VISIBLE Absorption Spectrum $\lambda_{max}$ (in methanol) nm (∈): 210sh (45,900), 223 (47,700), 317 (25,800), 358sh (14,700)
Infrared Absorption Spectrum $\upsilon_{max}$ (KBr) cm$^{-1}$: 3418, 1701, 1617, 1565, 1465, 1301
$^1$H-NMR (DMSO-$d_6$) δ ppm: 2.22 (3H, s), 2.72 (3H, s), 3.11 (3H, s), 3.98 (2H, brs), 6.78 (1H, s), 6.88 (1H, s), 8.21 (1H, s), 9.00–13.00 (6H, brs)
$^{13}$C-NMR (DMSO-$d_6$) δ ppm: 16.8, 32.4, 57.8, 64.4, 102.1, 102.3, 109.3, 111.9, 118.4, 118.6, 119.1, 119.6, 127.6, 128.2, 131.6, 139.0, 141.6, 142.1, 150.7 (2C), 151.9, 152.9, 155.5, 162.0, 167.8, 167.9, 172.4, 174.6, 202.6
Solubility: Insoluble: water, hexane Soluble: methanol, DMSO
Taken together, the structure of SPF-3059-6 was determined as the following formula [22].

[Chemical formula 37]

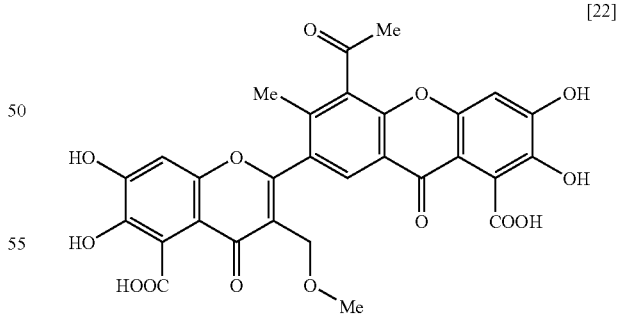

[22]

(SPF-3059-7)
Appearance: Yellow powder
Molecular weight: 562
Molecular formula: $C_{28}H_{18}O_{13}$
Fast Atom Bombardment Mass Spectrum (FAB-MS) m/z (positive): 563 (M+H)+
Fast Atom Bombardment Mass Spectrum (FAB-MS) m/z (negative): 561 (M−H)−

High Resolution Fast Atom Bombardment Mass Spectrum (HRFAB-MS) m/z (M+H)+: Measured value: 563.0843 Calculated value: 563.0826 ($C_{28}H_{19}O_3$)

UV-VISIBLE Absorption Spectrum $\lambda_{max}$ (in methanol) nm (∈): 242 (31,600), 312 (24,500), 385 (10,200)

Infrared Absorption Spectrum $\upsilon_{max}$ (KBr) cm$^{-1}$: 3424, 1701, 1603, 1504, 1448, 1420, 1270

$^1$H-NMR (DMSO-d$_6$) δ ppm: 2.28, 2.29, 2.68, 2.69, 4.62, 4.67, 4.71, 5.04, 6.38, 6.41, 6.81, 6.92, 6.93, 7.95, 8.52, 9.33, 11.22, 11.35, 12.93

$^{13}$C-NMR (DMSO-d$_6$) δ ppm: 16.6, 17.0, 32.3, 32.4, 56.2, 65.7, 67.9, 102.3, 102.8, 103.1, 104.3, 108.7, 109.3, 110.1, 112.5, 112.6, 118.5, 118.7, 121.6, 122.1, 125.9, 127.6, 130.1, 131.9, 132.4, 135.3, 137.4, 137.6, 138.9, 139.7, 151.9, 152.3, 154.5, 155.5, 156.2, 157.1, 163.6, 167.6, 169.3, 172.7, 172.8, 183.7, 186.2, 199.1, 202.5, 202.7

Solubility: Insoluble: water, hexane Soluble: methanol, DMSO

Taken together, the structure of SPF-3059-7 was determined as the following formula [23] (tautomer).

Fast Atom Bombardment Mass Spectrum (FAB-MS) m/z (negative): 533 (M−H)−

High Resolution Fast Atom Bombardment Mass Spectrum (HRFAB-MS) m/z (M+H)+: Measured value: 535.0876 Calculated value: 535.0877 ($C_{27}H_{19}O_{12}$)

UV-VISIBLE Absorption Spectrum $\lambda_{max}$ (in methanol) nm (∈): 207 (47,600), 243 (41,800), 314 (34,000), 369 (23,000)

Infrared Absorption Spectrum $\upsilon_{max}$ (KBr) cm$^{-1}$: 3444, 1702, 1614, 1474, 1289

$^1$H-NMR (DMSO-d$_6$) δ ppm: 2.29, 2.31, 2.67, 2.70, 4.60, 4.65, 4.69, 5.97, 6.32, 6.35, 6.89, 6.90, 7.03, 7.17, 7.94, 8.50, 12.50, 9.20–10.80

$^{13}$C-NMR (DMSO-d$_6$) δ ppm: 16.6, 17.1, 32.3, 32.4, 56.2, 65.9, 68.2, 102.3, 103.0, 103.2, 103.9, 109.9, 110.0, 110.4, 110.5, 111.9, 112.2, 118.2, 118.6, 120.5, 125.7, 127.7, 130.0, 131.9, 132.4, 134.8, 138.2, 139.1, 140.9, 141.1, 141.5,

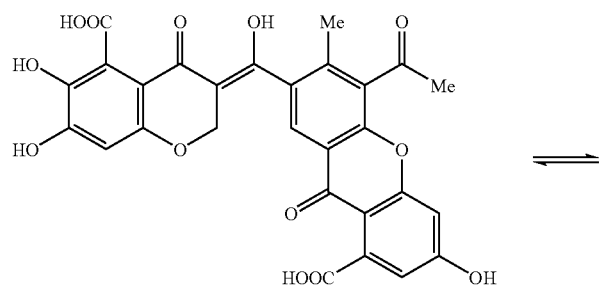
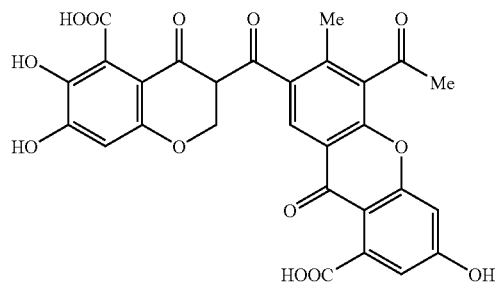

[Chemical formula 38]

[23]

(SPF-3059-9)

Appearance: Yellow powder

Molecular weight: 534

Molecular formula: $C_{27}H_{18}O_{12}$

Fast Atom Bombardment Mass Spectrum (FAB-MS) m/z (positive): 535 (M+H)+

150.2, 150.3, 151.7, 152.2, 154.1, 154.6, 154.9, 155.8, 156.6, 167.5, 172.6, 172.7, 183.5, 187.2, 199.3, 202.7, 202.9

Solubility: Insoluble: water, hexane Soluble: methanol, DMSO

Taken together, the structure of SPF-3059-9 was determined as the following formula [24] (tautomer).

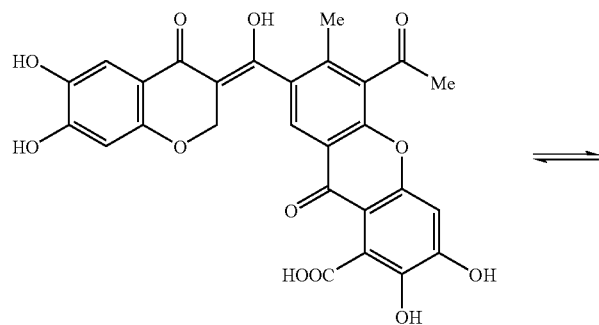
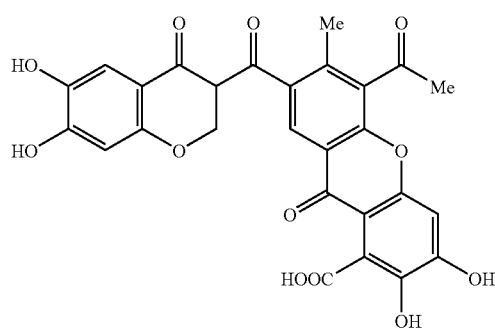

[Chemical formula 39]

[24]

(SPF-3059-12)
Appearance: Cream-colored powder
Molecular weight: 560
Molecular formula: $C_{28}H_{16}O_{13}$
Fast Atom Bombardment Mass Spectrum (FAB-MS) m/z (positive): 561 $(M+H)^+$
Fast Atom Bombardment Mass Spectrum (FAB-MS) m/z (negative): 559 $(M-H)^-$
High Resolution Fast Atom Bombardment Mass Spectrum (HRFAB-MS) m/z $(M+H)^+$: Measured value: 561.0680 Calculated value: 561.0670 ($C_{28}H_{17}O_{13}$)
UV-VISIBLE Absorption Spectrum $\lambda_{max}$ (in methanol) nm (∈): 232 (37,400), 250sh (34,800), 285 (28,000), 308sh (23,200), 360sh (9,000)
Infrared Absorption Spectrum $\upsilon_{max}$ (KBr) $cm^{-1}$: 3080, 1698, 1608, 1468, 1291
$^1$H-NMR (DMSO-$d_6$) δ ppm: 2.54 (3H, s), 2.55 (3H, s), 6.82 (1H, d, 2.1), 6.87 (1H, s), 6.95 (1H, d, 2.1), 8.22 (1H, s), 8.55 (1H, s), 9.50–13.50 (5H, brs)
$^{13}$C-NMR (DMSO-$d_6$) δ ppm: 29.1, 32.2, 102.1, 103.0, 109.4, 112.1, 113.5, 119.8, 120.0, 121.7, 126.6, 132.0, 133.3, 135.9, 136.7, 141.7, 150.6, 152.1, 153.0, 155.4, 157.6, 162.4, 167.4, 167.6, 172.2, 172.9, 199.1, 201.1
Solubility: Insoluble: water, hexane Soluble: methanol, DMSO Taken together, the structure of SPF-3059-12 was determined as the following formula [25].

[Chemical formula 40]

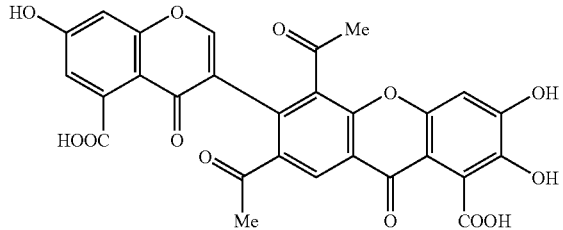

[25]

(SPF-3059-24)
Appearance: Cream-colored powder
Molecular weight: 532
Molecular formula: $C_{27}H_{16}O_{12}$
Fast Atom Bombardment Mass Spectrum (FAB-MS) m/z (positive): 533 $(M+H)^+$
Fast Atom Bombardment Mass Spectrum (FAB-MS) m/z (negative): 531 $(M-H)^-$
High Resolution Fast Atom Bombardment Mass Spectrum (HRFAB-MS) m/z $(M+H)^+$: Measured value: 531.0621 Calculated value: 531.0564 ($C_{27}H_{17}O_{12}$)
UV-visible Absorption Spectrum $\lambda_{max}$ (in methanol) nm (∈): 212 (36,900), 229sh(34,500), 283 (26,300), 323 (21,700)
Infrared Absorption Spectrum $\upsilon_{max}$ (KBr) $cm^{-1}$: 3447, 1697, 1629, 1578, 1470, 1290
$^1$H-NMR (DMSO-$d_6$) δ ppm: 2.52 (3H, s), 2.54 (3H, s), 6.92 (1H, s), 6.93 (1H, s), 7.28 (1H, s), 8.13 (1H, s), 8.54 (1H, s), 9.50–13.00 (5H, brs)
$^{13}$C-NMR (DMSO-$d_6$) δ ppm: 29.1, 32.3, 102.3, 102.9, 107.9, 110.0, 115.8, 119.8, 120.4, 120.7, 126.5, 133.0, 133.3, 136.0, 141.2, 145.0, 150.4, 151.1, 152.2, 152.9, 153.0, 154.3, 167.5, 172.6, 173.6, 199.1, 201.1
Solubility: Insoluble: water, hexane Soluble: methanol, DMSO Taken together, the structure of SPF-3059-24 was determined as the following formula [26].

[Chemical formula 41]

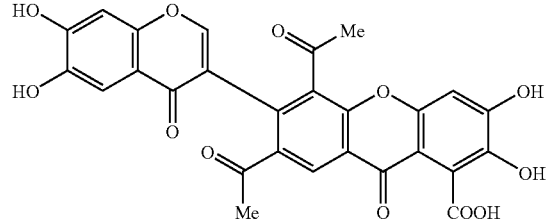

[26]

(SPF-3059-25)
Appearance: Cream-colored powder
Molecular formula: $C_{27}H_{16}O_{11}$
Fast Atom Bombardment Mass Spectrum (FAB-MS) m/z (positive): 517 $(M+H)^+$
Fast Atom Bombardment Mass Spectrum (FAB-MS) m/z (negative): 515 $(M-H)^-$
High Resolution Fast Atom Bombardment Mass Spectrum (HRFAB-MS) m/z $(M+H)^+$: Measured value: 517.0778 Calculated value: 517.0771 ($C_{27}H_{17}O_{11}$)
UV-VISIBLE Absorption Spectrum $\lambda_{max}$ (in methanol) nm (∈): 215 (35,000), 253 (35,100), 276sh(25,200), 323 (23,400)
Infrared Absorption Spectrum $\upsilon_{max}$ (KBr) $cm^{-1}$: 3417, 1691, 1625, 1471, 1293
$^1$H-NMR (DMSO-$d_6$) δ ppm: 2.54 (6H, s), 6.82 (1H, brs), 6.92 (2H, brs), 7.27 (1H, s), 8.14 (1H, s), 8.53 (1H, s), 9.5–14.0 (4H, brs)
$^{13}$C NMR (DMSO-$d_6$) δ ppm: 29.2, 32.3, 102.9, 103.0, 107.8, 109.9, 113.0, 115.7, 120.4, 120.6, 126.4, 133.3, 133.4, 136.4 (2C), 145.0, 151.2, 152.3, 152.98, 153.01, 157.3, 164.2, 169.4, 172.6, 173.6, 199.2, 201.0
Solubility: Insoluble: water, hexane Soluble: methanol, DMSO Taken together, the structure of SPF-3059-25 was determined as the following formula [27].

[Chemical formula 42]

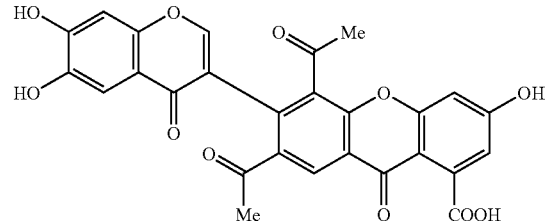

[27]

(SPF-3059-26)
Appearance: Cream-colored powder
Molecular weight: 488
Molecular formula: $C_{26}H_{16}O_{10}$
Fast Atom Bombardment Mass Spectrum (FAB-MS) m/z (positive): 489 $(M+H)^+$
Fast Atom Bombardment Mass Spectrum (FAB-MS) m/z (negative): 487 $(M-H)^-$ High Resolution Fast Atom Bombardment Mass Spectrum (HRFAB-MS) m/z (M+H)$^+$: Measured value: 489.0823 Calculated value: 489.0822 ($C_{26}H_{17}O_{10}$)

UV-VISIBLE Absorption Spectrum $\lambda_{max}$ (in methanol) nm (∈): 212 (31,500), 235 (30,900), 284 (23,900), 324 (19,500)

Infrared Absorption Spectrum $\upsilon_{max}$ (KBr) cm$^{-1}$: 3454, 1694, 1625, 1517, 1471, 1293

$^1$H-NMR (DMSO-d$_6$) δ ppm: 2.53 (3H, s), 2.54 (3H, s), 6.91 (1H, s), 6.92 (1H, s), 7.27 (1H, s), 7.47 (1H, s), 8.11 (1H, s), 8.57 (1H, s)

$^{13}$C-NMR (DMSO-d$_6$) δ ppm: 29.1, 32.2, 102.9, 103.0, 107.9, 108.5, 113.3, 115.7, 119.8, 120.7, 126.3, 132.7, 133.5, 135.8, 144.6, 145.0, 150.8, 151.1, 152.5, 152.9 (2C), 154.7, 173.3, 173.6, 199.1, 201.2

Solubility: Insoluble: water, hexane Soluble: methanol, DMSO

Taken together, the structure of SPF-3059-26 was determined as the following formula [28].

[Chemical formula 43]

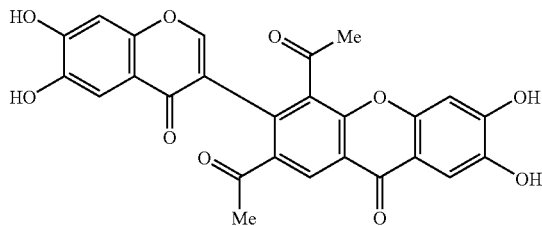

[28]

(SPF-3059-27)
Appearance: Yellow powder
Molecular weight: 642
Molecular formula: $C_{33}H_{22}O_{14}$ Fast Atom Bombardment Mass Spectrum (FAB-MS) m/z (positive): 643 (M+H)$^+$ Fast Atom Bombardment Mass Spectrum (FAB-MS) m/z (negative): 641 (M-H)$^-$ High Resolution Fast Atom Bombardment Mass Spectrum (HRFAB-MS) m/z (M+H)$^+$: Measured value: 643.1088 Calculated value: 643.1089 ($C_{33}H_{23}O_{14}$)

UV-VISIBLE Absorption Spectrum. $\lambda_{max}$ (in methanol) nm (∈): 213 (46,100), 246 (46,600), 287 (31,700), 354 (19,900)

Infrared Absorption Spectrum $\upsilon_{max}$ (KBr) cm$^{-1}$: 3400, 1694, 1640, 1604, 1468, 1290

$^1$H-NMR (DMSO-d$_6$) δ ppm:
2.41 (3H, s), 2.45 (3H, s), 2.67 (3H, s), 6.34 (1H, s), 6.63 (1H, s), 6.90 (1H, s), 7.48 (1H, d, 2.1), 7.97 (1H, d, 2.1), 8.49 (1H, s), 11.9 (1H, brs), 12.5 (1H, brs)

$^{13}$C-NMR (DMSO-d$_6$) δ ppm: 27.4, 30.2, 32.7, 102.3, 102.8, 109.8, 111.8, 117.4, 119.6, 119.7, 120.3, 126.7, 127.5, 128.4, 133.0, 133.4, 135.1, 135.8, 138.6, 139.9, 141.3, 150.5, 151.7, 154.6, 155.8, 157.5, 158.3, 167.5, 172.5, 196.3, 200.0, 201.6, 205.3

Solubility: Insoluble: water, hexane Soluble: methanol, DMSO

Taken together, the structure of SPF-3059-27 was determined as the following formula [29].

[Chemical formula 44]

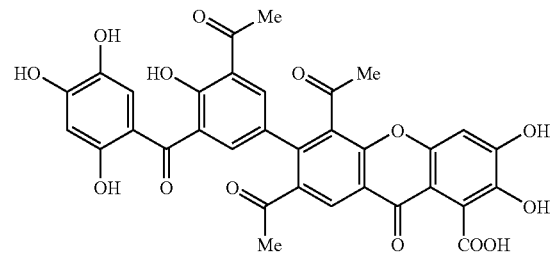

[29]

(SPF-3059-28)
Appearance: Cream-colored powder
Molecular weight: 532
Molecular formula: $C_{27}H_{16}O_{12}$ Fast Atom Bombardment Mass Spectrum (FAB-MS) m/z (positive): 533 (M+H)$^+$ Fast Atom Bombardment Mass Spectrum (FAB-MS) m/z (negative): 531 (M-H)$^-$ High Resolution Fast Atom Bombardment Mass Spectrum (HRFAB-MS) m/z (M+H)$^+$: Measured value: 533.0735 Calculated value: 533.0721 ($C_{27}H_{17}O_{12}$)

UV-VISIBLE Absorption Spectrum $\lambda_{max}$ (in methanol) nm (∈): 217 (35,300), 236 (34,100), 309 (26,100)

Infrared Absorption Spectrum $\upsilon_{max}$ (KBr) cm$^{-1}$: 3502, 3096, 1690, 1598, 1503, 1434, 1303

$^1$H-NMR (DMSO-d$_6$) δ ppm: 2.39 (3H, s), 2.71 (3H, s), 6.52 (1H, s), 6.85 (1H, d, 2.1), 6.92 (1H, d, 2.1), 6.98 (1H, d, 2.1), 8.25 (1H, s), 9.5–13.5 (5H, brs)

$^{13}$C-NMR (DMSO-d$_6$) δ ppm: 17.3, 32.4, 102.3, 103.3, 110.0, 112.1, 112.3, 113.4, 118.8, 120.6, 127.6, 128.9, 132.1, 136.1, 138.8, 140.9, 150.2, 152.0, 154.1, 157.8, 162.2, 162.6, 167.5, 169.2, 172.6, 175.3, 202.7

Solubility: Insoluble: water, hexane Soluble: methanol, DMSO

Taken together, the structure of SPF-3059-28 was determined as the following formula [30].

[Chemical formula 45]

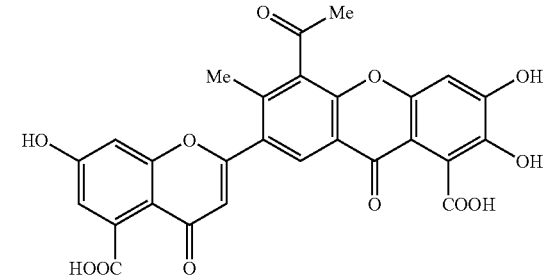

[30]

(SPF-3059-29)
Appearance: Cream-colored powder
Molecular weight: 548
Molecular formula: $C_{28}H_{20}O_{12}$ Fast Atom Bombardment Mass Spectrum (FAB-MS) m/z (positive): 549 (M+H)$^+$ Fast Atom Bombardment Mass Spectrum (FAB-MS) m/z (negative): 547 (M–H)$^-$ High Resolution Fast Atom Bombardment Mass Spectrum (HRFAB-MS) m/z (M+H)$^+$: Measured value: 549.1027 Calculated value: 549.1034 ($C_{28}H_{21}O_{12}$)

UV-VISIBLE Absorption Spectrum $\lambda_{max}$ (in methanol) nm (∈): 226 (48,900), 316 (26,200), 352sh (17,400)

Infrared Absorption Spectrum $\upsilon_{max}$ (KBr) cm$^{-1}$: 3388, 1687, 1662, 1626, 1469, 1296

$^1$H-NMR (DMSO-$d_6$) δ ppm:
2.23 (3H, s), 2.72 (3H, s), 3.11 (3H, s), 3.98 (2H, brs), 6.89 (1H, s), 6.93 (1H, s), 7.44 (1H, s), 8.27 (1Hs), 9.00–13.00 (5H, brs)

$^{13}$C-NMR (DMSO-$d_6$) δ ppm: 16.8, 32.4, 57.8, 64.4, 102.3, 103.1, 108.6, 112.0, 113.5, 118.46, 118.48, 119.1, 127.7, 128.1, 131.8, 138.9, 141.8, 144.3, 150.6, 150.7, 151.9, 152.6, 154.2, 162.1, 167.8, 173.5, 174.6, 202.7

Solubility: Insoluble: water, hexane Soluble: methanol, DMSO

Taken together, the structure of SPF-3059-29 was determined as the following formula [31].

Fast Atom Bombardment Mass Spectrum (FAB-MS) m/z (negative): 489 (M–H)$^-$

High Resolution Fast Atom Bombardment Mass Spectrum (HRFAB-MS) m/z (M+H)$^+$: Measured value: 491.0966 Calculated value: 491.0979 ($C_{26}H_{19}O_{10}$)

UV-VISIBLE Absorption Spectrum $\lambda_{max}$ (in methanol) nm (∈): 206 (36,000), 240 (32,700), 315 (26,500), 372 (17,900)

Infrared Absorption Spectrum $\upsilon_{max}$ (KBr) cm$^{-1}$: 3396, 1704, 1618, 1518, 1479, 1294

$^1$H-NMR (DMSO-$d_6$) δ ppm: 2.28, 2.30, 2.67, 2.69, 4.62, 4.66, 4.70, 4.96, 6.32, 6.36, 6.90, 6.91, 7.03, 7.17, 7.43, 7.98, 8.54, 9.20–10.80

$^{13}$C-NMR (DMSO-$d_6$) δ ppm: 16.5, 17.0, 32.3, 32.4, 56.2, 65.9, 68.3, 103.0, 103.2, 103.8, 108.6, 110.4, 111.8, 113.4, 118.6, 125.6, 127.5, 129.5, 132.1, 132.6, 134.4, 137.9, 138.8, 141.2, 141.5, 144.3, 150.6, 152.0, 152.5, 154.3, 154.6, 154.9, 155.8, 156.6, 172.6, 173.4, 183.5, 187.2, 199.3, 202.7, 202.9

Solubility: Insoluble: water, hexane Soluble: methanol, DMSO

Taken together, the structure of SPF-3059-30 was determined as the following formula [32] (tautomer).

[Chemical formula 47]

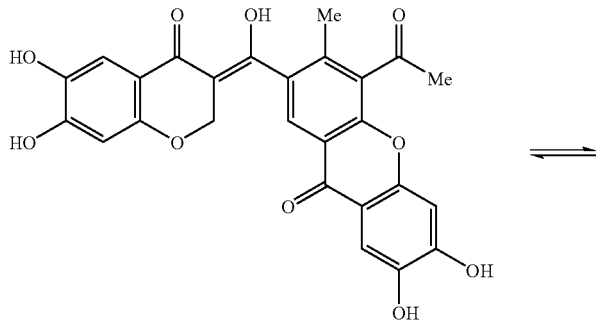

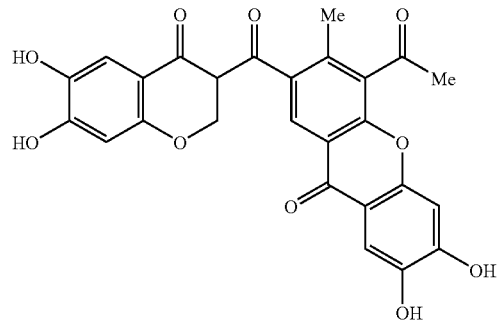

[32]

[Chemical formula 46]

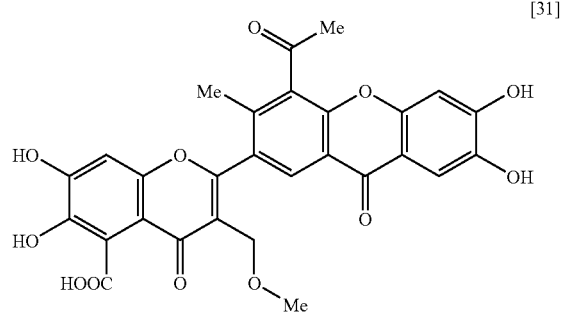

[31]

(SPF-3059-30)

Appearance: Cream-colored powder

Molecular weight: 490

Molecular formula: $C_{26}H_{18}O_{10}$

Fast Atom Bombardment Mass Spectrum (FAB-MS) m/z (positive): 491 (M+H)$^+$ (SPF-3059-34)

Appearance: Yellow powder

Molecular weight: 550

Molecular formula: $C_{27}H_{18}O_{13}$

Fast Atom Bombardment Mass Spectrum (FAB-MS) m/z (positive): 551 (M+H)$^+$

Fast Atom Bombardment Mass Spectrum (FAB-MS) m/z (negative): 549 (M–H)$^-$

High Resolution Fast Atom Bombardment Mass Spectrum (HRFAB-MS) m/z (M+H)$^+$: Measured value: 551.0846 Calculated value: 551.0826 ($C_{27}H_{19}O_{13}$)

UV-VISIBLE Absorption Spectrum $\lambda_{max}$ (in methanol) nm (∈): 211 (35,600), 240 (31,100), 283 (24,100), 349 (14,500)

$^1$H-NMR (DMSO-$d_6$) δ ppm: 2.18 (3H, s), 2.66 (3H, s), 4.39 (1H, d, 11.9), 4.64 (1H, d, 11.9), 6.37 (1H, s), 6.84 (1H, s), 7.09 (1H, s), 8.47 (1H, brs)

$^{13}$C-NMR (DMSO-$d_6$) δ ppm: 16.8, 32.4, 72.5, 80.0, 102.1, 103.0, 109.5, 110.6, 111.1, 117.7, 120.0, 126.5, 131.8, 133.6, 138.6, 141.4, 141.5, 150.5, 151.7, 154.9, 155.0, 156.2, 167.7, 172.6, 188.5, 202.8, 204.0

Solubility: Insoluble: water, hexane Soluble: methanol, DMSO

Taken together, the structure of SPF-3059-34 was determined as the following formula [33].

[Chemical formula 48]

[33]

(SPF-3059-35)
Appearance: Cream-colored powder
Molecular weight: 546
Molecular formula: $C_{28}H_{18}O_{12}$
Fast Atom Bombardment Mass Spectrum (FAB-MS) m/z (positive): 547 (M+H)$^+$
Fast Atom Bombardment Mass Spectrum (FAB-MS) m/z (negative): 545 (M−H)$^-$
High Resolution Fast Atom Bombardment Mass Spectrum (HRFAB-MS) m/z (M+H)$^+$: Measured value: 547.0911 Calculated value: 547.0877 ($C_{28}H_{19}O_{12}$)
UV-VISIBLE Absorption Spectrum $\lambda_{max}$ (in methanol) nm (∈): 216 (38,600), 237 (37,300), 307 (30,100), 356sh (8,800)
Infrared Absorption Spectrum $\upsilon_{max}$ (KBr) cm$^{-1}$: 3460, 3076, 1734, 1699, 1629, 1466, 1302
$^1$H-NMR (DMSO-d$_6$) δ ppm: 2.39 (3H, s), 2.71 (3H, s), 3.82 (3H, s), 6.49 (1H, s), 6.86 (1H, d, 2.1), 6.92 (1H, s), 7.01 (1H, d, 2.1), 8.25 (1H, s), 9.5–13.5 (4H, brs)
$^{13}$C-NMR (DMSO-d$_6$) δ ppm: 17.3, 32.4, 52.5, 102.3, 103.8, 110.0, 112.1, 112.8, 113.5, 118.8, 120.6, 127.7, 129.0, 132.1, 134.3, 138.8, 140.9, 150.3, 152.1, 154.1, 157.7, 162.2, 162.8, 167.5, 168.6, 172.6, 175.1, 202.7
Solubility: Insoluble: water, hexane Soluble: methanol, DMSO
Taken together, the structure of SPF-3059-35 was determined as the following formula [34].

[Chemical formula 49]

[34]

(SPF-3059-36)
Appearance: Cream-colored powder
Molecular weight: 598
Molecular formula: $C_{32}H_{22}O_{12}$
Fast Atom Bombardment Mass Spectrum (FAB-MS) m/z (positive): 599 (M+H)$^+$
Fast Atom Bombardment Mass Spectrum (FAB-MS) m/z (negative): 597 (M−H)$^-$
High Resolution Fast Atom Bombardment Mass Spectrum (HRFAB-MS) m/z (M+H)$^+$: Measured value: 599.1198 Calculated value: 599.1190 ($C_{32}H_{23}O_{12}$)
UV-VISIBLE Absorption Spectrum $\lambda_{max}$ (in methanol) nm (∈): 213 (46,300), 246 (48,700), 287 (33,200), 360 (20,000)
$^1$H-NMR (DMSO-d$_6$) δ ppm:
2.41 (3H, s), 2.45 (3H, s), 2.66 (3H, s), 6.34 (1H, s), 6.63 (1H, s), 6.90 (1H, s), 7.46 (1H, d, 2.0), 7.46 (1H, s), 7.95 (1H, d, 2.0), 8.52 (1H, s)
$^{13}$C-NMR (DMSO-d$_6$) δ ppm: 27.3, 30.2, 32.7, 102.8, 103.1, 108.6, 111.7, 113.4, 117.3, 119.6 (2C), 126.7, 127.5, 128.5, 133.2, 133.4, 135.1, 135.6, 138.6, 139.7, 144.6, 150.8, 152.1, 154.6, 155.9, 157.5, 158.4, 173.3, 196.3, 200.0, 201.6, 205.2
Solubility: Insoluble: water, hexane Soluble: methanol, DMSO
Taken together, the structure of SPF-3059-36 was determined as the following formula [35].

[Chemical formula 50]

[35]

(SPF-3059-37)
Appearance: Yellow powder
Molecular weight: 806
Molecular formula: $C_{41}H_{26}O_{18}$
Fast Atom Bombardment Mass Spectrum (FAB-MS) m/z (positive): 807 (M+H)$^+$
Fast Atom Bombardment Mass Spectrum (FAB-MS) m/z (negative): 805 (M−H)$^-$
High Resolution Fast Atom Bombardment Mass Spectrum (HRFAB-MS) m/z (M−H)$^-$: Measured value: 807.1197 Calculated value: 807.1198 ($C_{41}H_{27}O_{18}$)
UV-VISIBLE Absorption Spectrum $\lambda_{max}$ (in methanol) nm (∈): 219 (68,900), 323 (30,700), 349 (30,600)
$^1$H-NMR (DMSO-d$_6$) δ ppm: 2.08 (3H, s), 2.20 (3H, s), 2.53 (3H, s), 3.42 (1H, d, 15.6), 3.56 (1H, d, 15.6), 4.64 (1H, d, 13.4), 4.71 (1H, d, 13.4), 6.27 (1H, s), 6.83 (1H, s), 6.84 (1H, s), 6.88 (1H, s), 8.15 (1H, s), 9.0–13.0 (8H, brs)
$^{13}$C-NMR (DMSO-d$_6$) δ ppm: 16.6, 17.7, 20.0, 32.0, 62.3, 102.1, 102.25, 103.8, 106.0, 108.4, 108.7, 109.9, 111.55, 118.56, 119.2, 119.6, 120.4, 121.7, 127.9, 129.13, 131.1, 139.5, 140.6, 141.00, 141.7, 150.1, 150.23, 150.46, 150.51, 151.6, 152.3, 154.09, 154.17, 158.7, 161.1, 167.7, 168.0, 172.5, 173.2, 175.1, 202.2
Solubility: Insoluble: water, hexane Soluble: methanol, DMSO Taken together, the structure of SPF-3059-37 was determined as the following formula [36].

[Chemical formula 51]

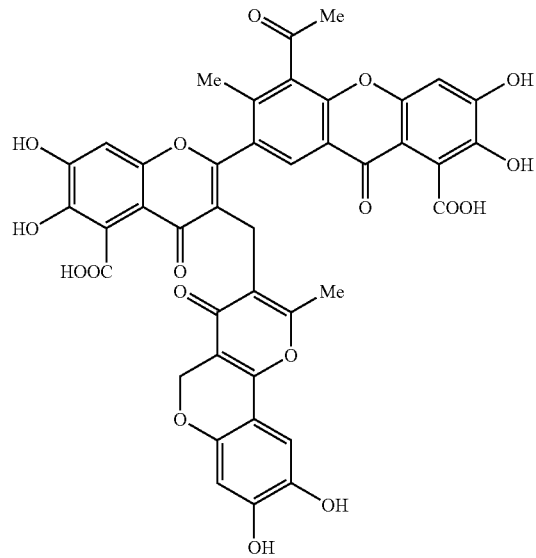

[36]

(SPF-3059-39)

Appearance: Yellow powder

Molecular weight: 548

Molecular formula: $C_{27}H_{16}O_{13}$

Fast Atom Bombardment Mass Spectrum (FAB-MS) m/z (positive): 549 (M+H)$^+$

Fast Atom Bombardment Mass Spectrum (FAB-MS) m/z (negative): 547 (M−H)$^-$

UV-VISIBLE Absorption Spectrum $\lambda_{max}$ (in methanol) nm (∈): 223 (40,000), 319 (23,900), 349 (20,100)

$^1$H-NMR (DMSO-d$_6$) δ ppm: 2.37 (3H, s), 2.71 (3H, s), 6.47 (3H, s), 6.91 (1H, s), 6.98 (1H, s), 8.22 (1H, s), 9.0–13.0 (6H, brs)

$^{13}$C-NMR (DMSO-d$_6$) δ ppm: 17.3, 32.4, 102.3, 102.7, 109.9, 111.49, 112.4, 118.64, 118.8, 120.5, 127.5, 129.12, 132.1, 138.8, 140.96, 142.5, 150.29, 151.1, 152.0, 152.6, 154.24, 162.1, 167.5, 167.9, 172.6, 175.5, 202.7

Solubility: Insoluble: water, hexane Soluble: methanol, DMSO

Taken together, the structure of SPF-3059-39 was determined as the following formula [37].

[Chemical formula 52]

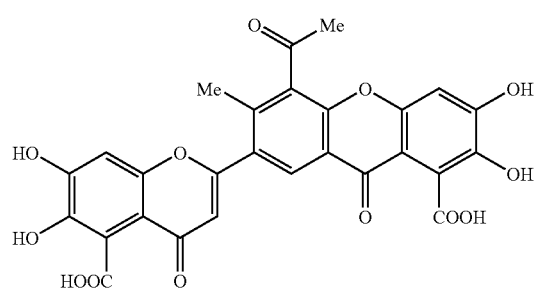

[37]

EXAMPLE 15

Inhibitory Action of the Novel Compounds of the Present Invention to the Collapse Activity of Sema 3A In a similar manner as in Example 2, inhibitory actions of the novel compounds of the present invention to the collapse activity of Sema 3A were measured. IC50 were as follows and all of them strongly inhibited Sema 3A.

| Compound | IC50 (μg/ml) |
| --- | --- |
| SPF-3059-3 | 0.2 |
| SPF-3059-4 | 2.0 |
| SPF-3059-6 | 0.1 |
| SPF-3059-7 | 1.0 |
| SPF-3059-9 | 0.1 |
| SPF-3059-12 | 2.0 |
| SPF-3059-24 | 0.1 |
| SPF-3059-25 | 4.0 |
| SPF-3059-26 | 0.2 |
| SPF-3059-27 | 0.5 |
| SPF-3059-28 | 2.0 |
| SPF-3059-29 | 0.1 |
| SPF-3059-30 | 0.2 |
| SPF-3059-34 | 0.1 |
| SPF-3059-35 | 2.0 |
| SPF-3059-36 | 4.0 |
| SPF-3059-37 | <0.1 |
| SPF-3059-39 | 0.1 |

EXAMPLE 16

Inhibition of the Neurite Outgrowth-inhibitory Action of Sema3A by the Inhibitor In a similar manner as in Example 5, the inhibitory actions of the novel compounds of the present invention to the neurite outgrowth-inhibitory action of Sema3A were measured. The results of the measurement are presented below.

| | Compound concentration (μg/ml) | | |
| --- | --- | --- | --- |
| Compound | 2 | 6 | 20 |
| SPF-3059-2 | +++ | NT | NT |
| SPF-3059-3 | +++ | NT | NT |
| SPF-3059-5 | ++ | NT | NT |
| SPF-3059-4 | − | + | ++ |
| SPF-3059-6 | ++ | ++ | +++ |
| SPF-3059-7 | + | + | ++ |
| SPF-3059-12 | + | + | ++ |
| PBS (Control) | − | − | − |

(NT = not tested)

This result demonstrates that the neurite outgrowth-inhibitory action presented by Sema 3A can be persistently inhibited by the novel compounds of the present invention.

EXAMPLE 17

Determination of Cytotoxicity of the Novel Compounds of the Present Invention

The effects of the compounds to cell proliferation were determined by using COS7 cells, in a similar manner as in Example 10. The determination results of the cell proliferation inhibition of the novel compounds of the present invention were as follows. It was revealed that no cytotoxicity was observed at a concentration as high as 50 to 1000 folds of the concentration where semaphorin activities can be observed.

| Subject Compound | IC50 (µg/ml) |
|---|---|
| SPF-3059-3 | >100 |
| SPF-3059-4 | >100 |
| SPF-3059-6 | >100 |
| SPF-3059-7 | >100 |
| SPF-3059-9 | >100 |
| SPF-3059-12 | >100 |
| SPF-3059-24 | >100 |
| SPF-3059-29 | >100 |
| SPF-3059-30 | >100 |

EXAMPLE 18

Production of Salts of the Compounds of the Present Invention

A compound of the present invention is dissolved in methanol to prepare 1 mM solution. Methanol solution of 1 mM sodium hydroxide is added to 1 ml of the above solution by 2 ml when a compound of the present invention has two carboxyl groups and by 1 ml when it has one carboxyl group, and is mixed thoroughly. The solvent of the solution is evaporated under reduced pressure and the residues are dried, and thus 1 µmol of sodium salt of a compound of the present invention is obtained.

INDUSTRIAL APPLICABILITY

The semaphorin inhibitors as an active ingredient for nerve regeneration promoters of the present invention have the peripheral or central nerve regeneration promoting action even at a low concentration and have suppressing action on the growth cone collapse activity of semaphorin and/or on the neurite outgrowth inhibitory activity of semaphorin in a collagen gel. Especially, a low molecular weight compound semaphorin inhibitor with a molecular weight of 1000 or less is advantageously used as a preventive or a remedy for various neuropathic and neurodegenerative diseases because of its significant molecular diffusibility, membrane permeability, organ distribution, blood-brain barrier permeability in particular, or the like.

The invention claimed is:

1. A method for promoting nerve regeneration, comprising administering an effective amount of a compound obtained from cultivating *Penicillium* sp. SPF-3059 containing a group represented by formulae [1], [2], [4], [5], [6] or [7] in the molecule, or a pharmaceutically acceptable salt thereof,

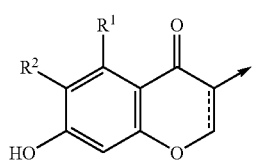

[1]

wherein, ----- represents a single bond or a double bond, $R^1$ represents a hydrogen atom, a carboxyl group or an alkoxycarbonyl group and $R^2$ represents a hydrogen atom, a hydroxyl group or an acyloxy group,

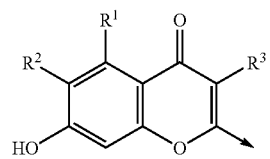

[2]

wherein $R^1$ represents a hydrogen atom, a carboxyl group or an alkoxycarbonyl group and $R^2$ represents a hydrogen atom, a hydroxyl group or an acyloxy group, and $R^3$ represents a hydrogen atom, a methoxymethyl group or formula [3],

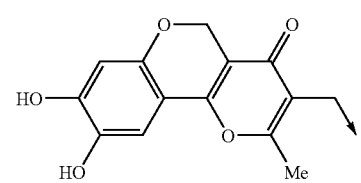

[3]

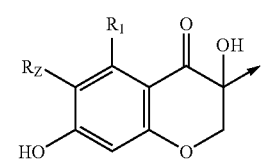

[4]

wherein $R^1$ represents a hydrogen atom, a carboxyl group or an alkoxycarbonyl group and $R^2$ represents a hydrogen atom, a hydroxyl group or an acyloxy group,

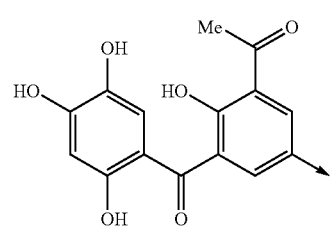

[5]

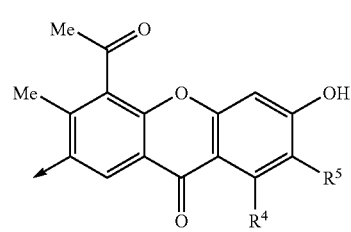

[6]

wherein $R^4$ represents a hydrogen atom, a carboxyl group or an alkoxycarbonyl group and $R^5$ represents a hydrogen atom, a hydroxyl group or an acyloxy group,

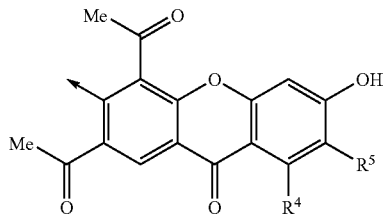

[7]

wherein R⁴ represents a hydrogen atom, a carboxyl group or an alkoxycarbonyl group and R⁵ represents a hydrogen atom, a hydroxyl group or an acyloxy group.

2. The method according to claim 1, comprising administering the compound obtained from cultivating *Penicillium* sp. SPF-3059 which contains a group represented by formulae [1], [2], [4] or [5] and a group represented by formulae [6] or [7] in the molecule, or a pharmaceutically acceptable salt thereof, as an active ingredient to a patient in need thereof,

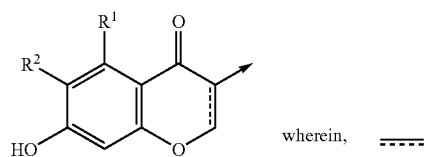

[1]

wherein, ===== represents a single bond or a double bond, R¹ represents a hydrogen atom, a carboxyl group or an alkoxycarbonyl group and R² represents a hydrogen atom, a hydroxyl group or an acyloxy group,

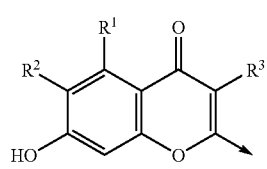

[2]

wherein R¹ represents a hydrogen atom, a carboxyl group or an alkoxycarbonyl group and R² represents a hydrogen atom, a hydroxyl group or an acyloxy group, and R³ represents a hydrogen atom, a methoxymethyl group or formula [3],

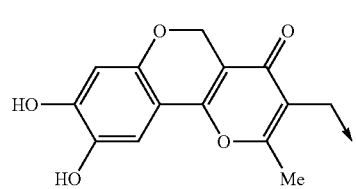

[3]

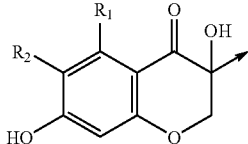

[4]

wherein R¹ represents a hydrogen atom, a carboxyl group or an alkoxycarbonyl group and R² represents a hydrogen atom, a hydroxyl group or an acyloxy group,

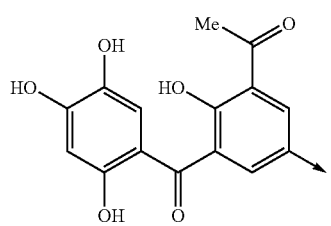

[5]

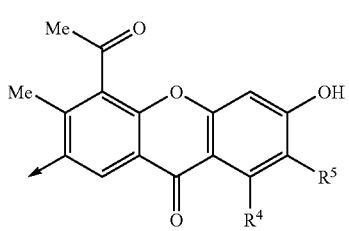

[6]

wherein R⁴ represents a hydrogen atom, a carboxyl group or an alkoxycarbonyl group and R⁵ represents a hydrogen atom, a hydroxyl group or an acyloxy group,

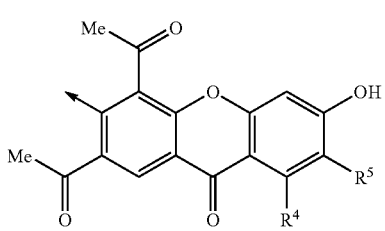

[7]

wherein R⁴ represents a hydrogen atom, a carboxyl group or an alkoxycarbonyl group and R⁵ represents a hydrogen atom, a hydroxyl group or an acyloxy group.

3. The method according to claim 1, comprising administering the compound obtained from cultivating *Penicillium* sp. SPF-3059 represented by formula [8], or a pharmaceutically acceptable salt thereof as an active ingredient to a patient in need thereof,

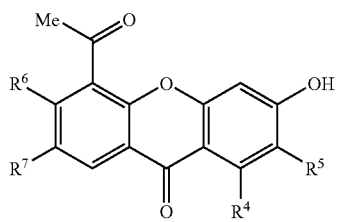

[8]

wherein R⁴ represents a hydrogen atom, a carboxyl group or an alkoxycarbonyl group and R⁵ represents a hydrogen atom, a hydroxyl group or an acyloxy group, and R⁶ and R⁷ are represented by either (1) or (2) below:
(1) R⁶ represents a methyl group and R⁷ represents a group shown by formulae [2], [9] or [10],

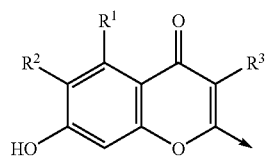

[2]

wherein R¹ represents a hydrogen atom, a carboxyl group or an alkoxycarbonyl group and R² represents a hydrogen atom, a hydroxyl group or an acyloxy group, and R³ represents a hydrogen atom, a methoxymethyl group or formula [3],

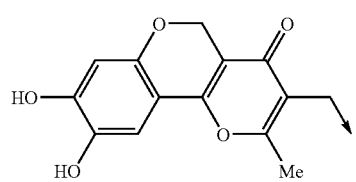

[3]

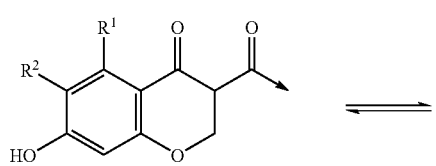

[9]

wherein R¹ represents a hydrogen atom, a carboxyl group or an alkoxycarbonyl group and R² represents a hydrogen atom, a hydroxyl group or an acyloxy group,

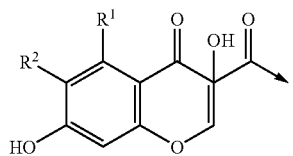

[10]

wherein R¹ represents a hydrogen atom, a carboxyl group or an alkoxycarbonyl group and R² represents a hydrogen atom, a hydroxyl group or an acyloxy group, (2) R⁶ represents a group shown by formulae [5] or [11] and R⁷ represents an acetyl group,

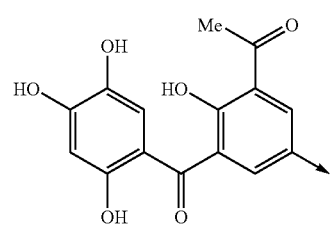

[5]

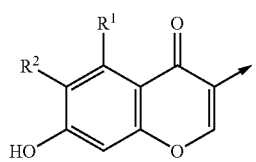

[11]

wherein R¹ represents a hydrogen atom, a carboxyl group or art alkoxycarbonyl group and R² represents a hydrogen atom, a hydroxyl group or an acyloxy group.

4. The method according to claim 1, comprising administering the compound obtained from cultivating *Penicillium* sp. SPF-3059 represented by formula [12], or a pharmaceutically acceptable salt thereof, as an active ingredient to a patient in need thereof,

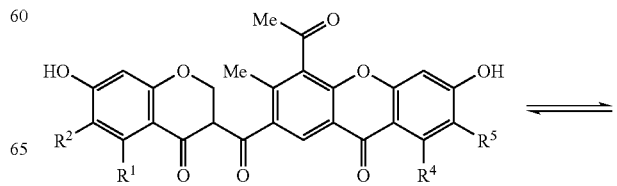

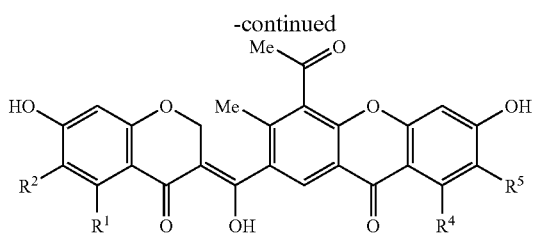

[12]

wherein $R^1$ represents a hydrogen atom, a carboxyl group or an alkoxycarbonyl group, $R^2$ represents a hydrogen atom, a hydroxyl group or an acyloxy group, $R^4$ represents a hydrogen atom, a carboxyl group or an alkoxycarbonyl group and $R^5$ represents a hydrogen atom, a hydroxyl group or an acyloxy group.

5. The method according to claim 4, wherein at least one of $R^2$ and $R^5$ represents a hydroxyl group in formula [12].

6. The method according to claim 5, wherein $R^2$ represents a hydroxyl group in formula [12].

7. The method according to claim 5, wherein $R^2$ and $R^5$ represent a hydroxyl group in formula [12].

8. The method according to claim 4, wherein $R^4$ represents a carboxyl group in formula [12].

9. The method according to claim 4, wherein $R^1$ and $R^4$ represent a carboxyl group and $R^2$ represents a hydroxyl group in formula [12].

10. The method according to claim 1, comprising administering the non-peptide and the non-nucleotide compound obtained from cultivating *Penicillium* sp. SPF-3059 represented by formula [13], or a pharmaceutically acceptable salt thereof, as an active ingredient to a patient in need thereof,

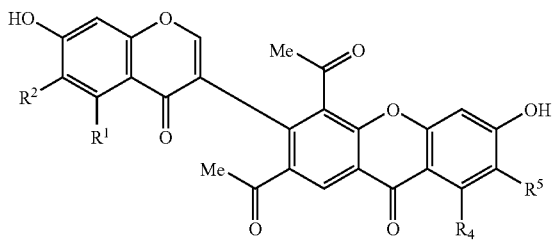

[13]

wherein $R^1$ represents a hydrogen atom, a carboxyl group or an alkoxycarbonyl group, $R^2$ represents a hydrogen atom, a hydroxyl group or an acyloxy group, $R^4$ represents a hydrogen atom, a carboxyl group or an alkoxycarbonyl group and $R^5$ represents a hydrogen atom, a hydroxyl group or an acyloxy group.

11. The method according to claim 10, wherein at least one of $R^2$ and $R^5$ represents a hydroxyl group in formula [13].

12. The method according to claim 11, wherein $R^2$ represents a hydroxyl group in formula [13].

13. The method according to claim 11, wherein $R^2$ and $R^5$ represent a hydroxyl group in formula [13].

14. The method according to claim 10 wherein $R^4$ represents a carboxyl group in formula [13].

15. The method according to claim 10, wherein $R^2$ and $R^5$ represent a hydroxyl group, $R^1$ represents a carboxyl group and $R^4$ represents a hydrogen atom in formula [13].

16. The method according to claim 10 wherein $R^1$ and $R^4$ represent a carboxyl group and $R^5$ represents a hydroxyl group in formula [13].

17. A compound represented by formula [14], or a pharmaceutically acceptable salt thereof,

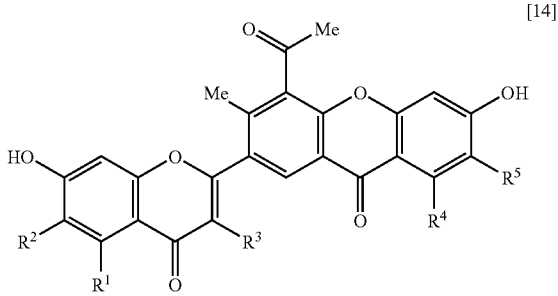

[14]

wherein $R^1$ represents a hydrogen atom, a carboxyl group or an alkoxycarbonyl group, $R^2$ represents a hydrogen atom, a hydroxyl group or an acyloxy group, $R^3$ represents a hydrogen atom, a methoxymethyl group or formula [3], $R^4$ represents a hydrogen atom, a carboxyl group or an alkoxycarbonyl group and $R^5$ represents a hydrogen atom, a hydroxyl group or an acyloxy group.

18. The compound according to claim 17 wherein at least one of $R^2$ and $R^5$ represents a hydroxyl group, a pharmaceutically acceptable salt thereof or a derivative thereof.

19. The compound according to claim 18 wherein $R^2$ represents a hydroxyl group, a pharmaceutically acceptable salt thereof or a derivative thereof.

20. The compound according to claim 18 wherein $R^2$ and $R^5$ represent a hydroxyl group, a pharmaceutically acceptable salt thereof or a derivative thereof.

21. The compound according to claim 17 wherein $R^4$ represents a carboxyl group, a pharmaceutically acceptable salt thereof or a derivative thereof.

22. The compound according to claim 17 wherein $R^1$ and $R^4$ represent a carboxyl group and $R^2$ and $R^5$ represent a hydroxyl group, a pharmaceutically acceptable salt thereof or a derivative thereof.

23. The compound according to claim 17 wherein $R^1$ represents a carboxyl group, $R^2$ and $R^5$ represent a hydroxyl group and $R^3$ represents a methoxymethyl group, a pharmaceutically acceptable salt thereof or a derivative thereof.

24. The compound according to claim 17 wherein $R^1$ represents a carboxyl group or a methoxycarbonyl group, $R^4$ represents a carboxyl group, $R^3$ represents a hydrogen atom and $R^5$ represents a hydroxyl group, a pharmaceutically acceptable salt thereof or a derivative thereof.

25. The compound according to claim 24 wherein $R^1$ represents a carboxyl group or a methoxycarbonyl group, $R^4$ represents a carboxyl group, $R^2$ and $R^3$ represent a hydrogen atom and $R^5$ represents a hydroxyl group, a pharmaceutically acceptable salt thereof or a derivative thereof.

26. The compound according to claim 17, wherein $R^3$ represents a group shown by formula [3], a pharmaceutically acceptable salt thereof or a derivative thereof.

[Chemical formula 29]

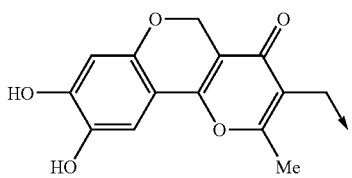

[3]

27. A method for promoting nerve regeneration, comprising administering an effective amount of the compound represented by formula [14], or a pharmaceutically acceptable salt thereof, as an active ingredient to a patient in need thereof,

[14]

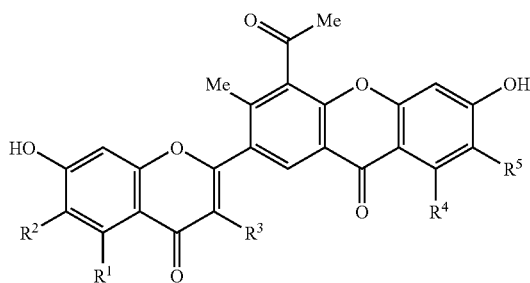

wherein $R^1$ represents a hydrogen atom, a carboxyl group or an alkoxycarbonyl group, $R^2$ represents a hydrogen atom, a hydroxyl group or an acyloxy group, $R_4$ represents a hydrogen atom, a carboxyl group or an alkoxycarbonyl group, $R_5$ represents a hydrogen atom, a hydroxyl group or an acyloxy group and $R_3$ represents a hydrogen atom, a methoxymethyl group or formula [3].

28. A compound represented by formula [15], or a pharmaceutically acceptable salt thereof,

[15]

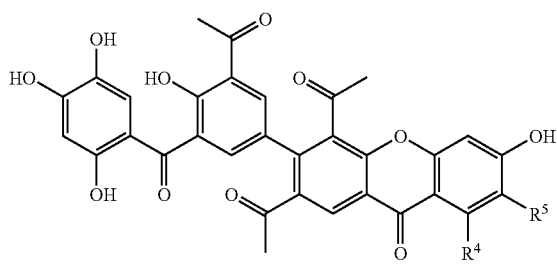

wherein $R^4$ represents a hydrogen atom, a carboxyl group or an alkoxycarbonyl group and $R^5$ represents a hydrogen atom, a hydroxyl group or an acyloxy group.

29. The compound according to claim 28 wherein $R^5$ represents a hydroxyl group, a pharmaceutically acceptable salt thereof or a derivative thereof.

30. The compound according to claim 28 wherein $R^4$ represents a carboxyl group, a pharmaceutically acceptable salt thereof or a derivative thereof.

31. A method for promoting nerve regeneration, comprising administering an effective amount of the compound represented by formula [15], or a pharmaceutically acceptable salt thereof, as an active ingredient to a patient in need thereof,

[15]

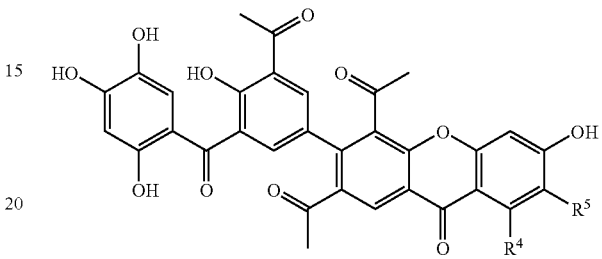

wherein $R^4$ represents a hydrogen atom, a carboxyl group or an alkoxycarbonyl group and $R^5$ represents a hydrogen atom, a hydroxyl group or an acyloxy group.

32. A compound represented by formula [16], a pharmaceutically acceptable salt thereof,

[16]

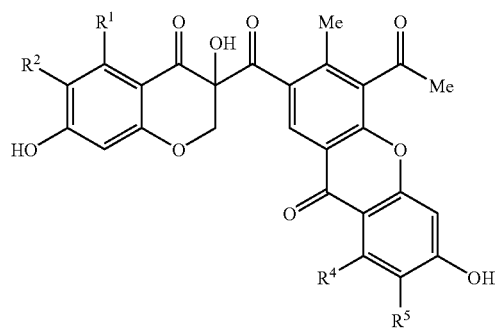

wherein $R^1$ represents a hydrogen atom, a carboxyl group or an alkoxycarbonyl group, $R^2$ represents a hydrogen atom, a hydroxyl group or an acyloxy group, $R^4$ represents a hydrogen atom, a carboxyl group or an alkoxycarbonyl group and $R^5$ represents a hydrogen atom, a hydroxyl group or an acyloxy group.

33. The compound according to claim 32 wherein at least one of $R^2$ and $R^5$ represents a hydrogen atom, a pharmaceutically acceptable salt thereof or a derivative thereof.

34. The compound according to claim 32 wherein $R^2$ and $R^5$ represent a hydroxyl group, a pharmaceutically acceptable salt thereof or a derivative thereof.

35. The compound according to claim 32 wherein $R^4$ represents a carboxyl group, a pharmaceutically acceptable salt thereof or a derivative thereof.

36. A method for promoting nerve regeneration, comprising administering an effective amount of the compound represented by formula [16], or a pharmaceutically acceptable salt thereof, as an active ingredient to a patient in need thereof,

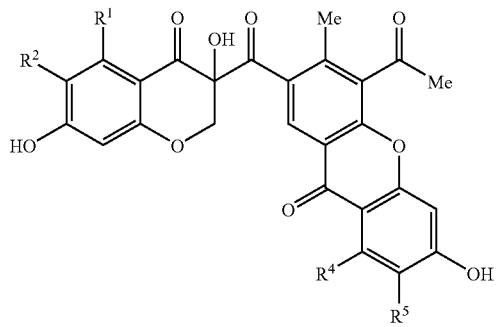

[16]

wherein $R^1$ represents a hydrogen atom, a carboxyl group or an alkoxycarbonyl group, $R^2$ represents a hydrogen atom, a hydroxyl group or an acyloxy group, $R^4$ represents a hydrogen atom, a carboxyl group or an alkoxycarbonyl group and $R_5$ represents a hydrogen atom, a hydroxyl group or an acyloxy group.

37. A process for producing the compound represented by formula [12], wherein the process comprises the steps of: 1) cultivating in a culture medium a compound-producing fungus which belongs to the genus *Penicillium*, which is *Penicillium* sp. SPF-3059 having accession number FERM BP-7663 to produce a compound of formula [12],

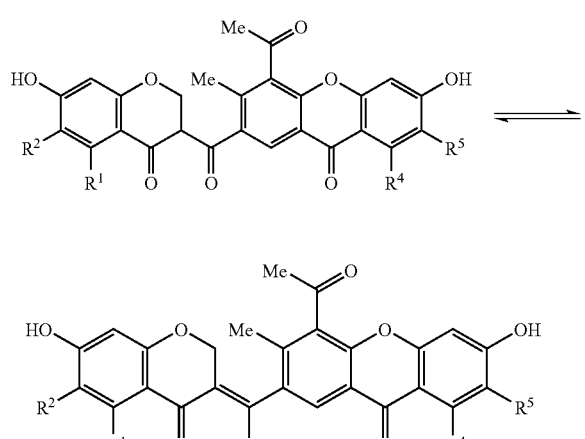

[12]

wherein $R^1$ represents a hydrogen atom, a carboxyl group or an alkoxycarbonyl group, $R^2$ represents a hydrogen atom, a hydroxyl group or an acyloxy group, $R^4$ represents a hydrogen atom, a carboxyl group or an alkoxycarbonyl group and $R^5$ represents a hydrogen atom, a hydroxyl group or an acyloxy group; and 2) isolating the compound from the culture medium.

38. A process for producing the compound represented by formula [13], wherein the process comprises the steps of: 1) cultivating in a culture medium a compound-producing fungus which belongs to the genus *Penicillium*, which is *Penicillium* sp. SPF-3059 having accession number FERM BP-7663, to produce a compound of formula [13],

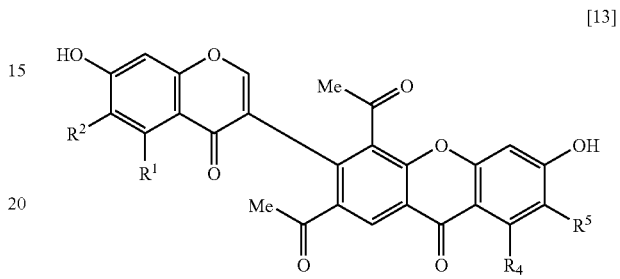

[13]

wherein $R^1$ represents a hydrogen atom, a carboxyl group or an alkoxycarbonyl group, $R^2$ represents a hydrogen atom, a hydroxyl group or an acyloxy group, $R^4$ represents a hydrogen atom, a carboxyl group or an alkoxycarbonyl group and $R^5$ represents a hydrogen atom, a hydroxyl group or an acyloxy group; and 2) isolating the compound from the culture medium.

39. A process for producing the compound represented by formula [14], wherein the process comprises the steps of: 1) cultivating in a culture medium a compound-producing fungus which belongs to the genus *Penicillium*, which is *Penicillium* sp. SPF-3059 having accession number FERM BP-7663, to produce a compound of formula [14],

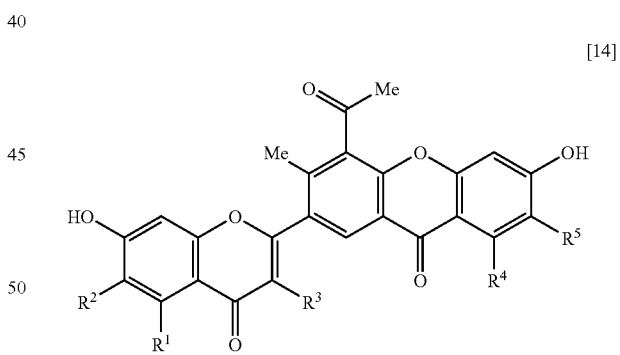

[14]

wherein $R^1$ represents a hydrogen atom, a carboxyl group or an alkoxycarbonyl group, $R^2$ represents a hydrogen atom, a hydroxyl group or an acyloxy group, $R_4$ represents a hydrogen atom, a carboxyl group or an alkoxycarbonyl group, $R_5$ represents a hydrogen atom, a hydroxyl group or an acyloxy group and $R_3$ represents a hydrogen atom, a methoxymethyl group or formula [3]; and 2) isolating the compound from the culture medium.

40. A process for producing the compound represented by formula [15], wherein the process comprises the steps of: 1) cultivating in a culture medium a compound-producing fungus-which belongs to the genus *Penicillium*, which is Penicillium sp. SPF-3059 having accession number FERM BP-7663, to produce a compound of formula [15],

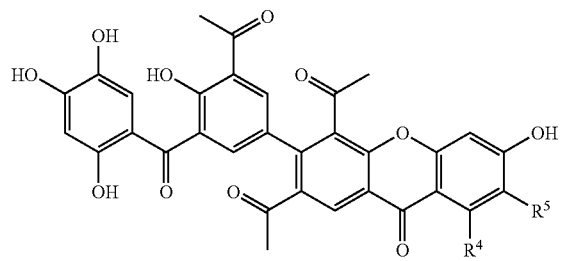

wherein $R^4$ represents a hydrogen atom, a carboxyl group or an alkoxycarbonyl group and $R^5$ represents a hydrogen atom, a hydroxyl group or an acyloxy group; and 2) isolating the compound from the culture medium.

41. A process for producing the compound represented by formula [16], wherein the process comprises tho steps of: 1) cultivating in a culture medium a compound-producing fungus which belongs to the genus *Penicillium* which is *Penicillium* sp. SPF-3059 having accession number FERM BP-7663, to produce a compound of formula [16],

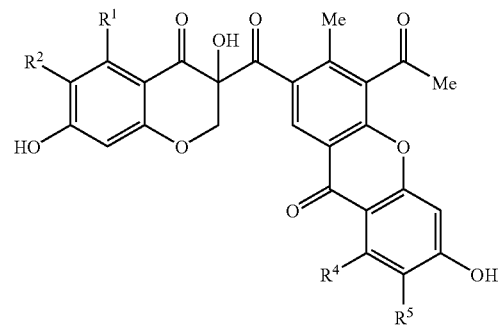

wherein $R^1$ represents a hydrogen atom, a carboxyl group or an alkoxycarbonyl group, $R^2$ represents a hydrogen atom, a hydroxyl group or an acyloxy group, $R^4$ represents a hydrogen atom, a carboxyl group or an alkoxycarbonyl group and $R_5$ represents a hydrogen atom, a hydroxyl group or an acyloxy group; and 2) isolating the compound from the culture medium.

42. *Penicillium* sp. SPF-3059 (FERM BP-7663) or a fungus strain induced from said SPF-3059.

* * * * *